US009884841B2

(12) United States Patent
Nikolovska-Coleska et al.

(10) Patent No.: US 9,884,841 B2
(45) Date of Patent: Feb. 6, 2018

(54) SMALL MOLECULE INHIBITORS OF MCL-1 AND USES THEREOF

(71) Applicant: The Regents of the University of Michigan, Ann Arbor, MI (US)

(72) Inventors: Zaneta Nikolovska-Coleska, Ann Arbor, MI (US); Jeanne A. Stuckey, Fenton, MI (US); Ahmed Mady, Ann Arbor, MI (US); Lei Miao, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/134,098

(22) Filed: Apr. 20, 2016

(65) Prior Publication Data

US 2016/0304485 A1   Oct. 20, 2016

Related U.S. Application Data

(60) Provisional application No. 62/149,987, filed on Apr. 20, 2015.

(51) Int. Cl.
| | |
|---|---|
| *A61K 31/167* | (2006.01) |
| *C07D 333/34* | (2006.01) |
| *A61K 45/06* | (2006.01) |
| *C07C 323/63* | (2006.01) |
| *C07C 311/21* | (2006.01) |
| *C07D 295/26* | (2006.01) |
| *A61K 31/495* | (2006.01) |
| *A61K 31/18* | (2006.01) |
| *A61K 31/415* | (2006.01) |
| *A61K 31/44* | (2006.01) |
| *A61K 31/4409* | (2006.01) |
| *A61K 31/443* | (2006.01) |
| *A61K 31/4439* | (2006.01) |
| *A61K 31/451* | (2006.01) |
| *A61K 31/496* | (2006.01) |
| *A61K 31/5355* | (2006.01) |
| *C07C 311/29* | (2006.01) |
| *C07C 229/64* | (2006.01) |
| *C07C 233/81* | (2006.01) |
| *C07C 235/56* | (2006.01) |

(52) U.S. Cl.
CPC .......... *C07D 333/34* (2013.01); *A61K 31/167* (2013.01); *A61K 31/18* (2013.01); *A61K 31/415* (2013.01); *A61K 31/44* (2013.01); *A61K 31/443* (2013.01); *A61K 31/4409* (2013.01); *A61K 31/4439* (2013.01); *A61K 31/451* (2013.01); *A61K 31/495* (2013.01); *A61K 31/496* (2013.01); *A61K 31/5355* (2013.01); *A61K 45/06* (2013.01); *C07C 229/64* (2013.01); *C07C 233/81* (2013.01); *C07C 235/56* (2013.01); *C07C 311/21* (2013.01); *C07C 311/29* (2013.01); *C07C 323/63* (2013.01); *C07D 295/26* (2013.01)

(58) Field of Classification Search
USPC .......................... 514/255.03, 443, 445, 562
See application file for complete search history.

(56) References Cited

U.S. PATENT DOCUMENTS

| | | |
|---|---|---|
| 8,232,273 B2 | 7/2012 | Baell et al. |
| 2013/0035304 A1 | 2/2013 | Walensky et al. |
| 2014/0235702 A1 | 8/2014 | Nikolovska-Coleska et al. |
| 2015/0045357 A1 | 2/2015 | Nikolovska-Coleska et al. |

FOREIGN PATENT DOCUMENTS

WO   WO 2010/005922 A1 *   1/2010   ............ A01N 41/06

OTHER PUBLICATIONS

Agrawal (Organic Letters; 2013, 15(1), 96-99).*
Petros et al. "Fragment-based discovery of potent inhibitors of the anti-apoptotic MCL-1 protein" Bioogranic & Medicinal Chemistry Letters, Feb. 14, 2014, vol. 24, p. 1484-1488.
Chen et al. "Small-Molecule Inhibitors of the Mcl-1 Oncoprotein" Austin Jounral of Analytical and Pharmaceutical Chemistry. Oct. 10, 2014, vol. 1, p. 1-6.
Chen S, et al., "Mcl-1 down-regulation potentiates ABT-737 lethality by cooperatively inducing Bak activation and Bax translocation." Cancer Res. 2007;67:782-91.
Day CL, et al., "Solution structure of prosurvival Mcl-1 and characterization of its binding by proapoptotic BH3-only ligands." J Biol Chem. 2005;280:4738-44.
Day CL, et al., "Structure of the BH3 domains from the p53-inducible BH3-only proteins Noxa and Puma in complex with Mcl-1." J Mol Biol. 2008;380:958-71.
Du, Y., et al., "A Dual-Readout F2 Assay That Combines Fluorescence Resonance Energy Transfer and Fluorescence Polarization for Monitoring Bimolecular Interactions" Assay and drug development technologies 9(4), 2011, 382-393.
Guoan X, et al., "Adenovirus-mediated siRNA targeting Mcl-1 gene increases radiosensitivity of pancreatic carcinoma cells in vitro and in vivo." Surgery. 2010;147:553-61.
Huang S, et al., "The BH3 mimetic ABT-737 potentiates Trail-mediated apoptotic signaling by unsequestering Bim and Bak in human pancreatic cancer cells." Cancer Res. 2008;68:2944-51.
Konopleva, M., et al., "Mechanisms of apoptosis sensitivity and resistance to the BH3 mimetic ABT-737 in acute myeloid leukemia." (2006) Cancer cell 10, 375-388.
Lin, X., et al., "'Seed' analysis of off-target siRNAs reveals an essential role of Mcl-1 in resistance to the small-molecule Bcl-2/Bcl-XL inhibitor ABT-737" (2007) Oncogene 26, 3972-3979.
Macarron R., et al., "Impact of high-throughput screening in biomedical research." Nat Rev Drug Discov 2011, 10, 188-95.
Miyamoto Y, et al., "Immunohistochemical analysis of Bcl-2, Bax, Bcl-X, and Mcl-1 expression in pancreatic cancers." Oncology. 1999;56:73-82.

(Continued)

*Primary Examiner* — Pancham Bakshi
(74) *Attorney, Agent, or Firm* — Casimir Jones, SC

(57) ABSTRACT

This invention is in the field of medicinal chemistry. In particular, the invention relates to a new class of small-molecules having benzoic acid structure which function as inhibitors of Mcl-1 protein, and their use as therapeutics for the treatment of cancer and other diseases.

2 Claims, 8 Drawing Sheets

(56) References Cited

OTHER PUBLICATIONS

Oltersdorf T, et al., "An inhibitor of Bcl-2 family proteins induces regression of solid tumours." Nature. 2005;435:677-81.
Ren LN, et al., "Endocrine glands-derived vascular endothelial growth factor protects pancreatic cancer cells from apoptosis via upregulation of the myeloid cell leukemia-1 protein." Biochem Biophys Res Commun. 2009;386:35-9.
Schniewind B, et al., "Resistance of pancreatic cancer to gemcitabine treatment is dependent on mitochondria-mediated apoptosis" Int J Cancer. 2004;109:182-8.
Sosic, I. et al., "Exploration of the chemical space of novel naphthalene-sulfonamide and anthranilic Acid-based inhibitors of penicillin-binding proteins." Acta Chim. Slov. 2012, 59, 380-388.
Tse C, et al., "ABT-263: a potent and orally bioavailable Bcl-2 family inhibitor." Cancer Res. 2008;68:3421-8.
Van Delft MF, et al., "The BH3 mimetic ABT-737 targets selective Bcl-2 proteins and efficiently induces apoptosis via Bak/Bax if Mcl-1 is neutralized." Cancer Cell. 2006;10:389-99.
Wei SH, et al., "Inducing apoptosis and enhancing chemosensitivity to gemcitabine via RNA interference targeting Mcl-1 gene in pancreatic carcinoma cell." Cancer Chemother Pharmacol. 2008;62:1055-64.
Wydysh, E. A. et al. "Design and synthesis of small molecule glycerol 3-phosphate acyltransferase inhibitors." J. Med. Chem. 2009, 52, 3317-3327.
Zhou P, et al., "Mcl-1, a Bcl-2 family member, delays the death of hematopoietic cells under a variety of apoptosis-inducing conditions." Blood. 1997;89(2):630-43.

* cited by examiner

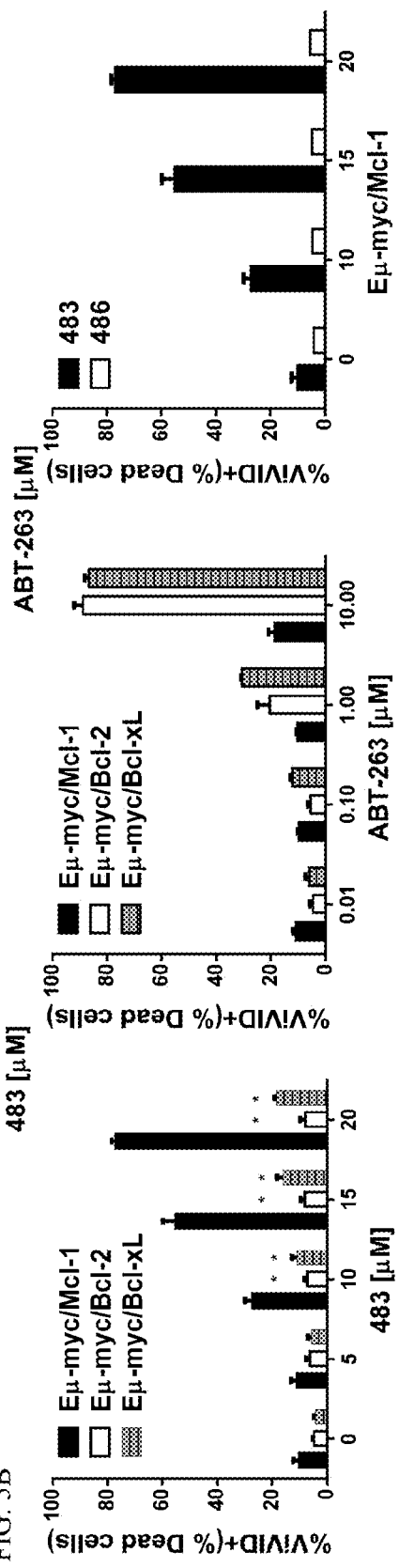
FIG. 5A
FIG. 5B

SMALL MOLECULE INHIBITORS OF MCL-1 AND USES THEREOF

CROSS REFERENCE TO RELATED APPLICATIONS

The present invention claims priority to U.S. Provisional Patent Application 62/149,987, filed Apr. 20, 2015, which is incorporated by reference in its entirety.

STATEMENT REGARDING FEDERALLY SPONSORED RESEARCH OR DEVELOPMENT

This invention was made with government support under CA149442 and CA158976 awarded by the National Institutes of Health. The government has certain rights in the invention.

FIELD OF THE INVENTION

This invention is in the field of medicinal chemistry. In particular, the invention relates to a new class of small-molecules having a benzoic acid structure which function as inhibitors of Mcl-1 protein, and their use as therapeutics for the treatment of cancer and other diseases.

INTRODUCTION

A hallmark of cancer cells is defects in the apoptotic cell death program (see, e.g., Hanahan D, et al., Cell. 2000; 100:57-70; herein incorporated by reference in its entirety). The broad resistance of many types of cancers to existing chemotherapeutic agents and radiation therapy is due, in large part, to defects in apoptotic signaling pathways.

Improved methods for preventing and/or repairing defects in apoptotic signaling pathways are needed.

SUMMARY OF THE INVENTION

Mcl-1 is a potent anti-apoptotic protein and an important survival factor for many human cancers, including breast, pancreatic, colon, lung, ovarian, prostate, melanoma, multiple myeloma, and acute myeloid leukemia. Mcl-1 is highly amplified in human cancer and its overexpression has been associated with tumor initiation, progression and resistance to current anticancer therapies. Recent independent studies using a genetic approach to down-regulation of Mcl-1 provided a significant proof-of-concept that selective, small-molecule Mcl-1 inhibitors may have potential as a new treatment for human cancers by overcoming the apoptosis resistance of cancer cells to current therapeutic agents. Mcl-1 is a homologous protein related to other anti-apoptotic proteins such as Bcl-2 and Bcl-$x_L$, but it has a distinctly different structure and exhibits selective binding to the pro-apoptotic BH3-only proteins. This suggests that specific targeting of the Mcl-1 protein is possible and that drugs specific to Mcl-1 can be developed.

Employing de-novo structure-based drug-design, experiments conducted during the course of developing embodiments for the present invention designed a new class of potent small-molecule Mcl-1 inhibitors based on the initial lead compound discovered by high-throughput screening (see, e.g., Du, Y., et al., Assay and drug development technologies 9, 382-393). Analyzing the binding model of this compound with Mcl-1 through computational docking supported by HSQC NMR studies, and using the structural information, a class of small-molecule inhibitors of Mcl-1 were designed and optimized using a 2,4,5 substituted benzoic acid as a scaffold to reproduce the key interactions with Mcl-1 such as the conserved hydrogen bond between the aspartate in pro-apoptotic proteins and Arg263 in Mcl-1 and hydrophobic interactions by the highly-conserved leucine residue of the pro-apoptotic proteins (Bim, Noxa and Puma). Several co-crystal structures of this class inhibitors in complex with Mcl-1 have provided a basis for their further optimization which ultimately led to the discovery of ligands with low-nanomolar potency (Ki=7 nM). These compounds bind in the canonical BH3 binding groove. Interestingly, depending on the particular substitution pattern in the core scaffold, a "flip" binding mode was observed where the substituents bind in a reverse orientation, confirmed by X-ray crystallography. The most potent compounds have excellent metabolic stability and promising cell activity.

As such, the present invention provides a new class of small-molecules having a benzoic acid structure which function as inhibitors of Mcl-1 protein, and as therapeutics for the treatment of cancer and other diseases.

Accordingly, the present invention contemplates that exposure of animals (e.g., humans) suffering from cancer (e.g., and/or cancer related disorders) to therapeutically effective amounts of drug(s) having a benzoic acid structure (e.g., small molecules having a benzoic acid structure) that inhibit the activity of Mcl-1 will inhibit the growth of cancer cells or supporting cells outright and/or render such cells as a population more susceptible to the cell death-inducing activity of cancer therapeutic drugs or radiation therapies. In some embodiments, the inhibition of Mcl-1 activity occurs through, for example, binding the BH3 binding groove of Mcl-1.

The present invention contemplates that inhibitors of Mcl-1 activity satisfy an unmet need for the treatment of multiple cancer types, either when administered as monotherapy to induce cell growth inhibition, apoptosis and/or cell cycle arrest in cancer cells, or when administered in a temporal relationship with additional agent(s), such as other cell death-inducing or cell cycle disrupting cancer therapeutic drugs or radiation therapies (combination therapies), so as to render a greater proportion of the cancer cells or supportive cells susceptible to executing the apoptosis program compared to the corresponding proportion of cells in an animal treated only with the cancer therapeutic drug or radiation therapy alone.

In certain embodiments of the invention, combination treatment of animals with a therapeutically effective amount of a compound of the present invention and a course of an anticancer agent produces a greater tumor response and clinical benefit in such animals compared to those treated with the compound or anticancer drugs/radiation alone. Since the doses for all approved anticancer drugs and radiation treatments are known, the present invention contemplates the various combinations of them with the present compounds.

The Applicants have found that certain benzoic acid compounds function as inhibitors of Mcl-1 protein, and serve as therapeutics for the treatment of cancer and other diseases. Thus, the present invention relates to benzoic acid compounds useful for inhibiting Mcl-1 activity (e.g., thereby facilitating cell apoptosis), and increasing the sensitivity of cells to inducers of apoptosis and/or cell cycle arrest. Certain benzoic acid compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

In a particular embodiment, benzoic acid compounds encompassed within Formula I are provided:

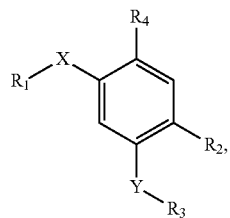

including pharmaceutically acceptable salts, solvates, and/or prodrugs thereof.

Formula I is not limited to a particular chemical moiety for R1, R2, R3, R4, X or Y. In some embodiments, the particular chemical moiety for R1, R2, R3, R4, X or Y independently include any chemical moiety that permits the resulting compound to bind the BH3 binding pocket of Mcl-1 protein.

In some embodiments, X is a linker. In some embodiments, X is

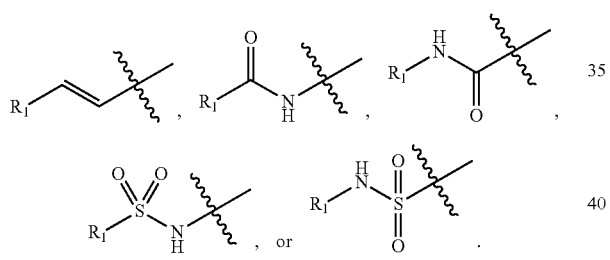

In some embodiments, X is absent.

In some embodiments, R1 is a substituted or non-substituted moiety comprising H, C, N, O, and/or S. In some embodiments, R1 is selected from

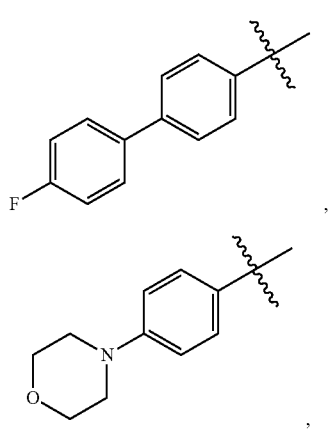

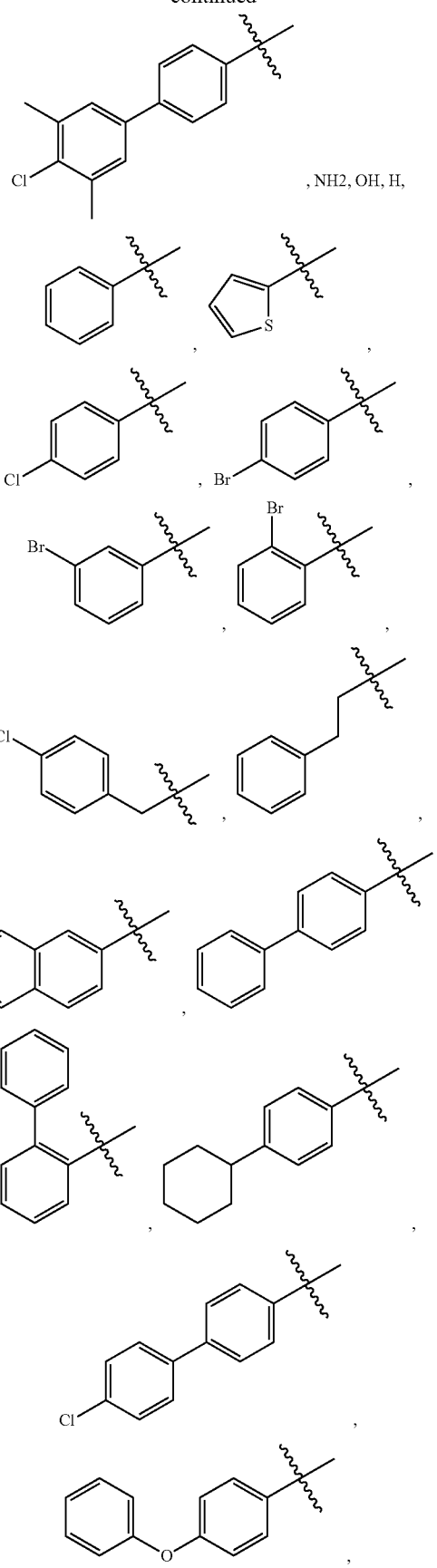

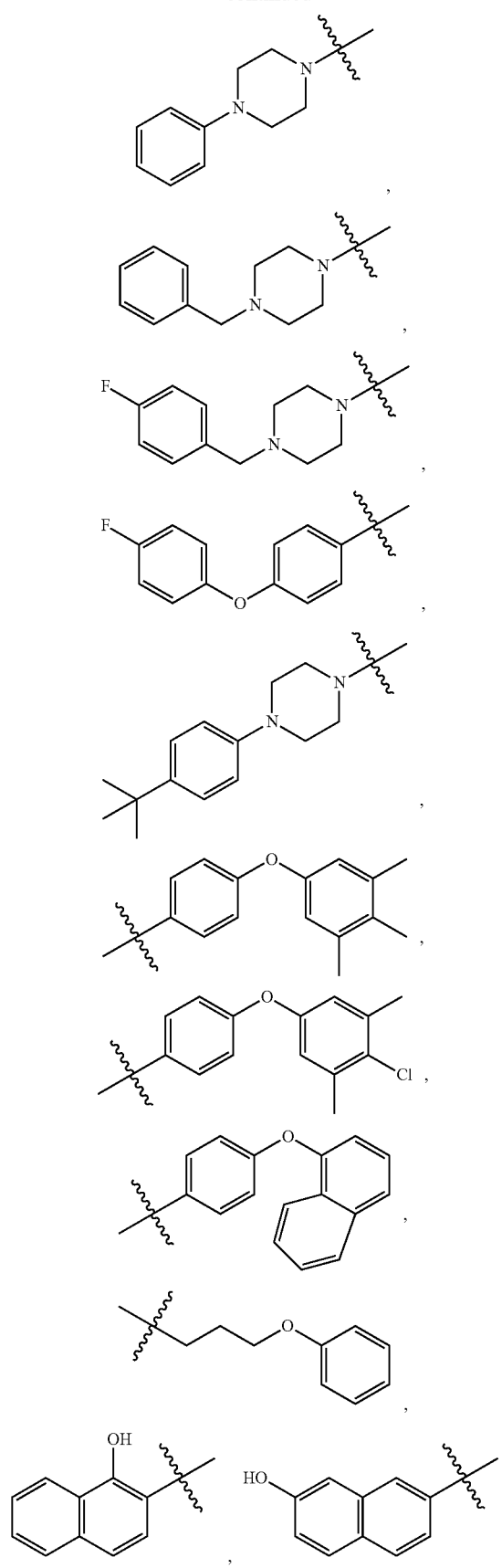
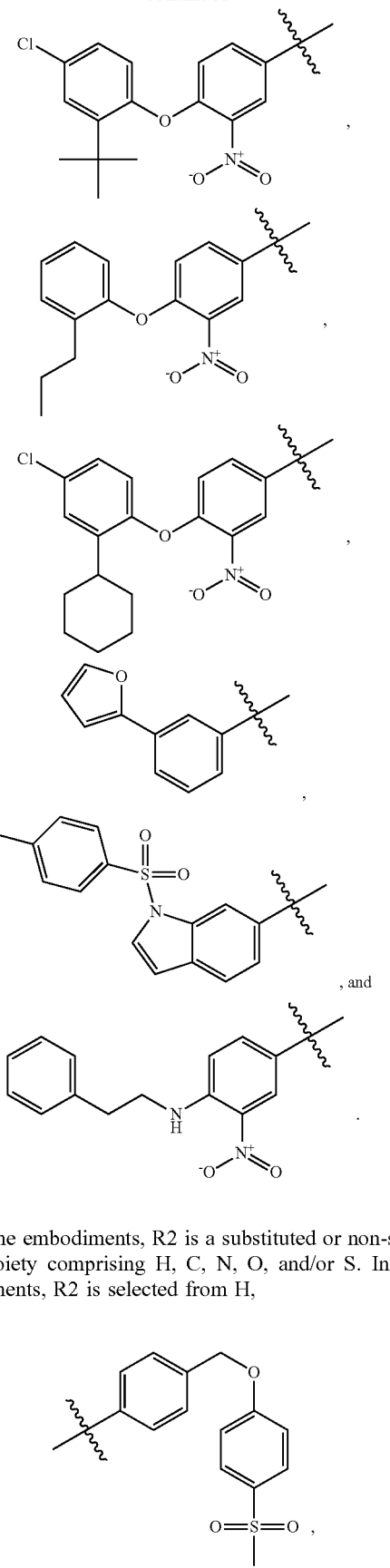
In some embodiments, R2 is a substituted or non-substituted moiety comprising H, C, N, O, and/or S. In some embodiments, R2 is selected from H,
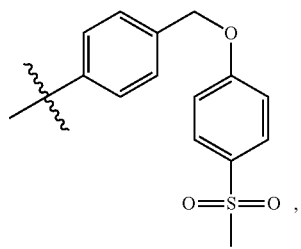

7
-continued
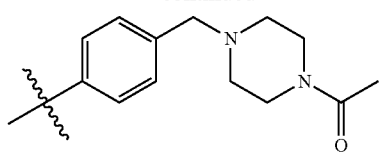
,
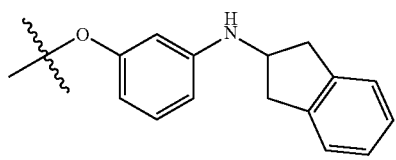
,
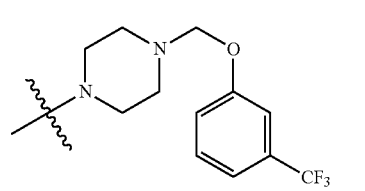
,
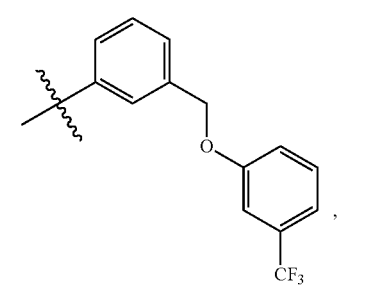
,
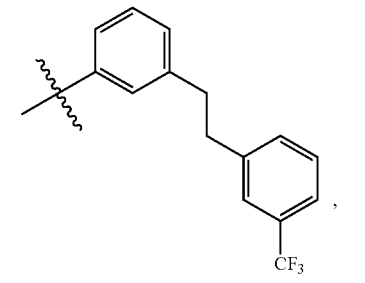
,
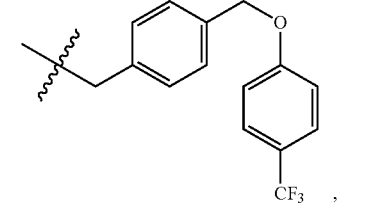
,
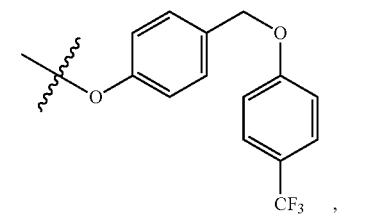
,
8
-continued
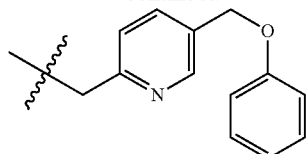
,
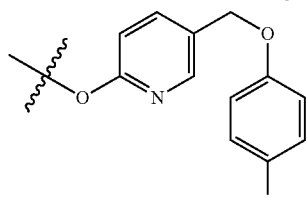
,
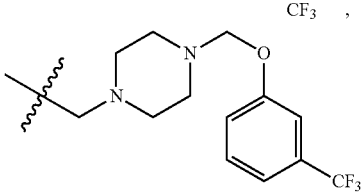
,
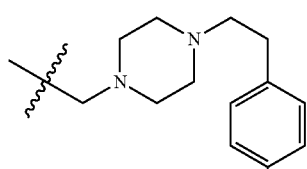
,
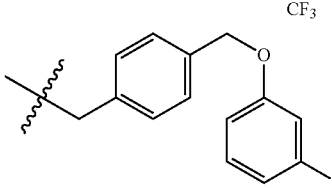
,
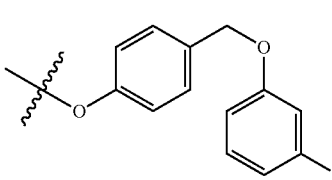
,
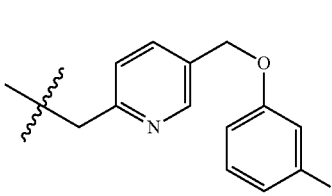
,
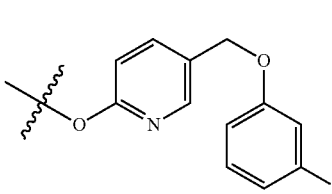
, -continued
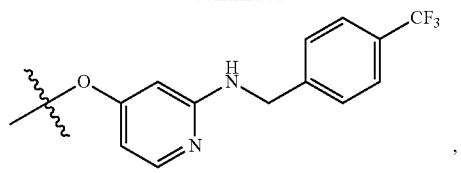
,
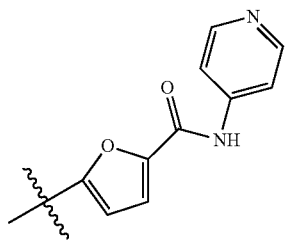
,
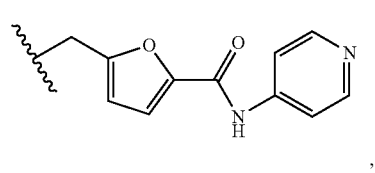
,
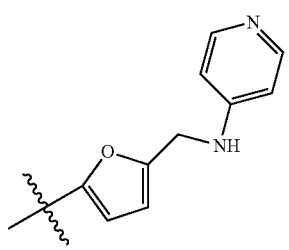
,
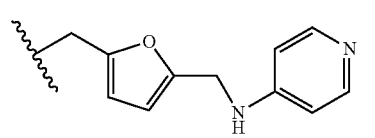
,
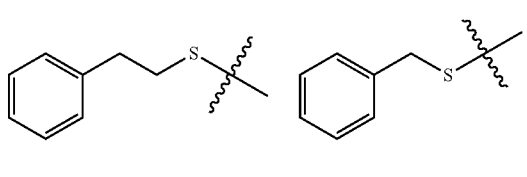
,
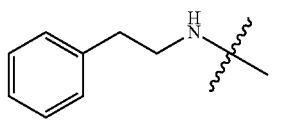
,
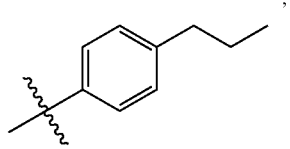
,
-continued
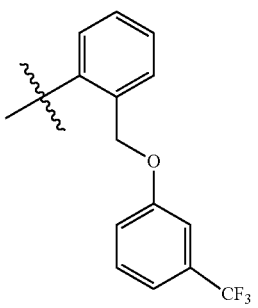
,
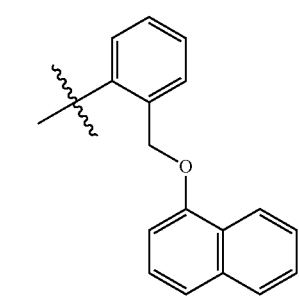
,
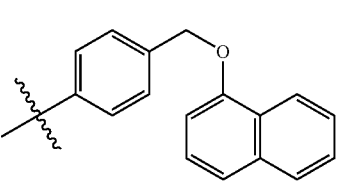
,
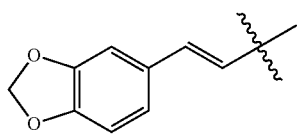
,
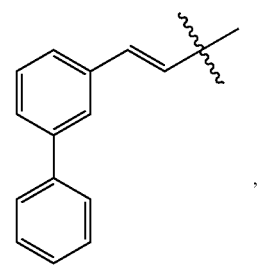
, -continued
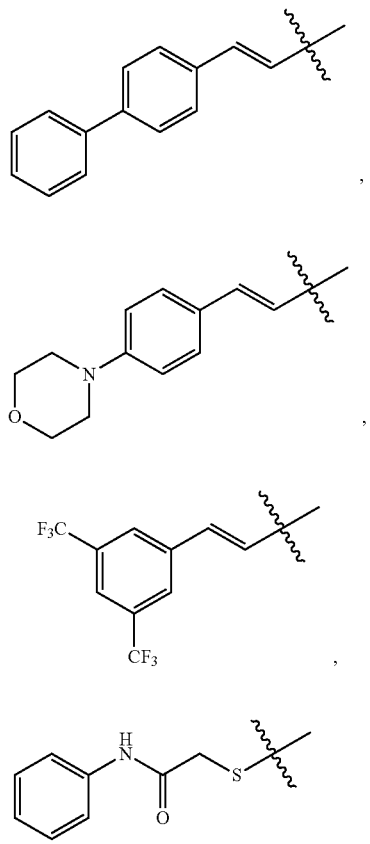
In some embodiments, Y-R3 is absent. In some embodiments, R3 is absent from Y-R3 (e.g., in some embodiments Y-R3 is Y) and Y can be selected from
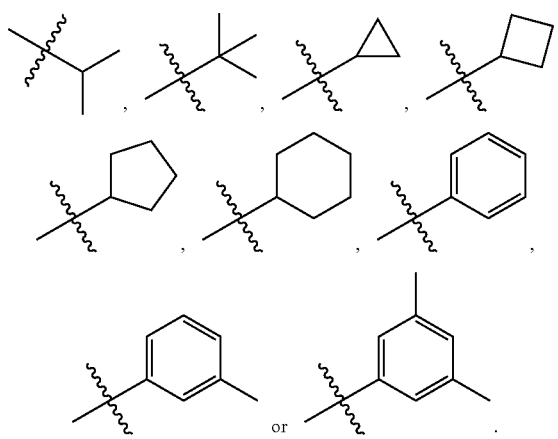
In some embodiments Y is selected from
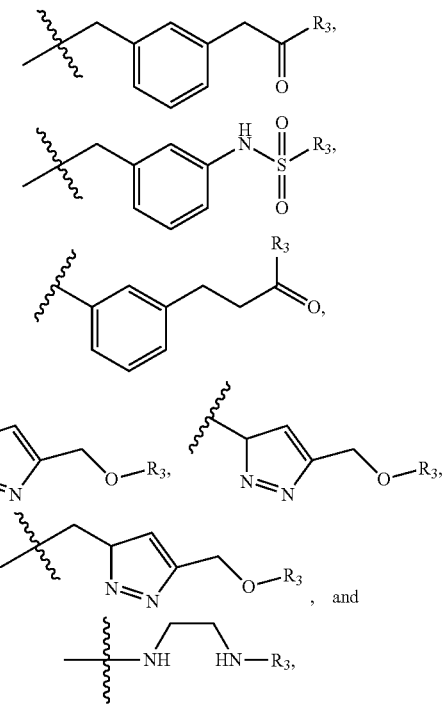
and R3 is selected from the group consisting of hydrogen
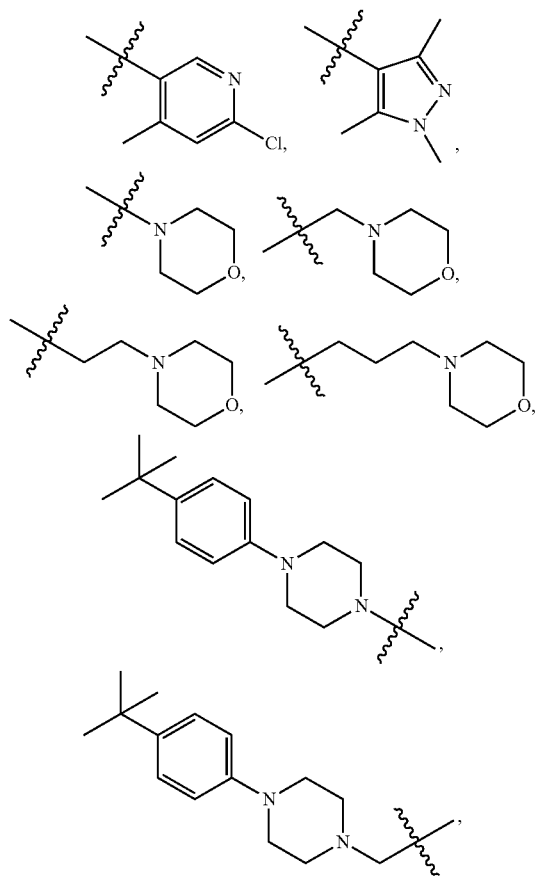

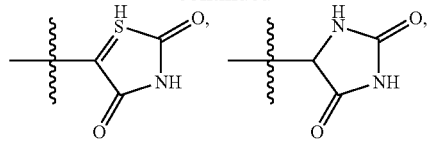
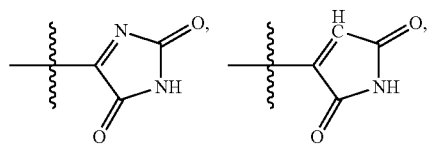

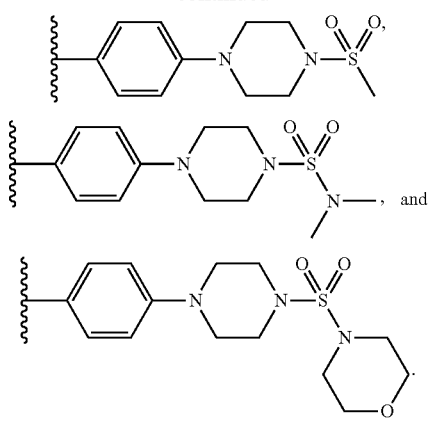

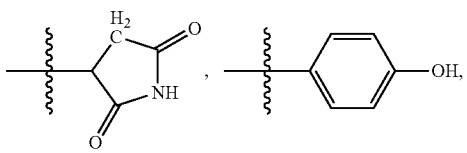

In some embodiments, R4 is an acid moiety. In some embodiments, R4 is an ester moiety. In some embodiments, R4 is hydrogen. In some embodiments, R4 is $CH_3$. In some embodiments, R4 is OH. In some embodiments, R4 is a carboxylic acid bioisostere moiety. In some embodiments, R4 is selected from H, OH, $OCH_3$, $OCH_2CH_3$, COOH, $COOCH_3$, $COOCH_2CH_3$,

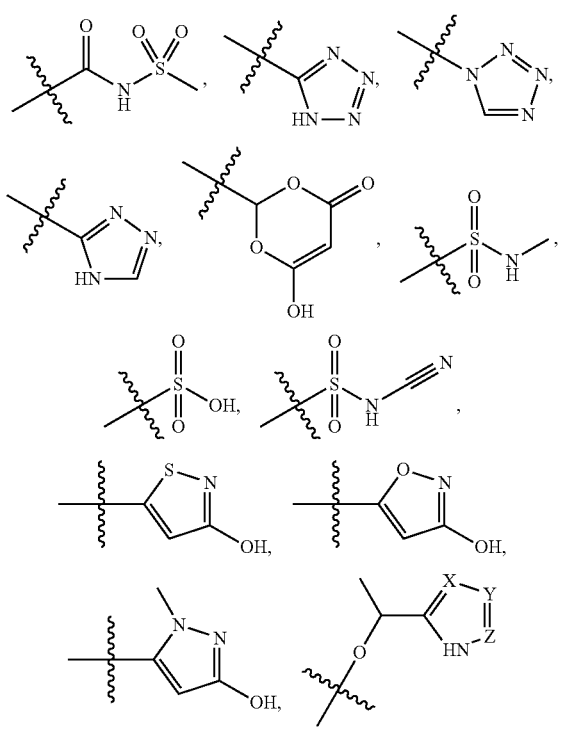

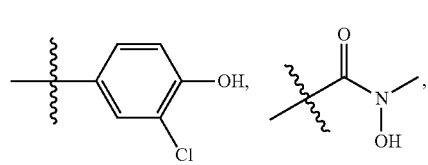

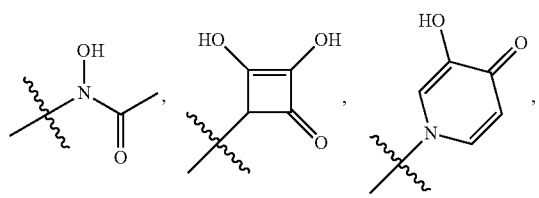

(wherein X, Y, Z are independently N, C or CO),

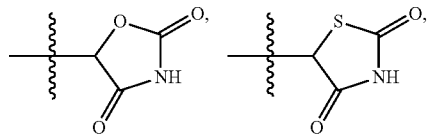

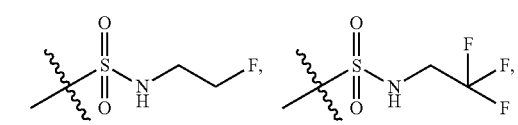

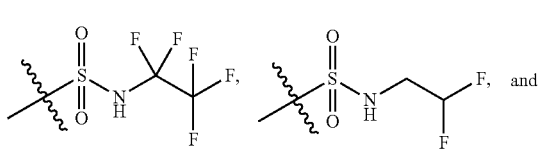

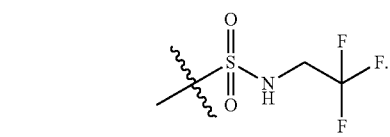

Table 1 (see, Examples) show binding affinities ($K_i$ values) and inhibition against Mcl-1 for various compounds encompassed within Formula I.

In some embodiments, the following compounds are contemplated for Formula I:

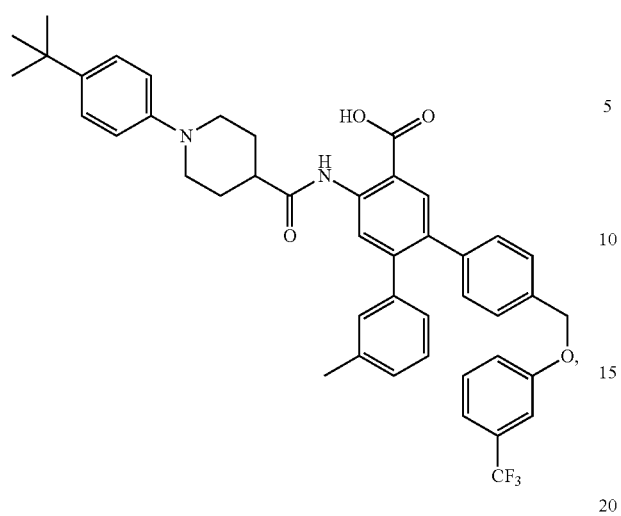
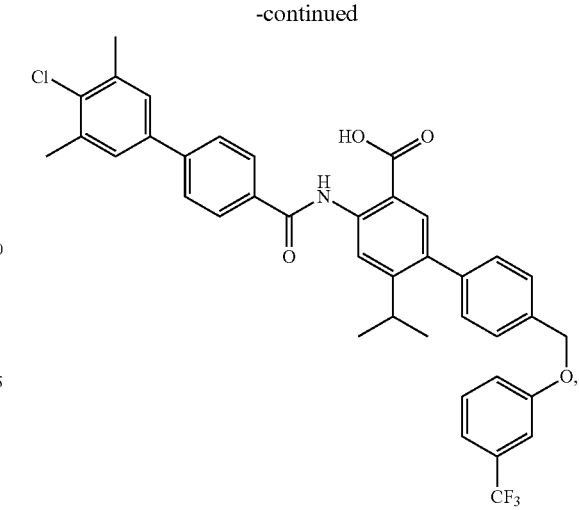
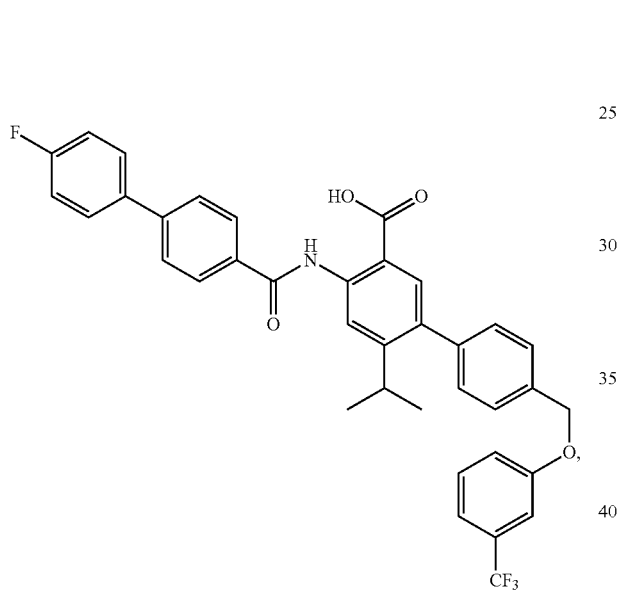
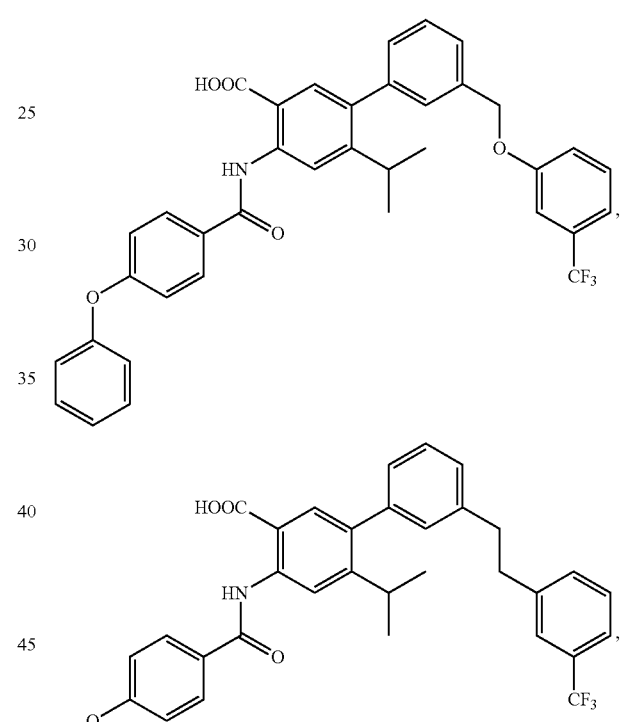
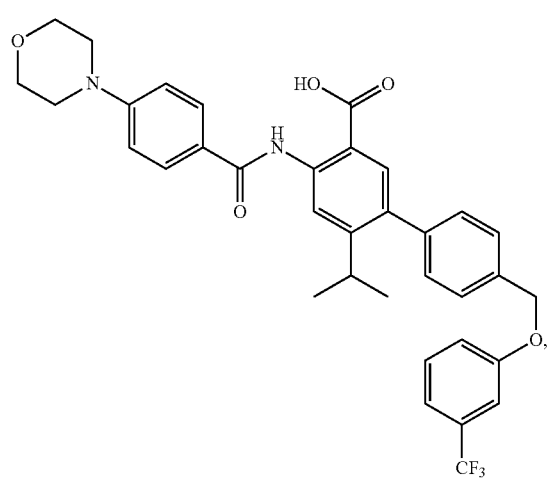

17
-continued
18
-continued
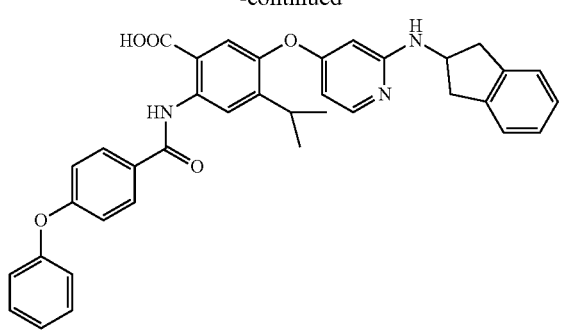
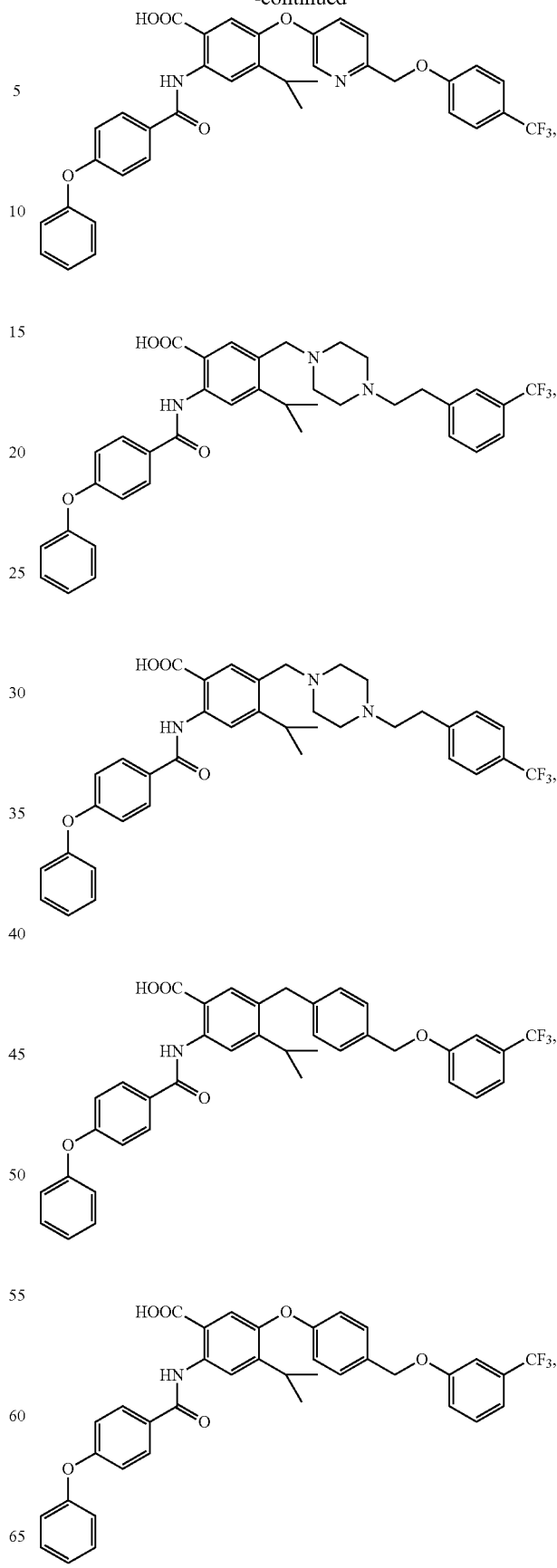

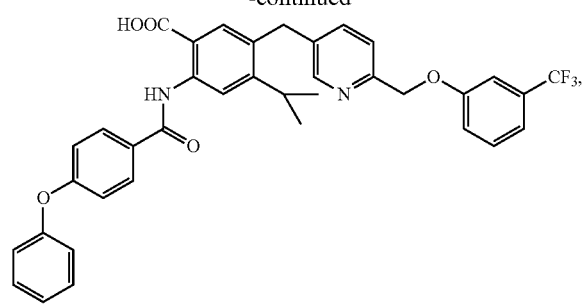
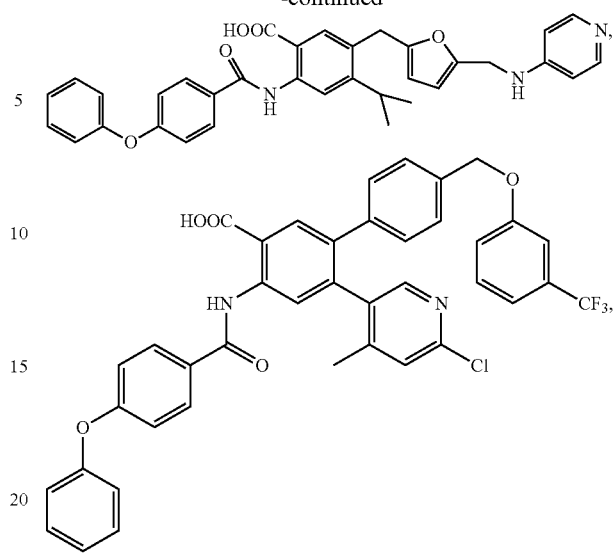
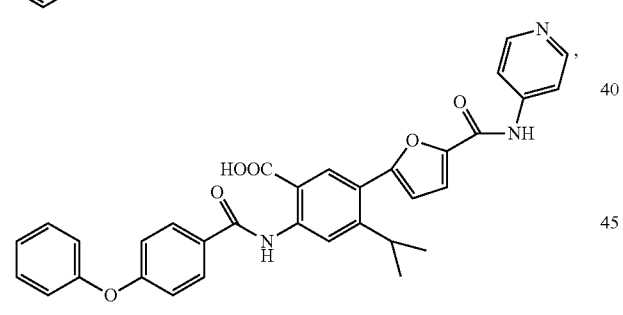
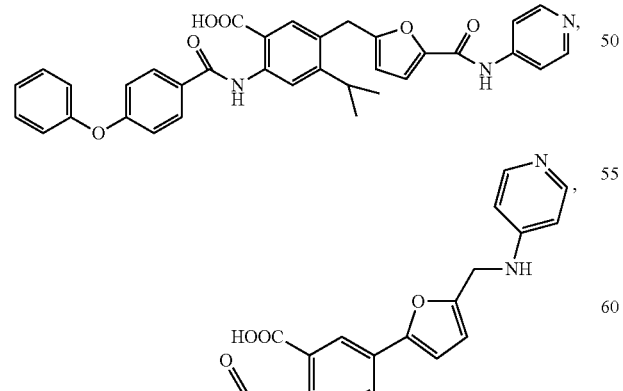

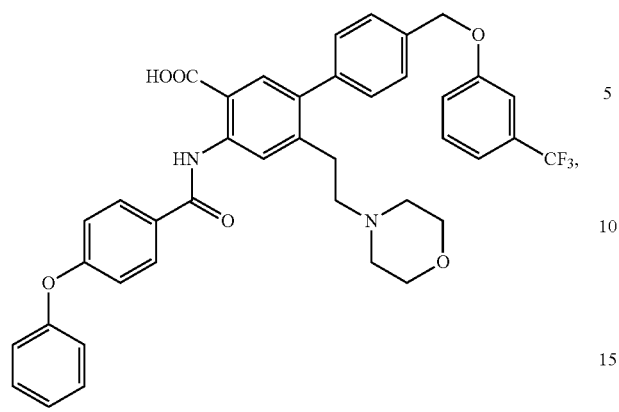
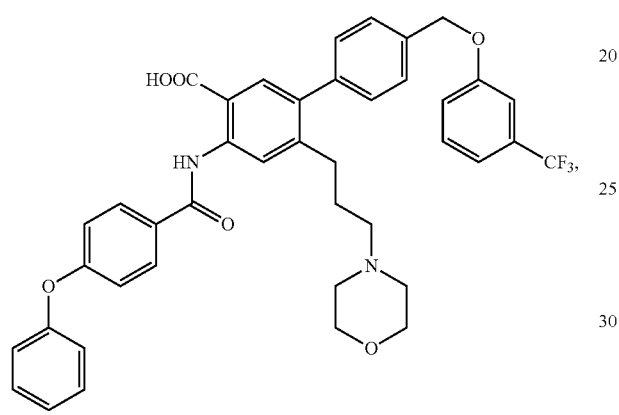
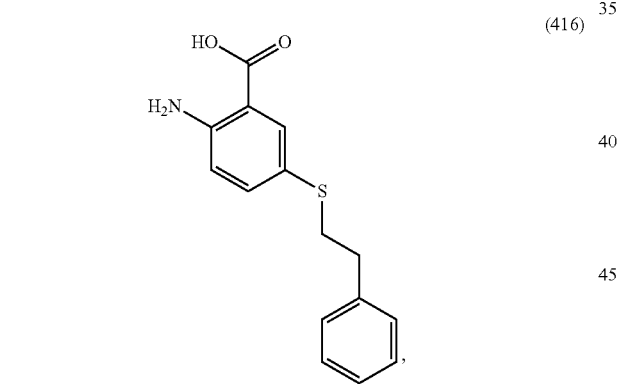
(416)
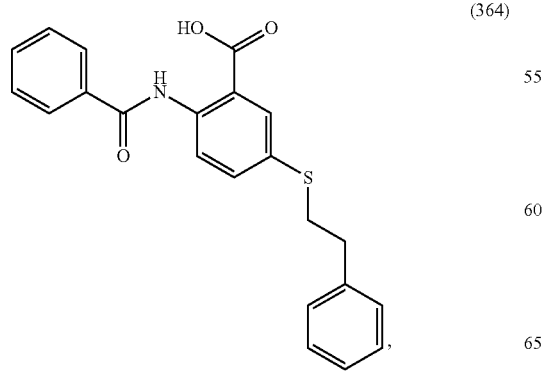
(364)
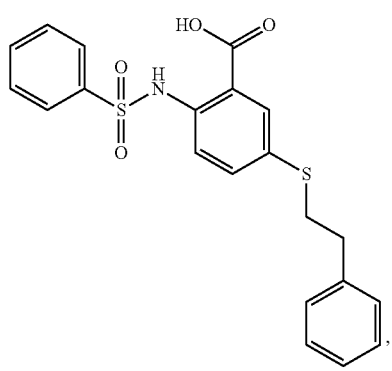
(368)
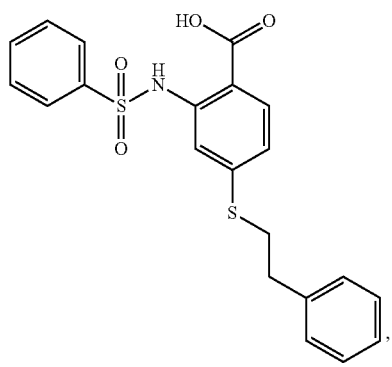
(702)
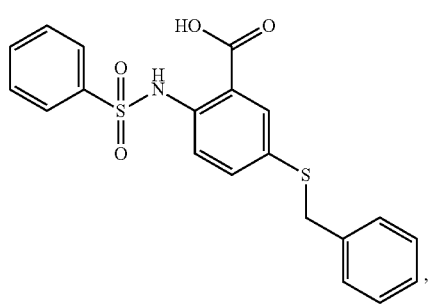
(392)
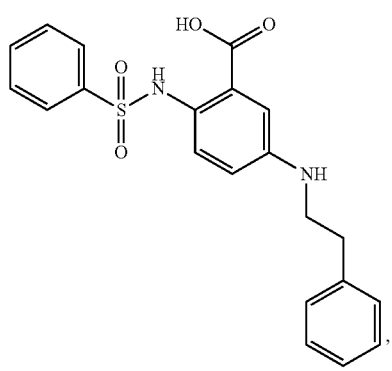
(404)
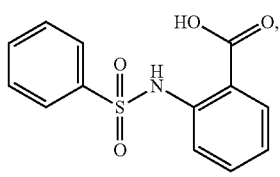
(455)

-continued
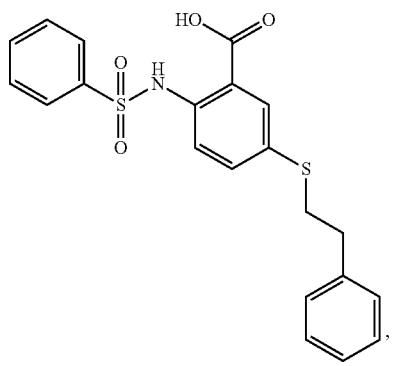
(368)
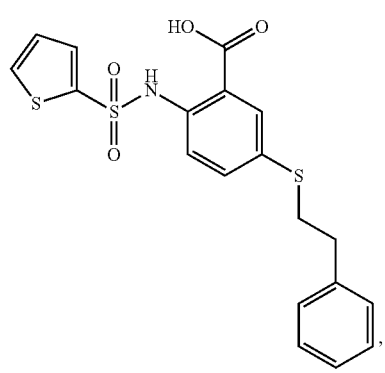
(387)
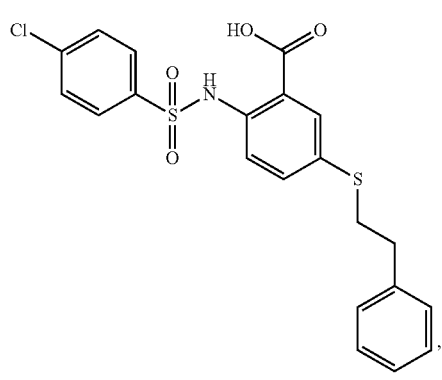
(381)
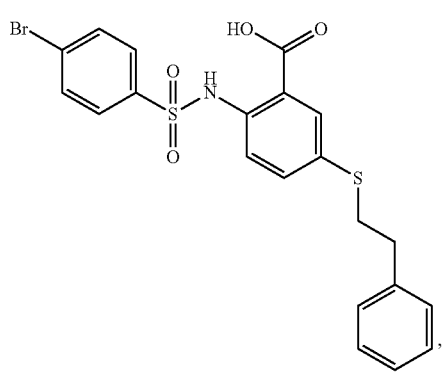
(389)
-continued
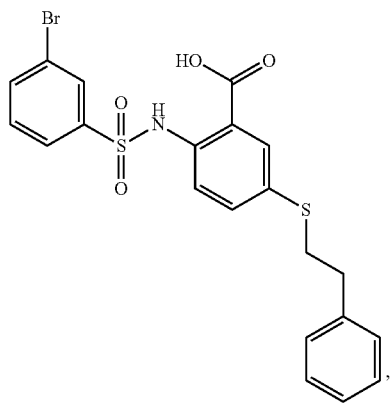
(384)
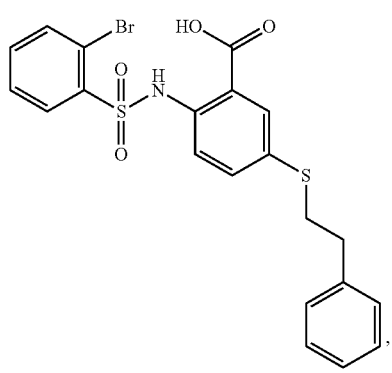
(386)
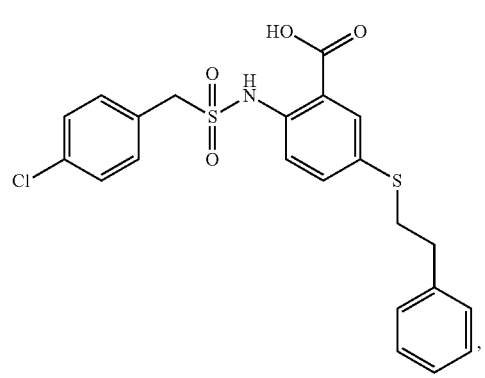
(398)
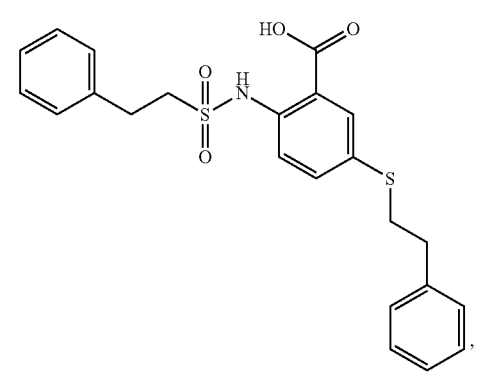
(443)

(454)
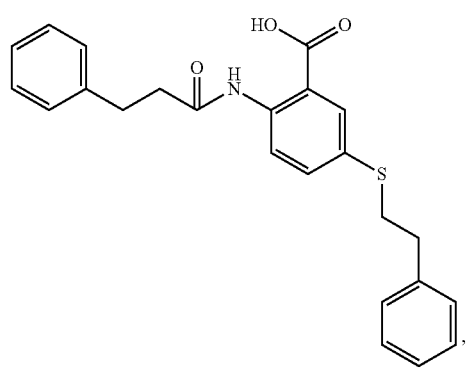
(382)
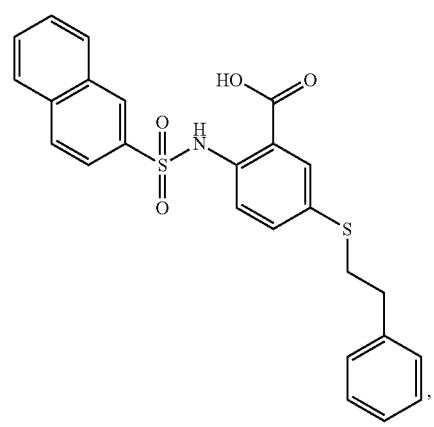
(378)
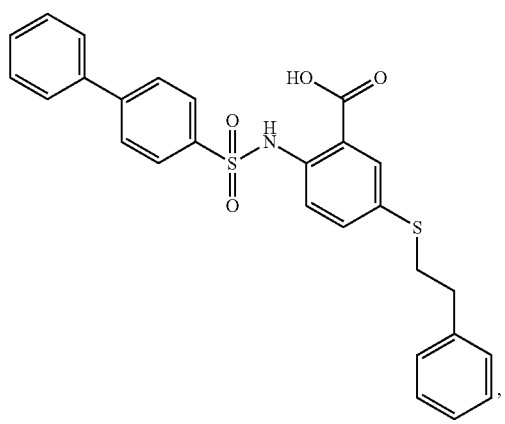
(458)
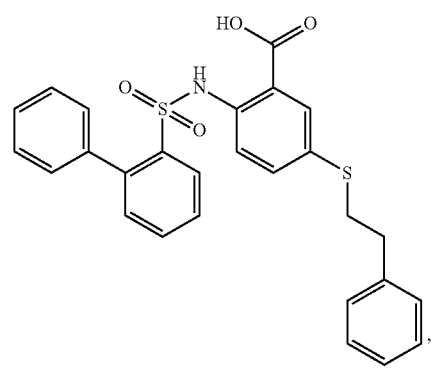
(418)
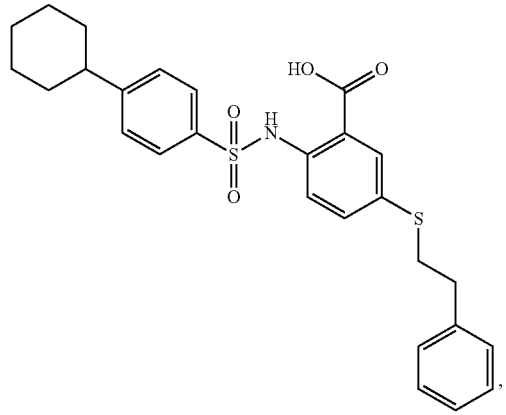
(380)
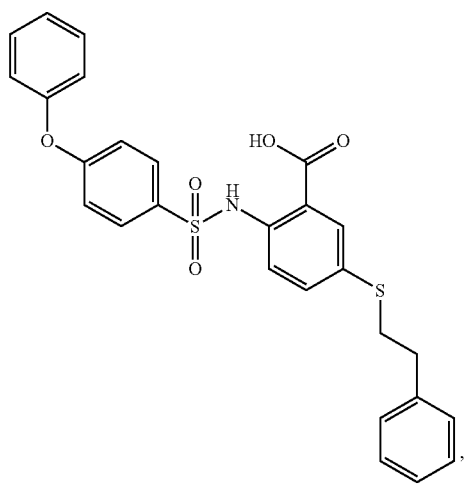
(376)

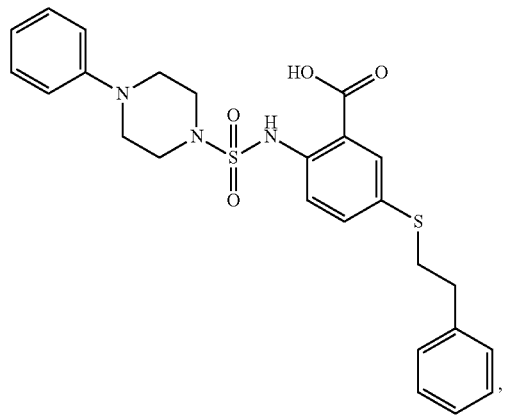
(396)
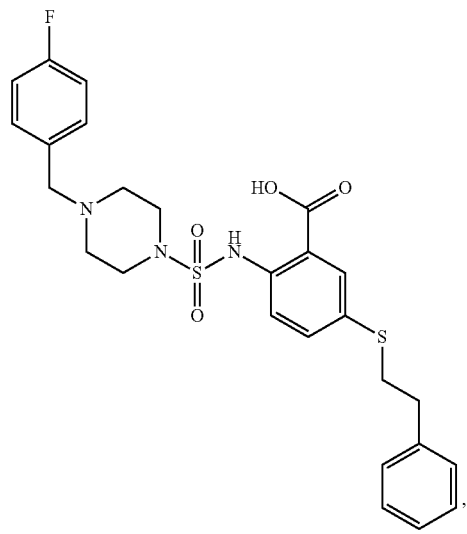
(462)
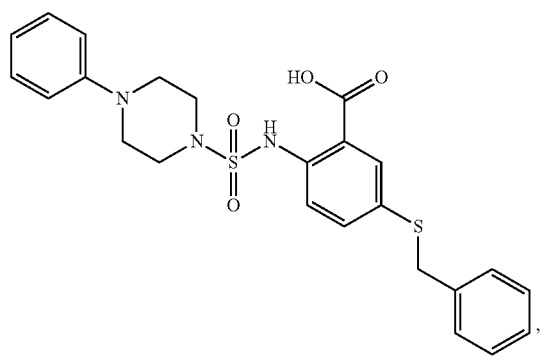
(456)
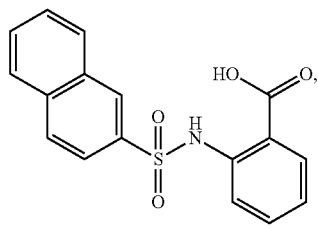
(453)
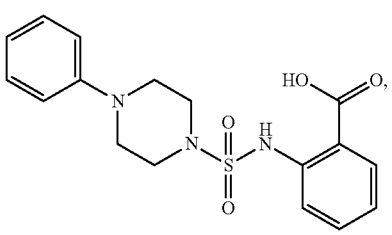
(460)
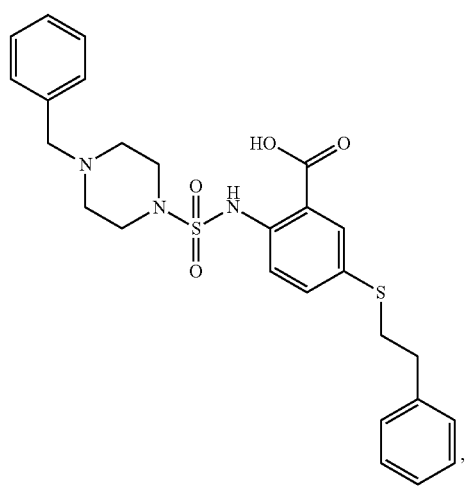
(414)
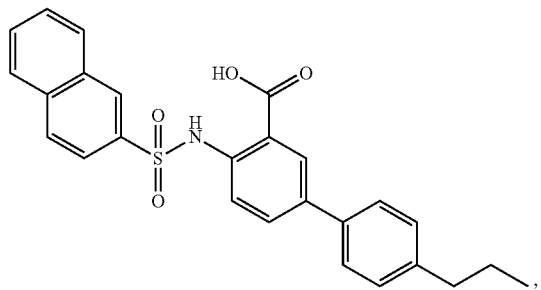
(466)

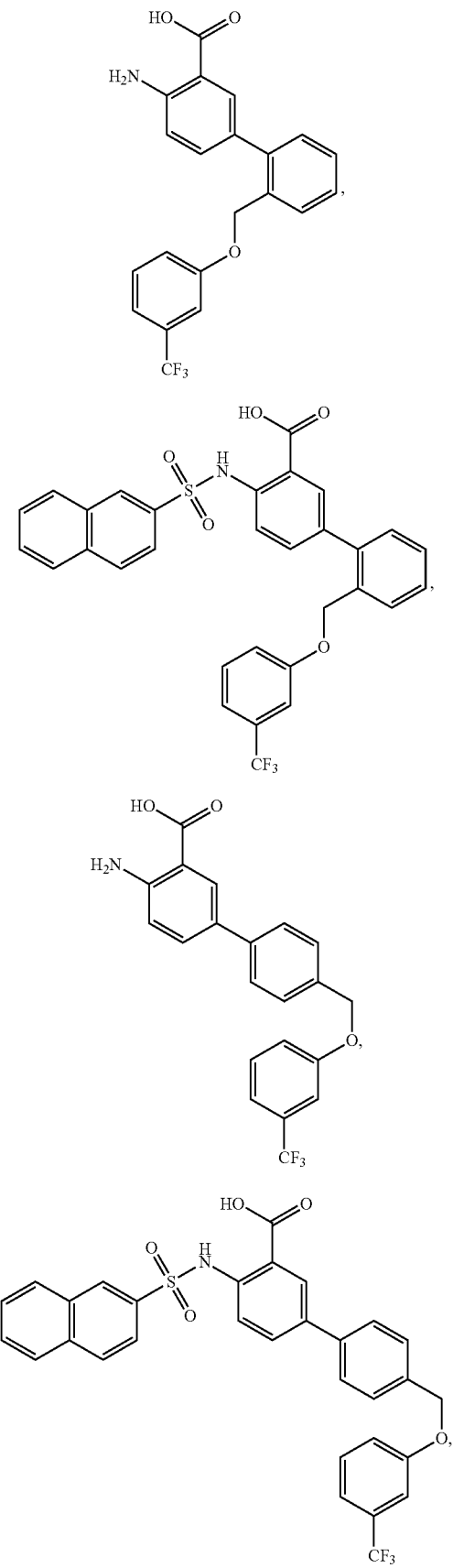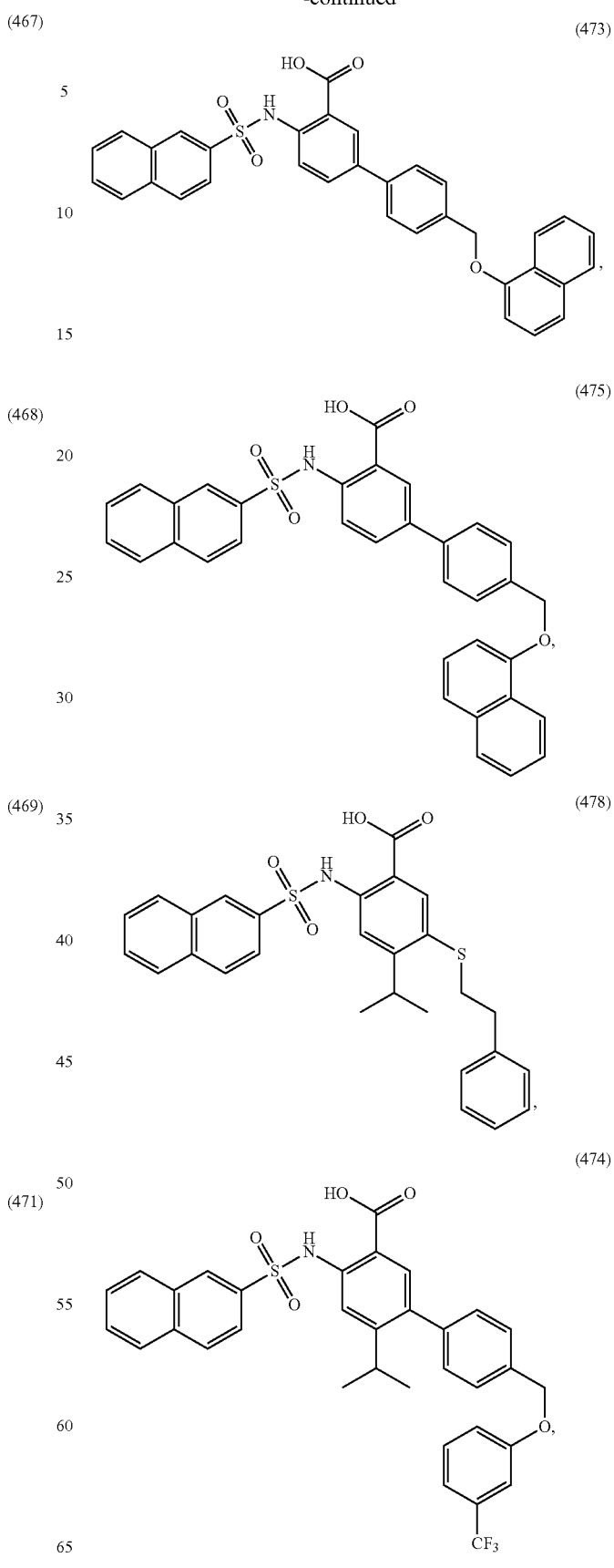

(476)
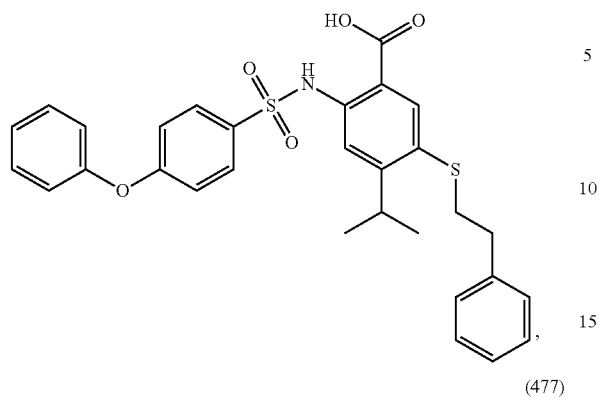
(477)
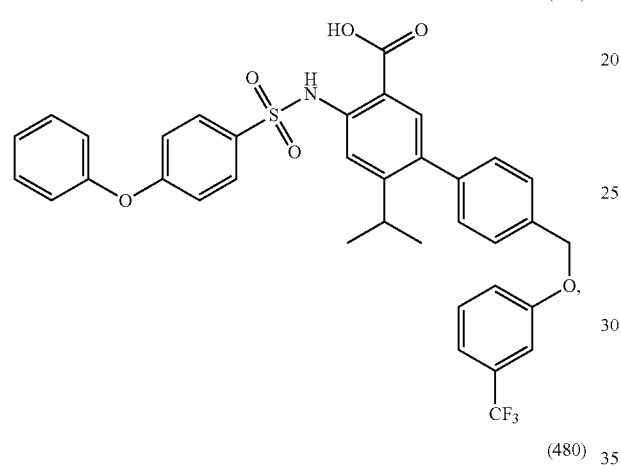
(480)
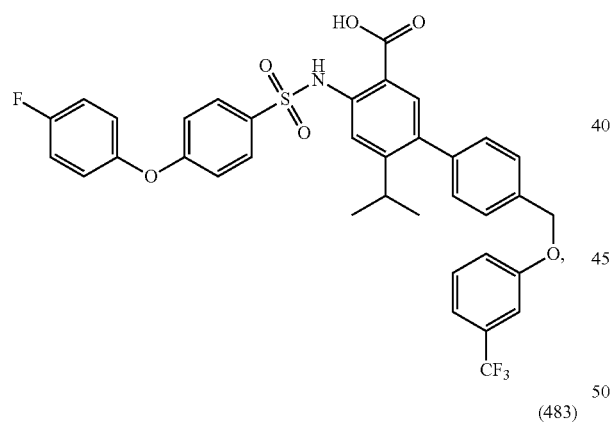
(483)
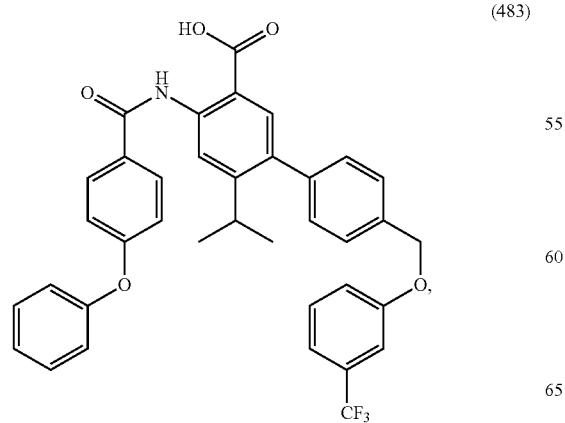
(487)
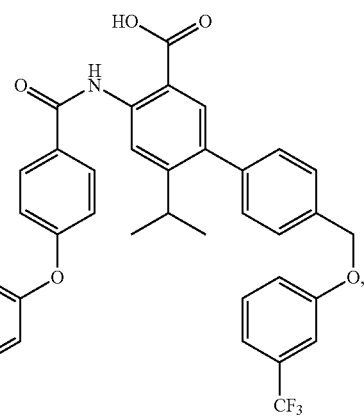
(481)
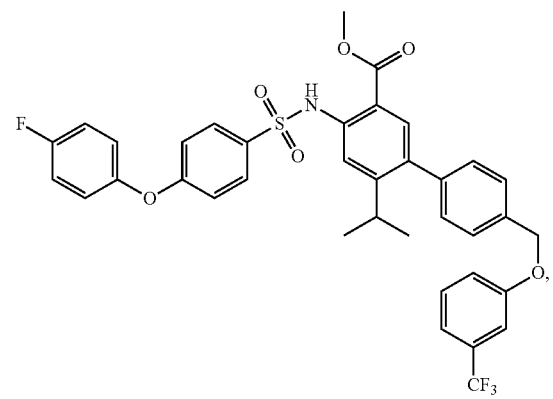
(482)
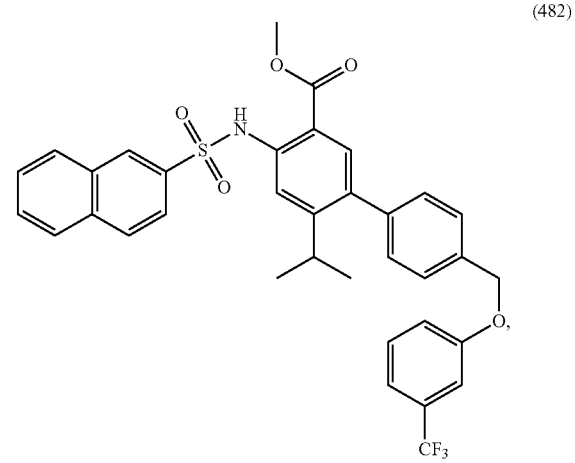

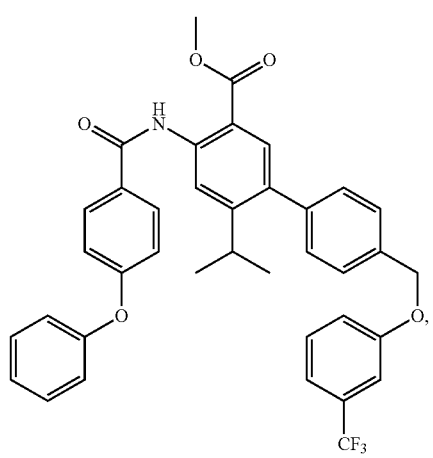
(486)
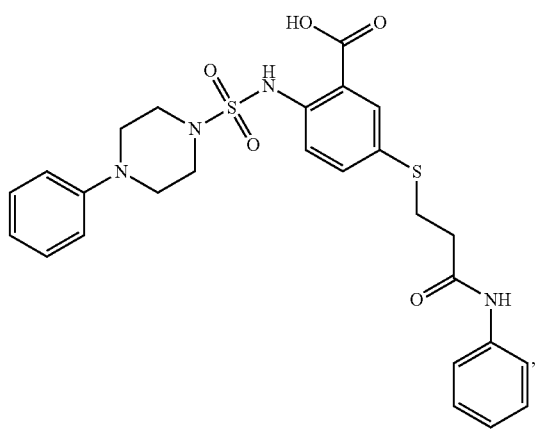
(429)
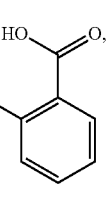
(460)
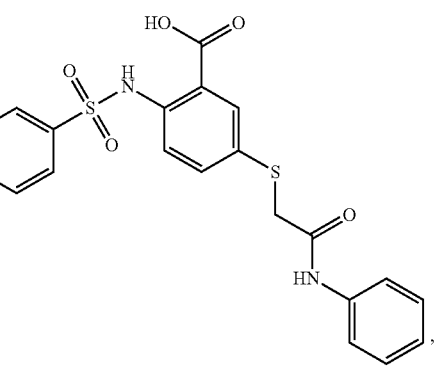
(395)
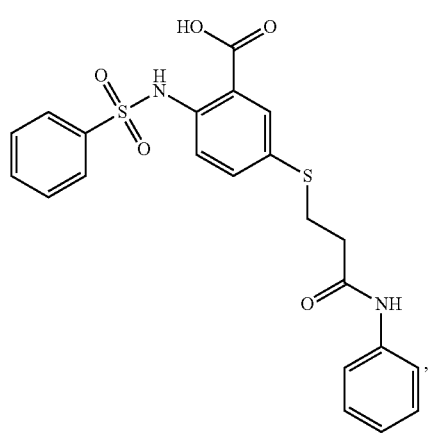
(410)
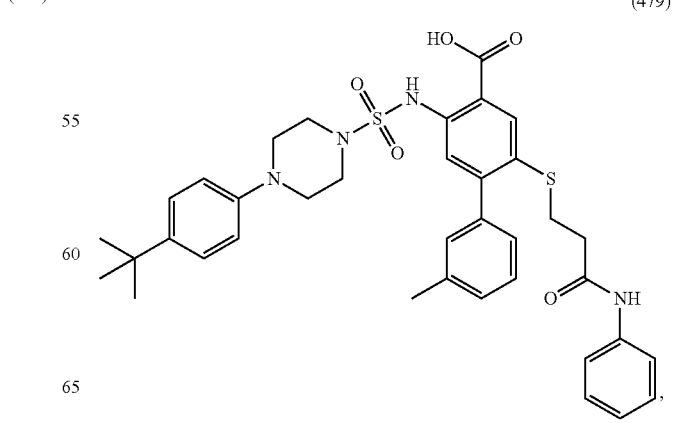
(435)
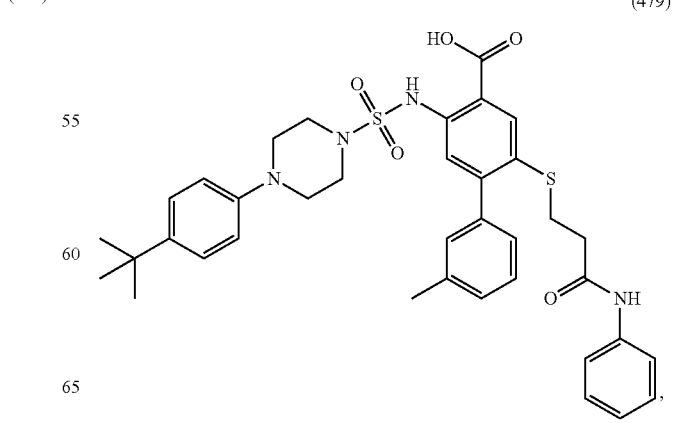
(479)

-continued

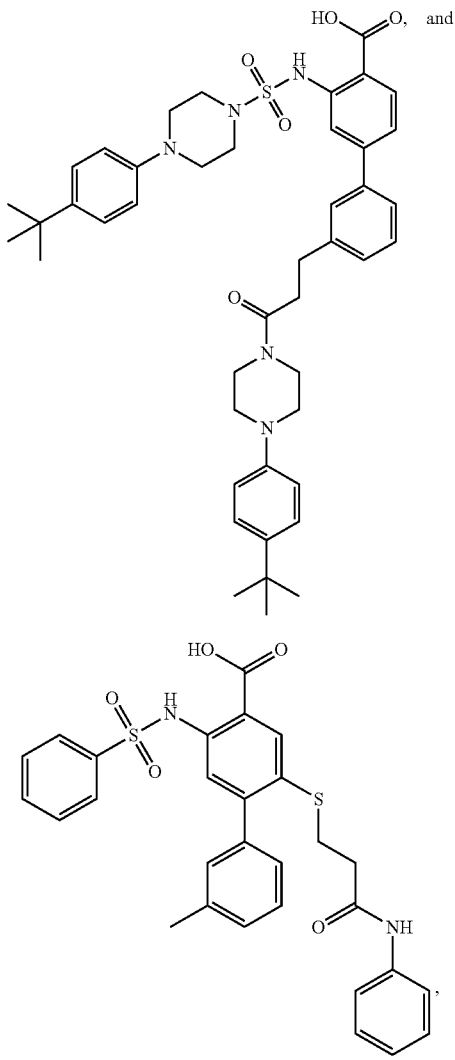
(484)

(485)

or a pharmaceutically acceptable salt, solvate, or prodrug thereof.

The invention further provides processes for preparing any of the compounds of the present invention through following at least a portion of the techniques recited the Examples.

The invention also provides the use of compounds to induce cell cycle arrest and/or apoptosis in cells containing functional Mcl-1 proteins. The invention also relates to the use of compounds for sensitizing cells to additional agent(s), such as inducers of apoptosis and/or cell cycle arrest, and chemoprotection of normal cells through the induction of cell cycle arrest prior to treatment with chemotherapeutic agents.

The compounds of the invention are useful for the treatment, amelioration, or prevention of disorders, such as those responsive to induction of apoptotic cell death, e.g., disorders characterized by dysregulation of apoptosis, including hyperproliferative diseases such as cancer. In certain embodiments, the compounds can be used to treat, ameliorate, or prevent cancer that is characterized by resistance to cancer therapies (e.g., those cancer cells which are chemoresistant, radiation resistant, hormone resistant, and the like). In certain embodiments, the cancer is multiple myeloma, acute myeloid leukemia, melanoma, breast cancer, head or neck cancers, colon cancer, lung cancer, ovarian cancer, prostate cancer, and/or pancreatic cancer. In other embodiments, the compounds can be used to treat hyperproliferative diseases characterized by expression of functional Mcl-1 and/or Mcl-1 related proteins.

The invention also provides pharmaceutical compositions comprising the compounds of the invention in a pharmaceutically acceptable carrier.

The invention also provides kits comprising a compound of the invention and instructions for administering the compound to an animal. The kits may optionally contain other therapeutic agents, e.g., anticancer agents or apoptosis-modulating agents.

As described in the Examples, applying an integrated screening approach through combining high throughput and virtual screenings, de novo design and medicinal chemistry efforts conducted during the course of developing embodiments for the present invention, several novel chemical classes of small-molecules having a benzoic acid structure as Mcl-1 inhibitors were developed. For example, Compound 483

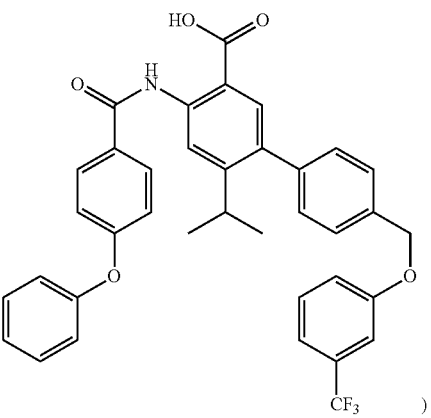

with benzoic acid scaffold was designed, synthesized and characterized as one of the most potent promising Mcl-1 inhibitors. 483 was shown to have a binding affinity of $K_i=7.0\pm2.0$ nM to Mcl-1, and high selectivity towards Bcl-2/Bcl-xL and Bcl-2 (Ki>1,000 nM). Moreover, 483 was shown to antagonize Mcl-1 function through binding the BH3 binding pocket of Mcl-1, to selectively kill Mcl-1 dependent cell lines, and synergize with ABT-263 to kill Panc-1 cells. Additional compounds shown to have high binding affinity for Mcl-1 include:

(380)

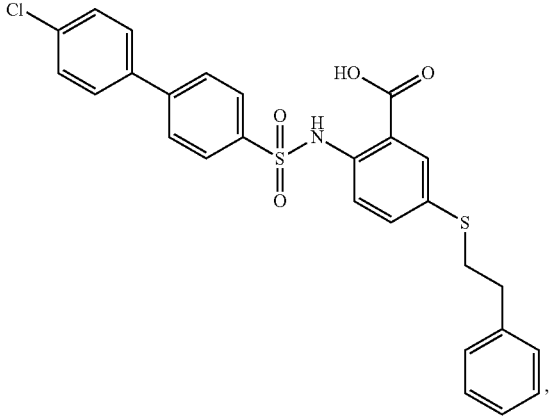

(376)
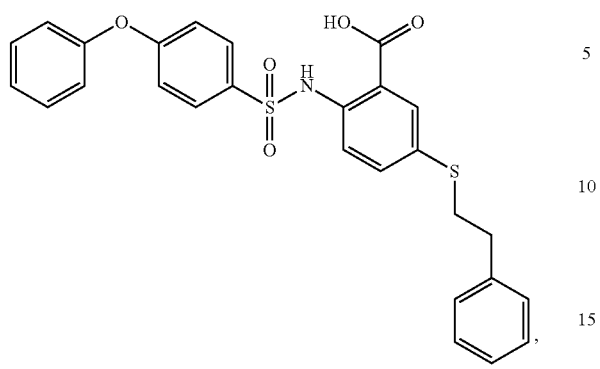
(471)
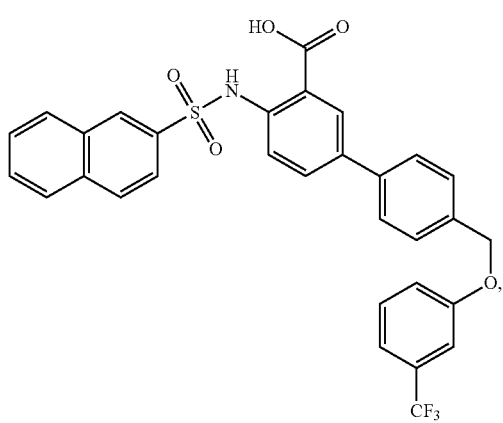
(475)
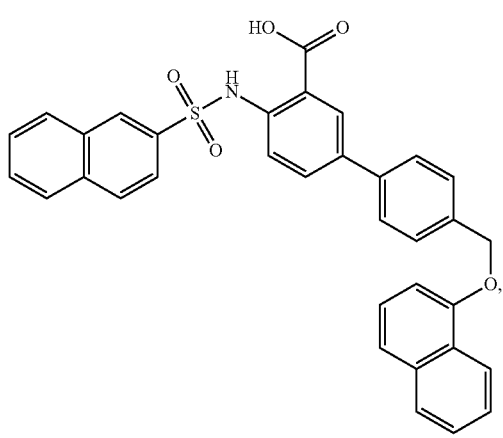
(476)
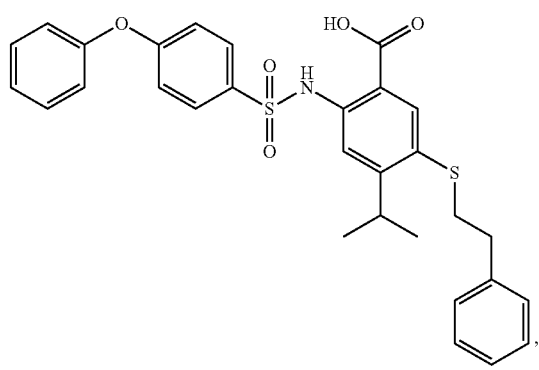
(474)
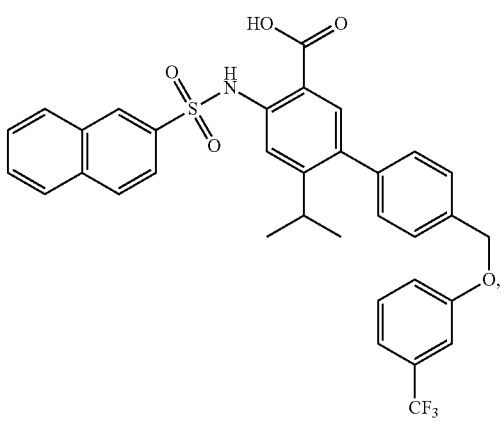
(477)
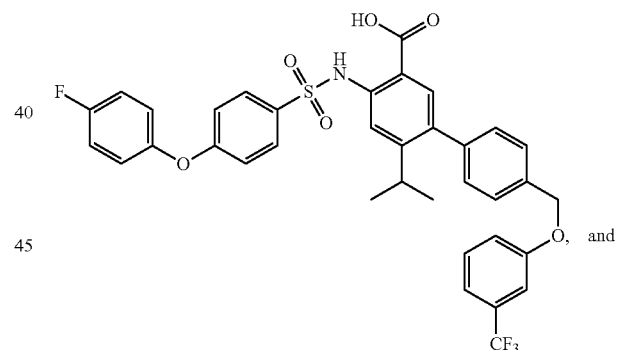
(480)
and
(487)
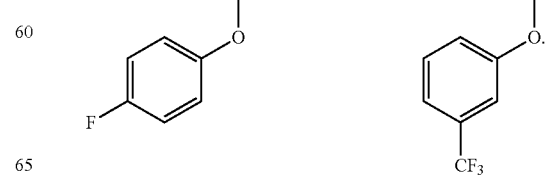

Accordingly, the present invention further provides methods for treating cancer through administration of therapeutic amounts of compound 483, 380, 376, 471, 475, 474, 476, 477, 480 and/or 487 to a subject suffering from cancer. The methods are not limited to a particular type of cancer. In some embodiments, the cancer is any cancer having Mcl-1 protein activity. In some embodiments, administration of compound 483, 380, 376, 471, 475, 474, 476, 477, 480 and/or 487 results in inhibition of Mcl-1 protein activity. In some embodiments, the administered compound 483, 380, 376, 471, 475, 474, 476, 477, 480 and/or 487 binds Mcl-1 protein within its BH3 groove. In some embodiments, the administered compound 483, 380, 376, 471, 475, 474, 476, 477, 480 and/or 487 inhibits cell growth and increases cellular apoptosis for cells having Mcl-1 activity. In some embodiments, the compound 483, 380, 376, 471, 475, 474, 476, 477, 480 and/or 487 are co-administered with one or more anticancer agents.

Moreover, the present invention provides methods for inhibiting Mcl-1 protein activity in cells through exposing such cells to one or more of the benzoic acid compounds of the present invention. In some embodiments, the benzoic acid compound is compound 483, 380, 376, 471, 475, 474, 476, 477, 480 and/or 487. In some embodiments, the benzoic acid compounds bind Mcl-1 protein thereby inhibiting the Mcl-1 protein activity. In some embodiments, the benzoic acid compounds bind the BH3 groove within the Mcl-1 protein.

BRIEF DESCRIPTION OF DRAWINGS

FIG. 5A-B: A) 483 induces Bax/Bak and Mcl-1 dependent cell death. Mouse Embryonic Fibroblasts (MEFs) were treated for 15 h with 483 and ABT263. Cell viability was assessed using propidium iodide staining detected with flow cytometry. (*) is p<0.05 B) 483 selectively induces cell death in Mcl-1 dependent Et-myc cell lines. Cells were treated for 15 h with increasing concentrations of (A) 483 and (B) ABT263. (C) Eµ-myc lymphoma cells overexpressing Mcl-1 were treated with 483 and the inactive analog 486. The percentage of dead cells was calculated using LIVE/DEAD fixable violet dead cell stain (VIVID) and detected with flow cytometry. (*) is p<0.001.

DEFINITIONS

Figure 1:
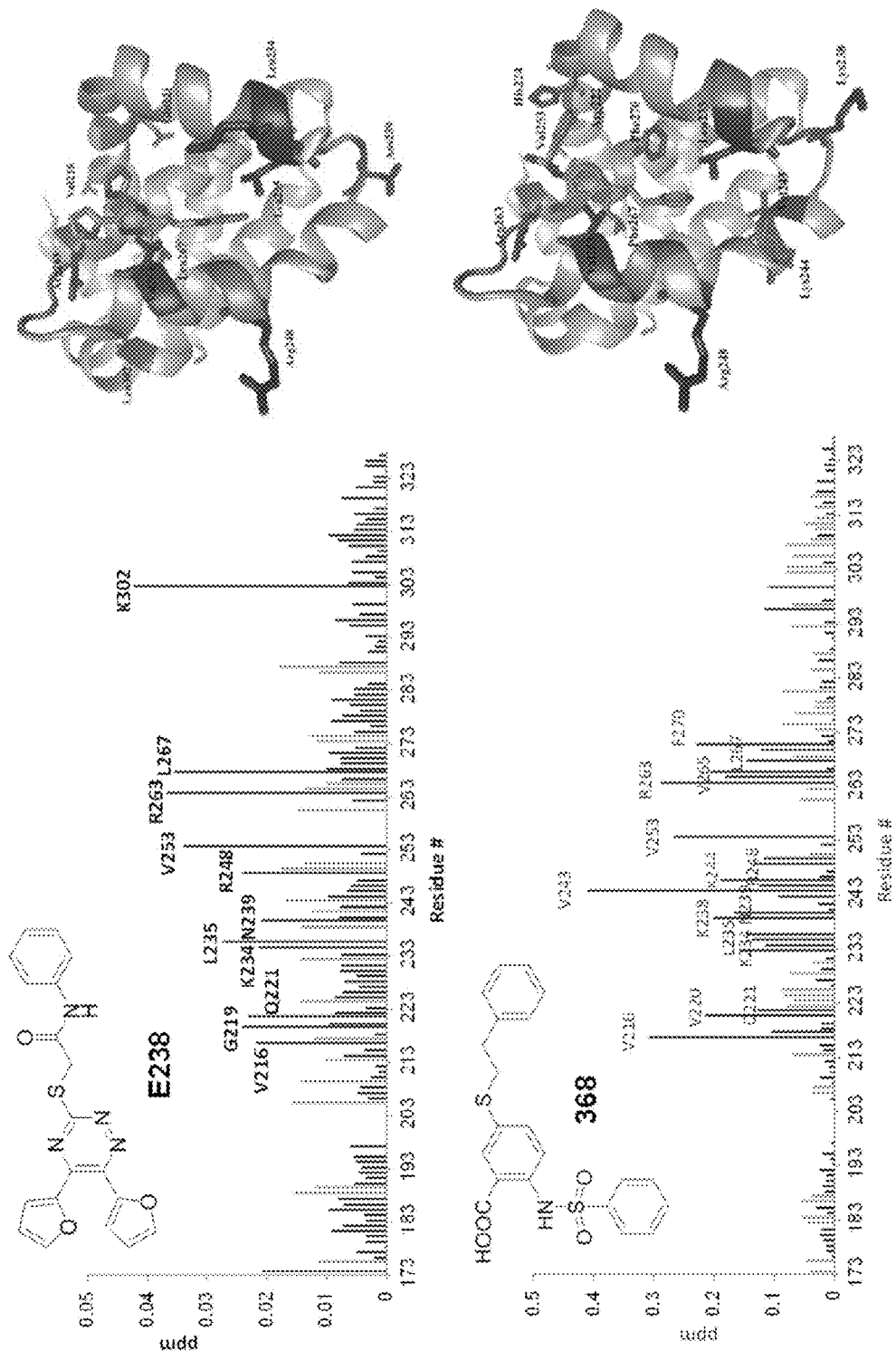
FIG. 1: HSQ NMR chemical shift perturbations and predicted binding poses of E238 and 368.

The term "anticancer agent" as used herein, refer to any therapeutic agents (e.g., chemotherapeutic compounds and/or molecular therapeutic compounds), antisense therapies, radiation therapies, or surgical interventions, used in the treatment of hyperproliferative diseases such as cancer (e.g., in mammals, e.g., in humans).

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol) or esters prepared by reaction of parent alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate (see, e.g., US Patent Application Publication No. US 2007/0249564 A1; herein incorporated by reference in its entirety).

The term "pharmaceutically acceptable salt" as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "solvate" as used herein, refers to the physical association of a compound of the invention with one or more solvent molecules, whether organic or inorganic. This physical association often includes hydrogen bonding. In certain instances, the solvate is capable of isolation, for example, when one or more solvate molecules are incorporated in the crystal lattice of the crystalline solid. "Solvate" encompasses both solution-phase and isolable solvates. Exemplary solvates include hydrates, ethanolates, and methanolates.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, in one embodiment, a therapeutically effective amount will refer to the amount of a therapeutic agent that decreases the rate of tumor growth, decreases tumor mass, decreases the number of metastases, increases time to tumor progression, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent (e.g., a benzoic acid compound of the invention), an animal or a cell within an animal more susceptible, or more responsive, to the biological effects (e.g., promotion or retardation of an aspect of cellular function including, but not limited to, cell division, cell growth, proliferation, invasion, angiogenesis, necrosis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least 300%, at least about 350%, at least about 400%, at least about 450%, or at least about 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, non-limiting examples of which include, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis.

The term "functional Mcl-1," as used herein, refers to wild-type Mcl-1 expressed at normal, high, or low levels and mutant Mcl-1 that retains at least about 5% of the activity of wild-type Mcl-1, e.g., at least about 10%, about 20%, about 30%, about 40%, about 50%, or more of wild-type activity.

The term "Mcl-1-related protein," as used herein, refers to proteins that have partial sequence homology (e.g., at least 5%, 10%, 25%, 50%, 75%, 85%, 95%, 99%, 99.999%) with Mcl-1, have tumor suppressor activity, and are inhibited by interaction with a compound of the present invention (e.g., a benzoic acid compound of the present invention).

The term "bioisostere" as used herein means a chemical moiety, group or molecule whose chemical and physical similarities to another group or molecule produce similar biological properties. The term bioisostere is generally understood to refer to a portion of a molecule, rather than to the entire molecule. A bioisostere of a compound may produce a similarity in a biologically important parameter. A bioisostere of a compound may be useful to attenuate toxicity, modify activity, and/or alter the metabolism of the compound. The following parameters may be considered in developing a bioisosteric replacement: size, shape, electronic distribution, permeability, lipid solubility, water solubility, $pK_a$, chemical reactivity, and hydrogen bonding capacity. In some embodiments, the bioisostere is a carboxylic acid bioisostere.

As used herein, the term "iPR" refers to an isopropyl moiety

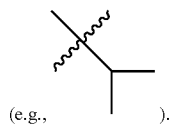

(e.g., ).

The term "hyperproliferative disease," as used herein, refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

The term "neoplastic disease," as used herein, refers to any abnormal growth of cells being either benign (non-cancerous) or malignant (cancerous).

The term "normal cell," as used herein, refers to a cell that is not undergoing abnormal growth or division. Normal cells are non-cancerous and are not part of any hyperproliferative disease or disorder.

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995.

DETAILED DESCRIPTION OF THE INVENTION

Myeloid cell leukemia-1 (Mcl-1) is a potent anti-apoptotic protein, belonging to the prosurvival Bcl-2 subfamily and its role is emerging as a critical survival factor in a broad range of human cancers (see, e.g., Day C L, et al., J Biol Chem. 2005; 280:4738-44; Day C L, et al., J Mol Biol. 2008; 380:958-71; each herein incorporated by reference in its entirety). Functional studies have confirmed that Mcl-1 is capable of blocking apoptosis induced by various apoptotic stimuli, including chemotherapy and radiation (see, e.g., Zhou P, et al., Blood. 1997; 89:630-43; herein incorporated by reference in its entirety). Mcl-1 is highly up-regulated in a variety of human cancers and is associated with resistance to chemotherapeutic agents (see, e.g., Miyamoto Y, et al., Oncology. 1999; 56:73-82; Schniewind B, et al., Int J Cancer. 2004; 109:182-8; Ren L N, et al., Biochem Biophys Res Commun. 2009; 386:35-9; Wei S H, et al., Cancer Chemother Pharmacol. 2008; 62:1055-64; Guoan X, et al., Surgery. 2010; 147:553-61; Huang S, et al., Cancer Res. 2008; 68:2944-51; each herein incorporated by reference in its entirety). Mcl-1 is an important survival factor and down-regulation of Mcl-1 enhances the induction of apoptosis and chemosensitivity to Gemcitabine, radiation and ABT-737 (see, e.g., Wei S H, et al., Cancer Chemother Pharmacol. 2008; 62:1055-64; Guoan X, et al., Surgery. 2010; 147:553-61; Huang S, et al., Cancer Res. 2008; 68:2944-51; each herein incorporated by reference in its entirety). Thus, Mcl-1 represents a very attractive molecular target for developing a new class of cancer therapy for treatment of human cancers by overcoming resistance to chemotherapeutic agents.

Potent small molecule inhibitors of Bcl-2 subfamily include the Bad-like BH3 mimetics (see, e.g., Oltersdorf T, et al., Nature. 2005; 435:677-81; Tse C, et al., Cancer Res. 2008; 68:3421-8; each herein incorporated by reference in its entirety). ABT-737, one of these mimetics, binds with high affinity ($K_i \leq 1$ nM) to Bcl-2, Bcl-$x_L$ and Bcl-w but fails to bind to Mcl-1 (see, e.g., Oltersdorf T, et al., Nature. 2005; 435:677-81; herein incorporated by reference in its entirety). Several studies have shown that resistance to ABT-737 is linked to high expression levels of Mcl-1 and in many instances this resistance can be overcome by treatment with agents that down-regulate, destabilize, or inactivate Mcl-1 (see, e.g., van Delft M F, et al., Cancer Cell. 2006; 10:389-99; Chen S, et al., Cancer Res. 2007; 67:782-91; each herein incorporated by reference in its entirety). It was recently shown that knockdown of Mcl-1 sensitizes human PC cancer cells to ABT-737-induced apoptosis, indicating that Mcl-1 is a relevant therapeutic target in these cancer cells (see, e.g., Huang S, et al., Cancer Res. 2008; 68:2944-51; herein incorporated by reference in its entirety).

High throughput screen (HTS) approach is a known strategy for identification of potential lead compounds for further development (see, e.g., Macarron, R., et al., Nat Rev Drug Discov 2011, 10, 188-95). Employing de-novo structure-based drug-design, experiments conducted during the course of developing embodiments for the present invention designed a new class of potent small-molecule Mcl-1 inhibitors based on the initial lead compound discovered by high-throughput screening: (see, e.g., Du, Y., et al., Assay and drug development technologies 9, 382-393). Analyzing the binding model of this compound with Mcl-1 through computational docking supported by HSQC NMR studies, and using the structural information, a class of small-molecule inhibitors of Mcl-1 were designed and optimized using a 2,4,5 substituted benzoic acid as a scaffold to reproduce the key interactions with Mcl-1 such as the conserved hydrogen bond between the aspartate in pro-apoptotic proteins and Arg263 in Mcl-1 and hydrophobic interactions by the highly-conserved leucine residue of the pro-apoptotic proteins (Bim, Noxa and Puma). Several co-crystal structures of this class inhibitors in complex with Mcl-1 have provided a basis for their further optimization which ultimately led to the discovery of ligands with low-nanomolar potency ($K_i$=7 nM). These compounds bind in the canonical BH3 binding groove. Interestingly, depending on the particular substitution pattern in the core scaffold, a "flip" binding mode was observed where the substituents bind in a reverse orientation, confirmed by X-ray crystallography. The most potent compounds have excellent metabolic stability and promising cell activity.

Accordingly, the present invention relates to compounds which function as inhibitors of Mcl-1 proteins. By inhibiting the activity of Mcl-1, these compounds sensitize cells to inducers of apoptosis and/or cell cycle arrest and, in some instances, themselves induce apoptosis and/or cell cycle arrest. Therefore, the invention relates to methods of sensitizing cells to inducers of apoptosis and/or cell cycle arrest and to methods of inducing apoptosis and/or cell cycle arrest in cells, comprising contacting the cells with a compound of the invention alone or in combination with additional agent(s), e.g., an inducer of apoptosis or a cell cycle disrupter.

The invention further relates to methods of treating, ameliorating, or preventing disorders in a patient, such as those that are responsive to induction of apoptosis, comprising administering to the patient a compound of the invention and additional agent(s), e.g., an inducer of apoptosis. Such disorders include those characterized by a dysregulation of apoptosis and those characterized by the proliferation of cells expressing functional Mcl-1 proteins (e.g., pancreatic cancer).

In a particular embodiment, benzoic acid compounds encompassed within Formula I are provided

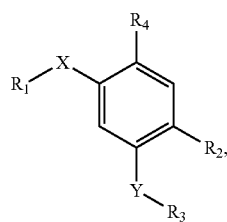

including pharmaceutically acceptable salts, solvates, and/or prodrugs thereof.

Formula I is not limited to a particular chemical moiety for R1, R2, R3, R4, X or Y. In some embodiments, the particular chemical moiety for R1, R2, R3, R4, X or Y independently include any chemical moiety that permits the resulting compound to bind with a Mcl-1 protein. In some embodiments, the particular chemical moiety for R1, R2, R3, R4, X or Y independently include any chemical moiety that permits the resulting compound to bind the BH3 binding pocket of Mcl-1.

In some embodiments, X is a linker. In some embodiments, X is

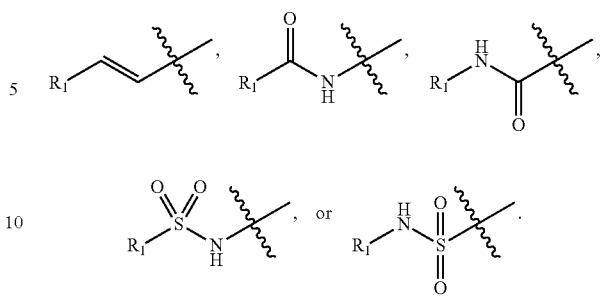

In some embodiments, X is absent.

In some embodiments, R1 is a substituted or non-substituted moiety comprising H, C, N, O, and/or S. In some embodiments, R1 is selected from

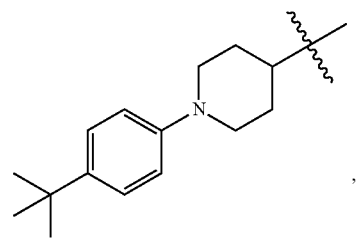

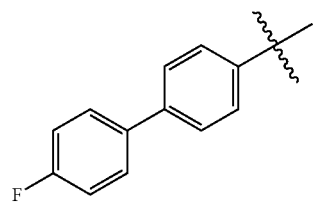

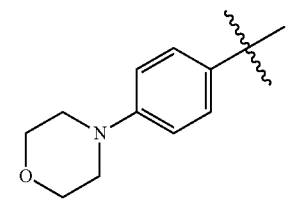

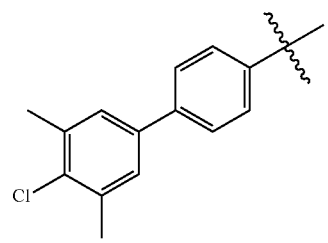

, NH2, OH, H,

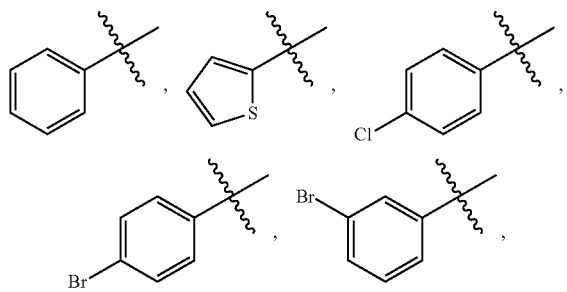

-continued
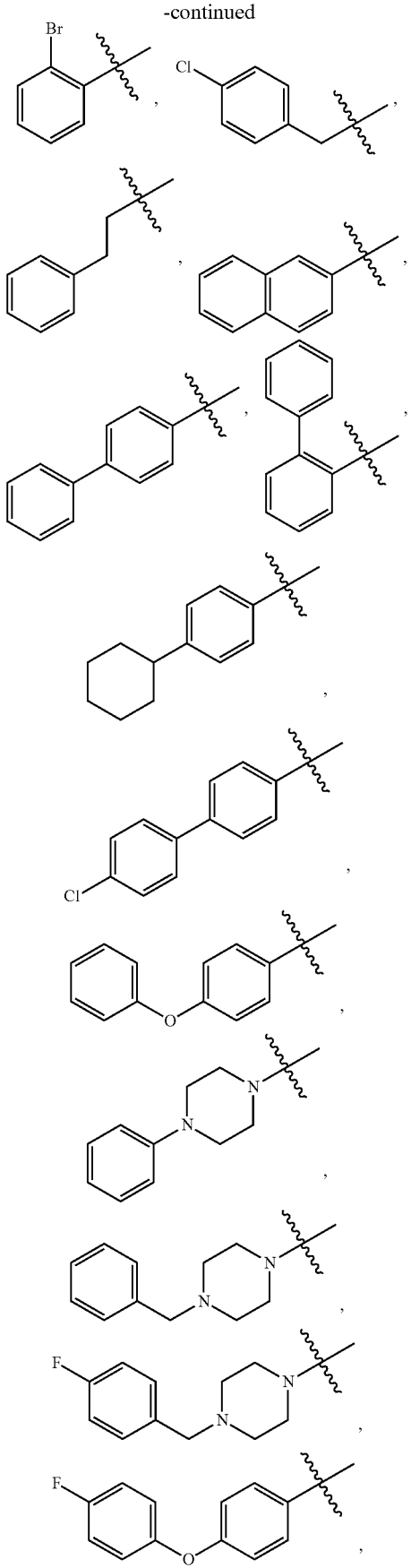
-continued
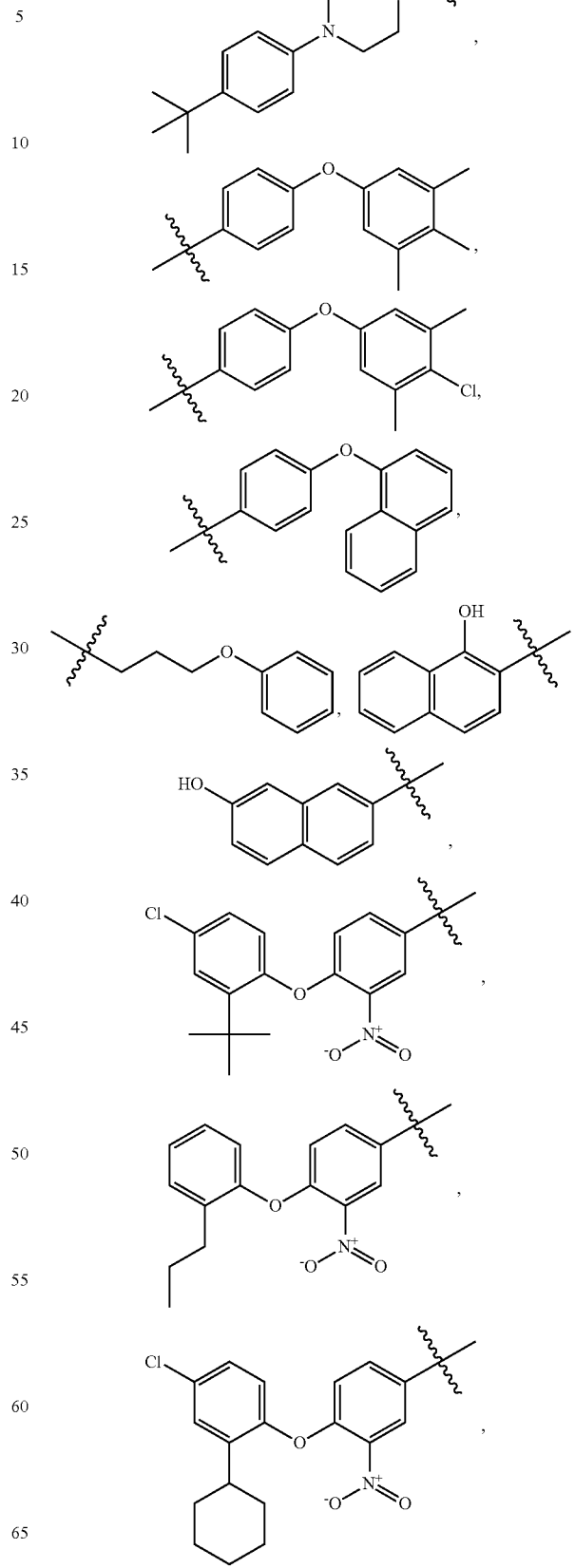

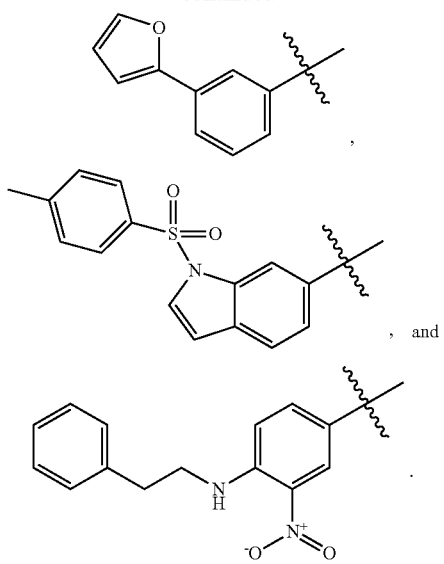
In some embodiments, R2 is a substituted or non-substituted moiety comprising H, C, N, O, and/or S. In some embodiments, R2 is selected from H,
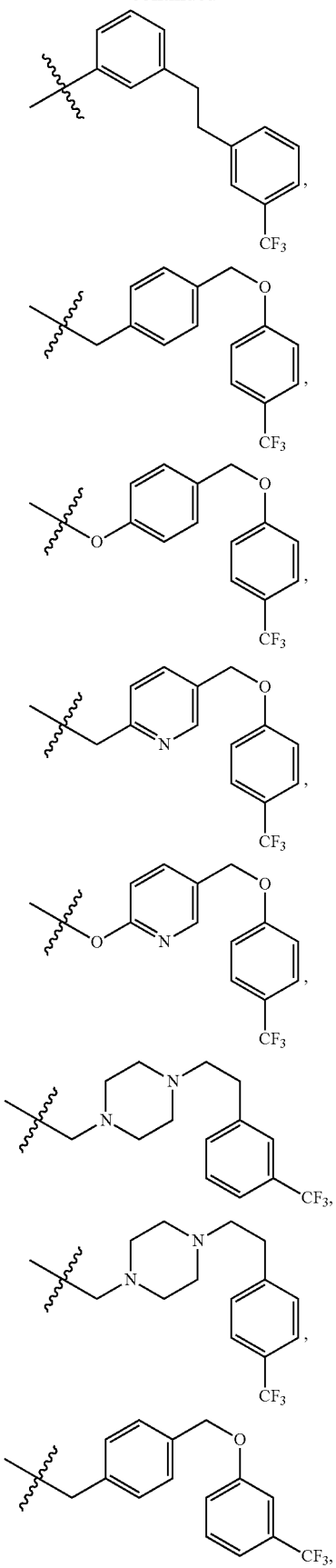

51
-continued
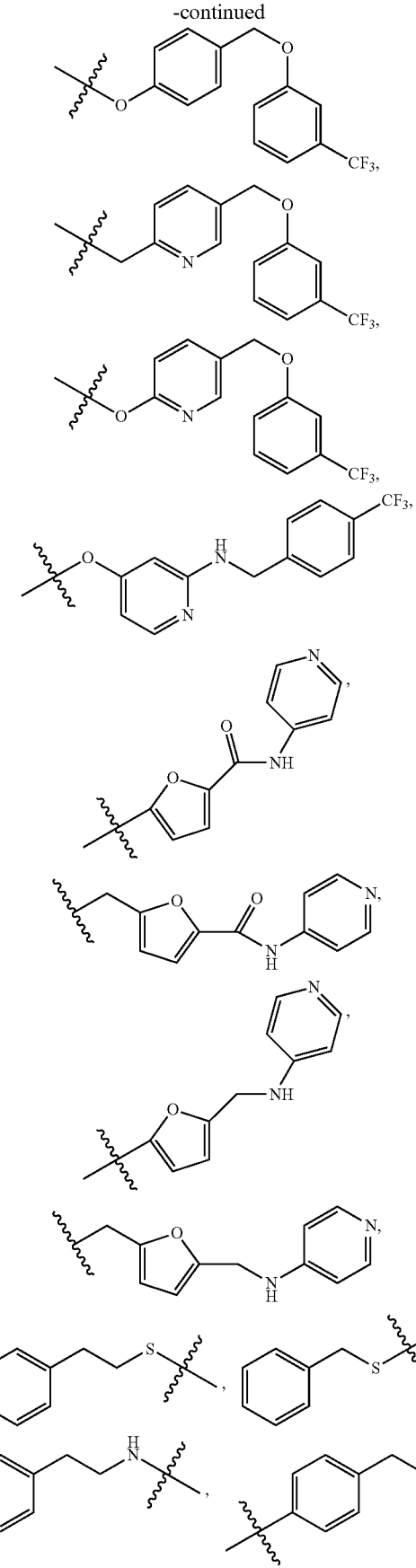
52
-continued
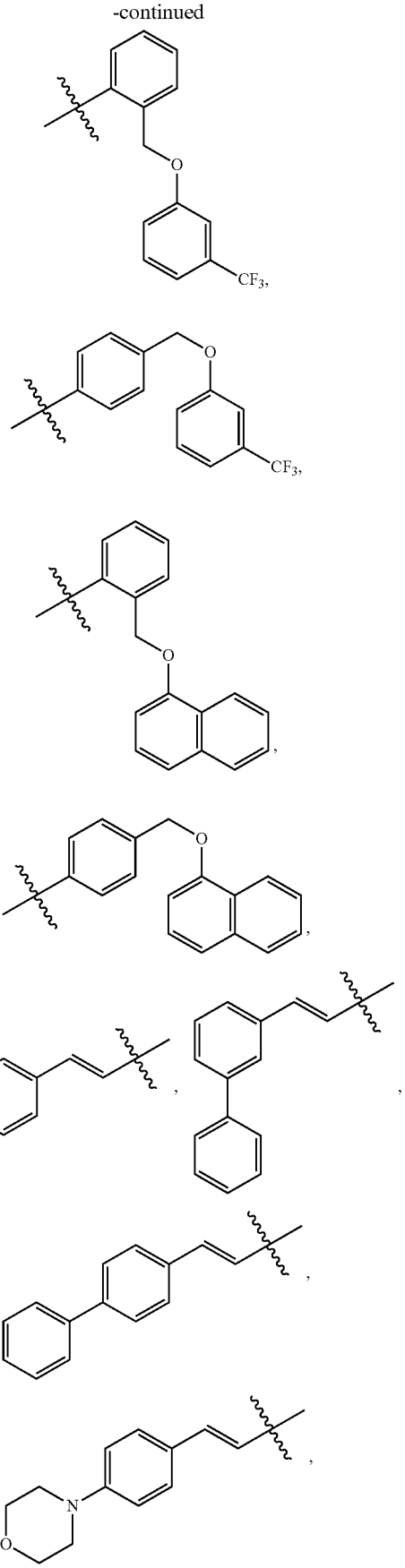

-continued
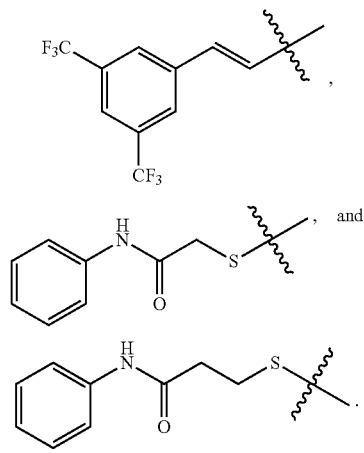
, and
In some embodiments, Y-R3 is absent. In some embodiments, R3 is absent from Y-R3 (e.g., in some embodiments Y-R3 is Y) and Y can be selected from
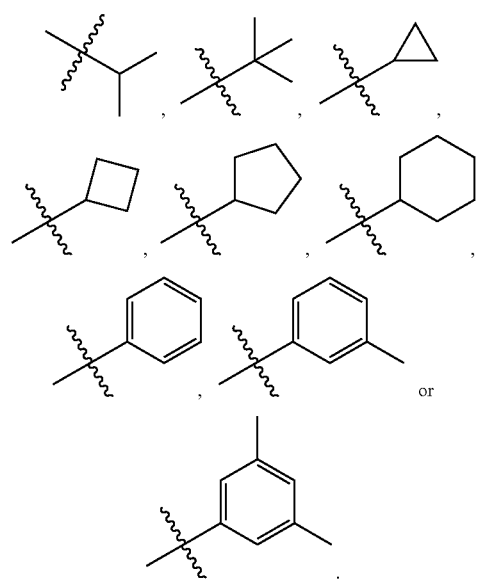
or
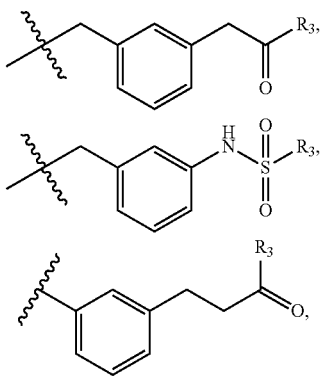
In some embodiments Y is selected from
-continued
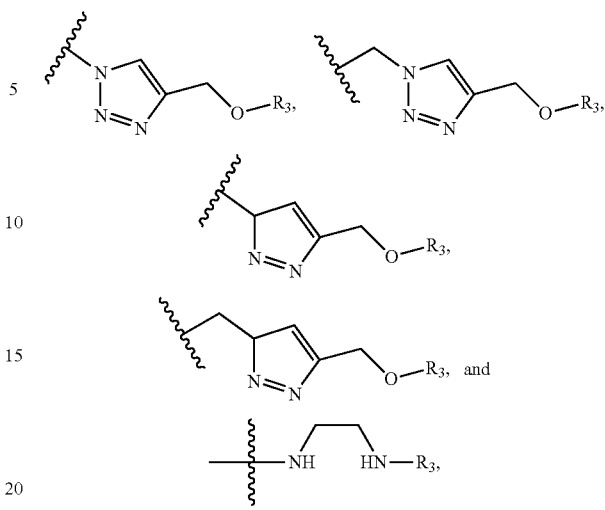
and R3 is selected from the group consisting of hydrogen,
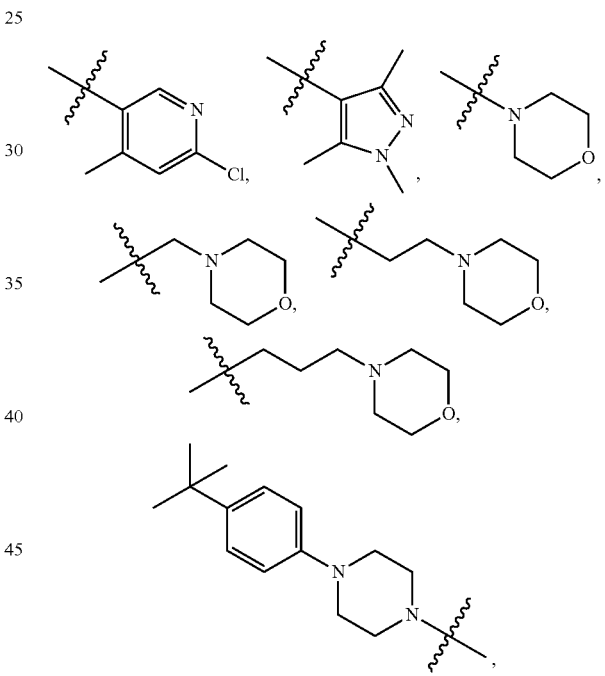
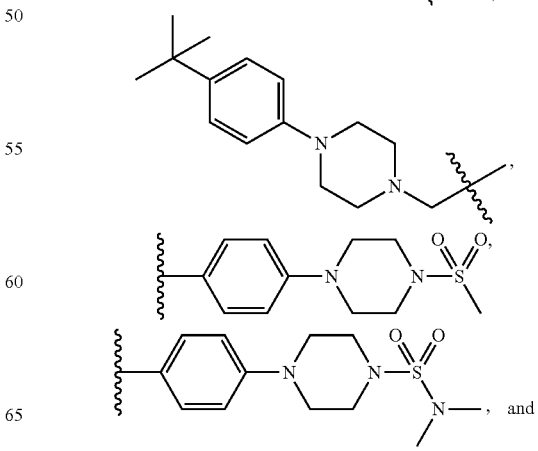
, and -continued

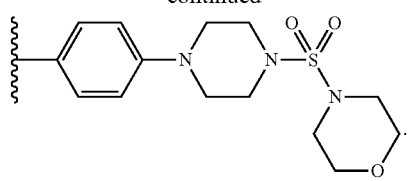

In some embodiments, R4 is an acid moiety. In some embodiments, R4 is an ester moiety. In some embodiments, R4 is hydrogen. In some embodiments, R4 is CH$_3$. In some embodiments, R4 is OH. In some embodiments, R4 is a carboxylic acid bioisostere moiety. In some embodiments, R4 is selected from H, OH, OCH$_3$, OCH$_2$CH$_3$, COOH, COOCH$_3$, COOCH$_2$CH$_3$,

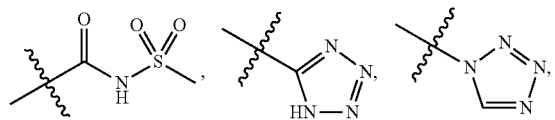

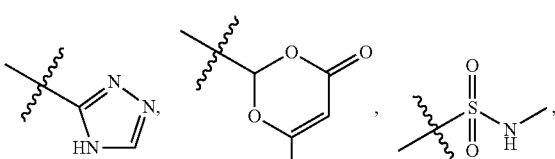

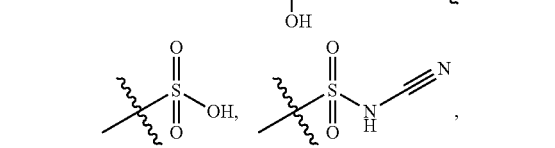

(wherein X, Y, Z are independently N, C or CO),

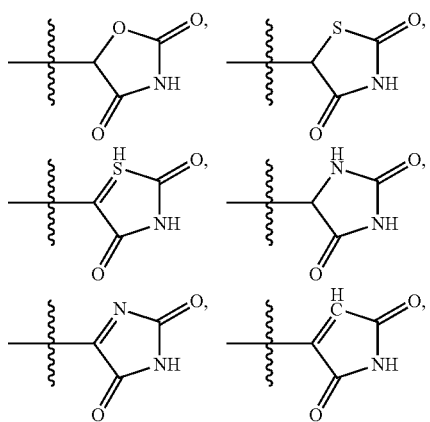

-continued

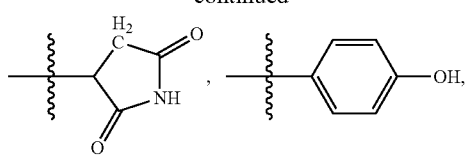

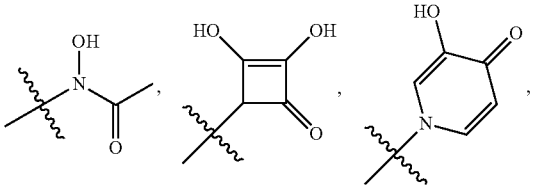

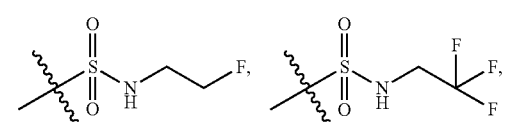

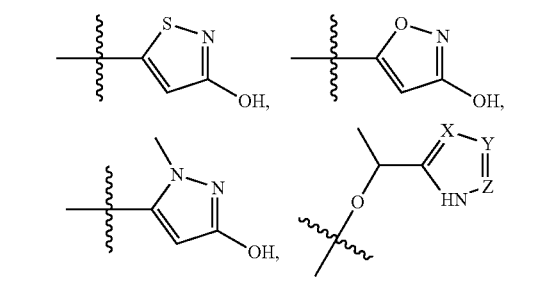

Table 1 (see, Examples) show binding affinities (K$_i$ values) and inhibition against Mcl-1 for various compounds encompassed within Formula I. In some embodiments, the following compounds are contemplated for Formula I:

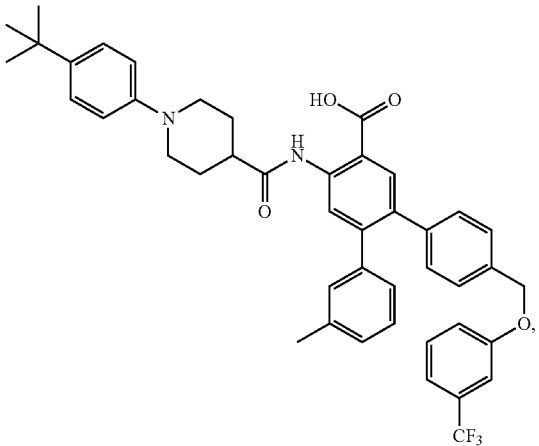

57
-continued
58
-continued
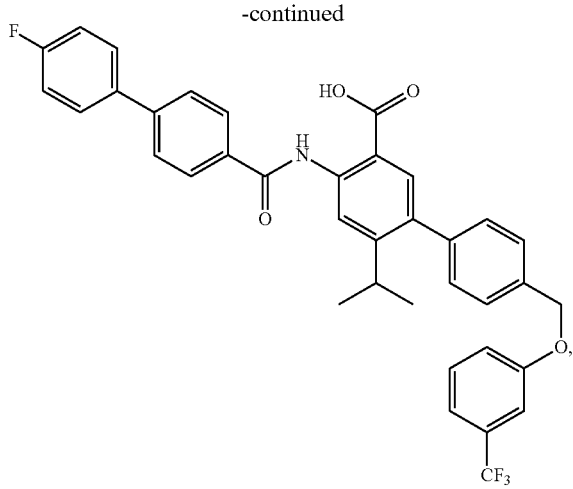
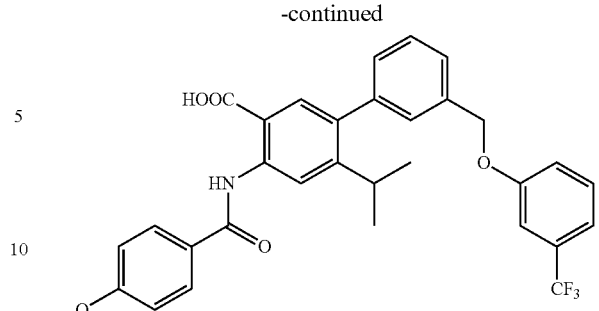
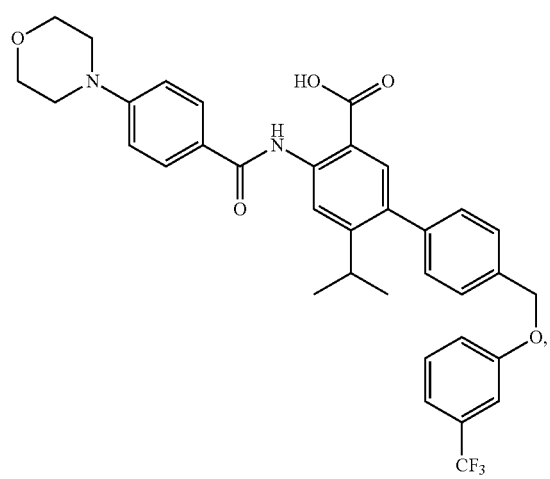
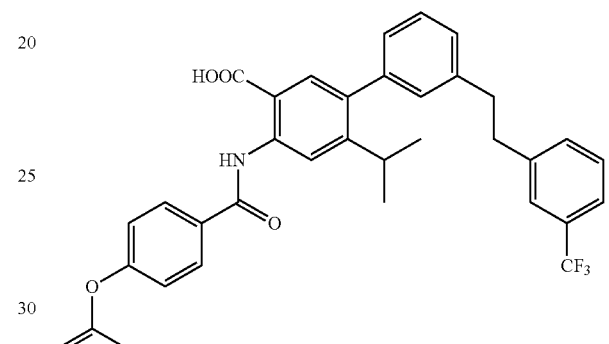
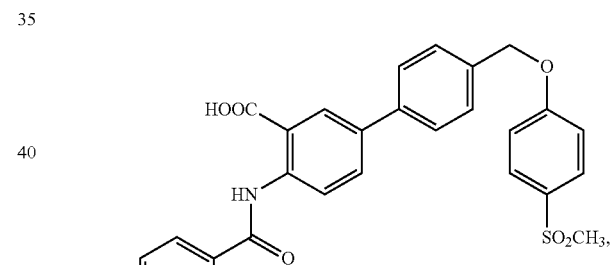
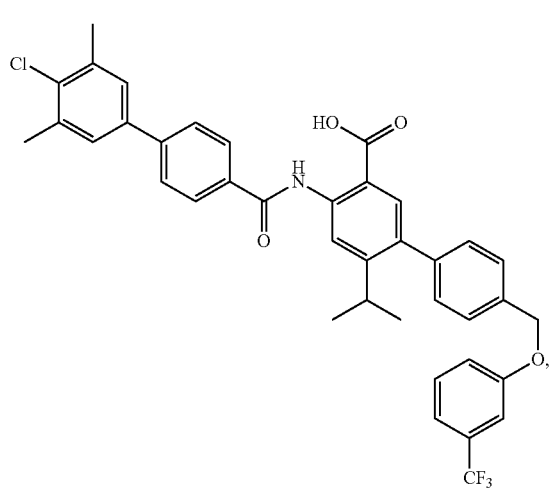
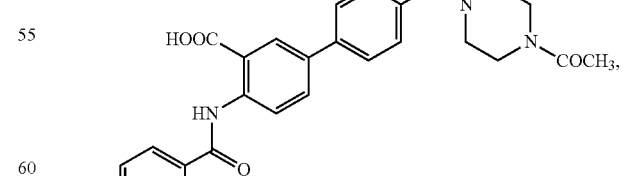

59
-continued
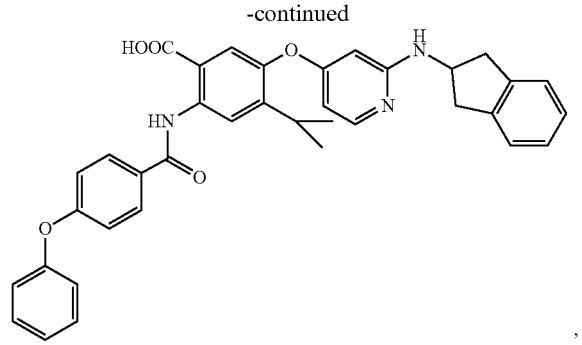
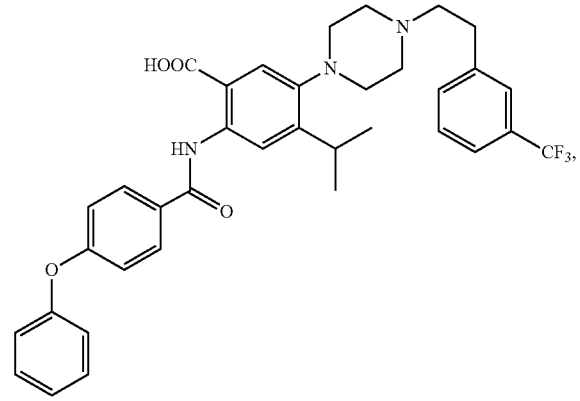
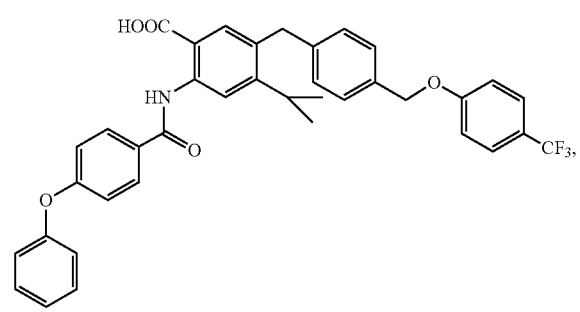
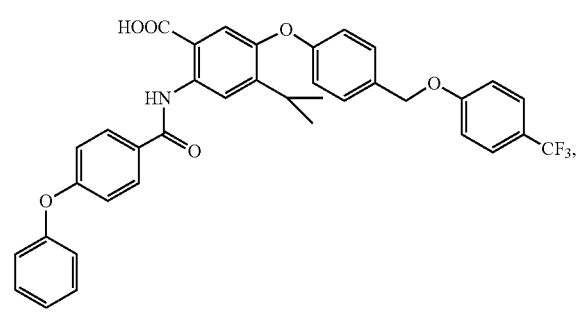
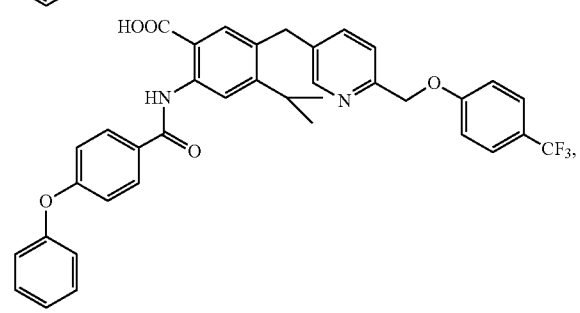
60
-continued
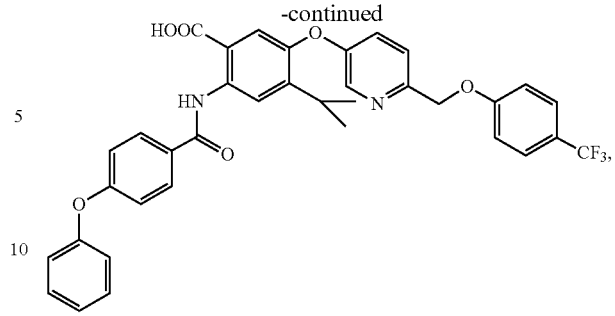
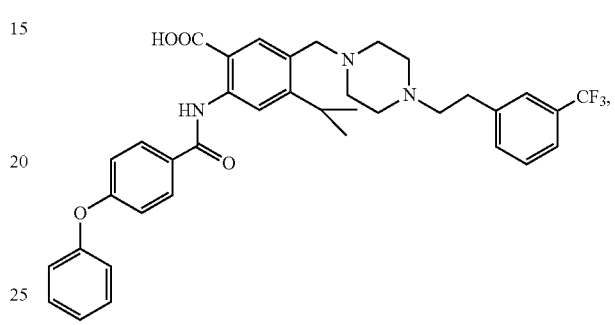
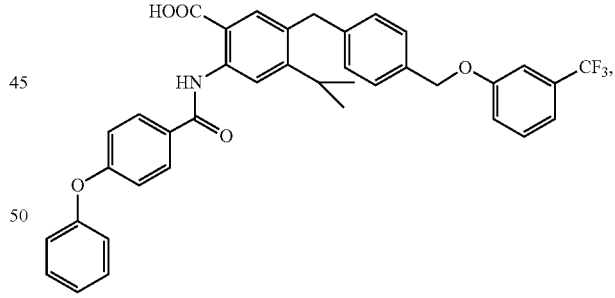
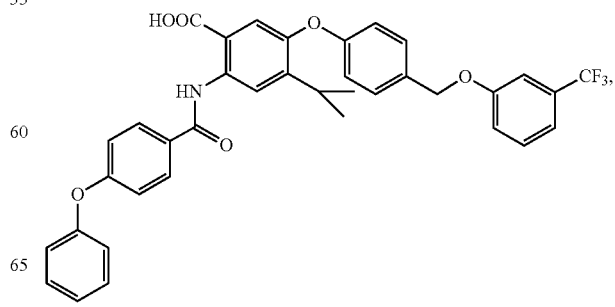

61
-continued
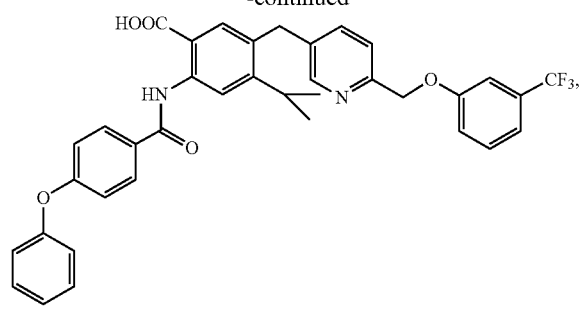
62
-continued
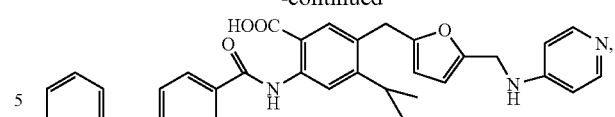
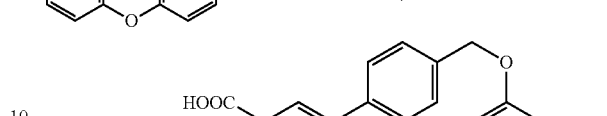
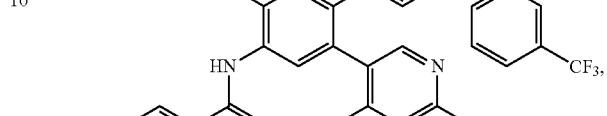
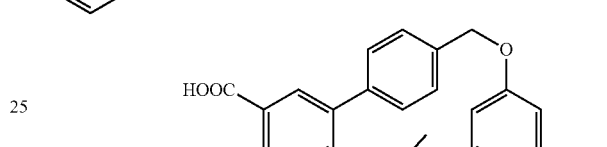
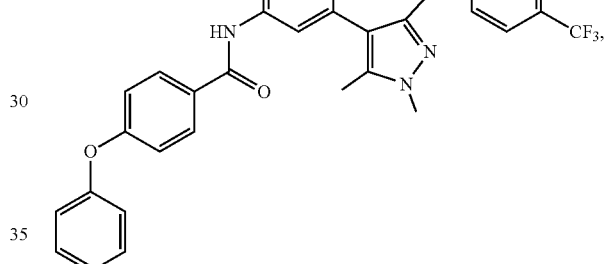
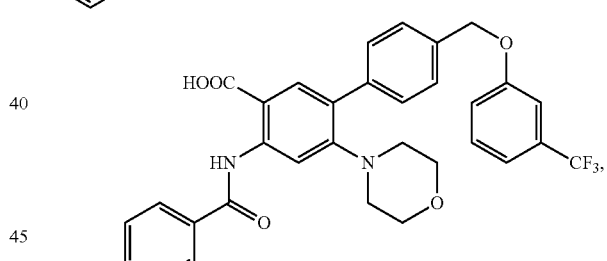
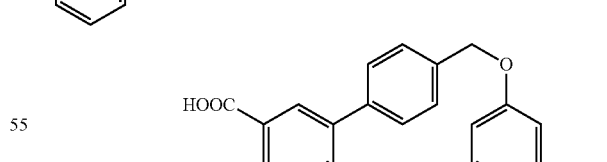
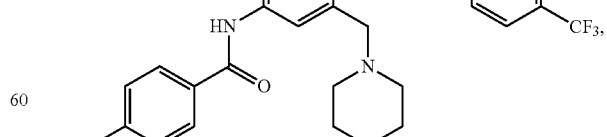
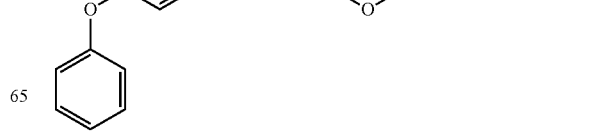

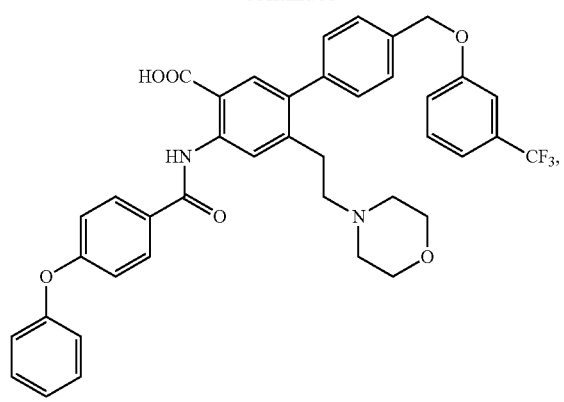
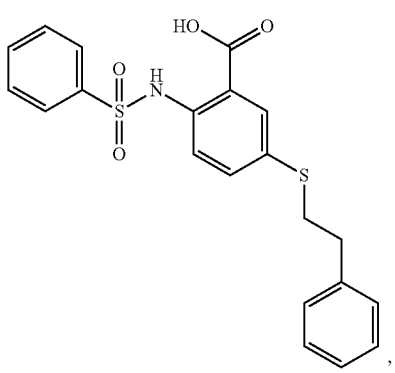
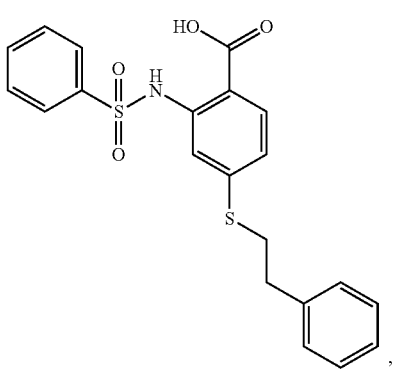
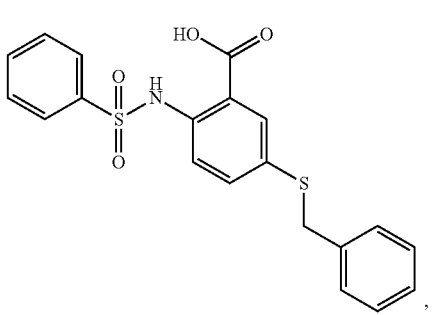
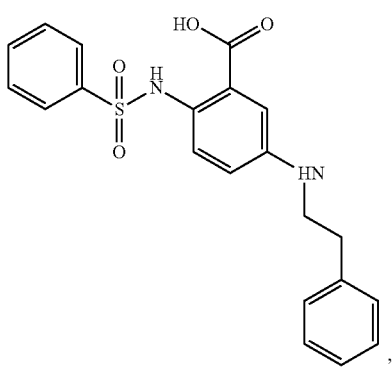
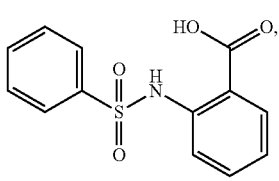

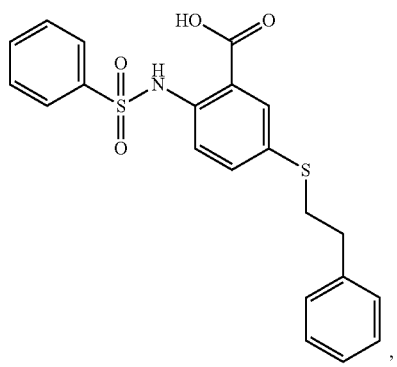
(368)
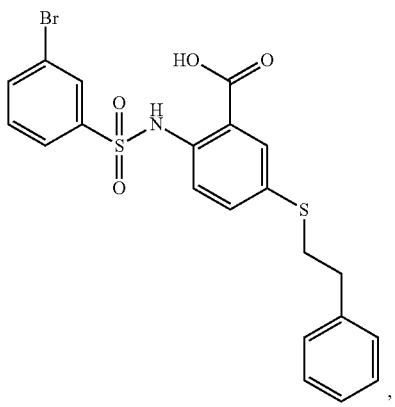
(384)
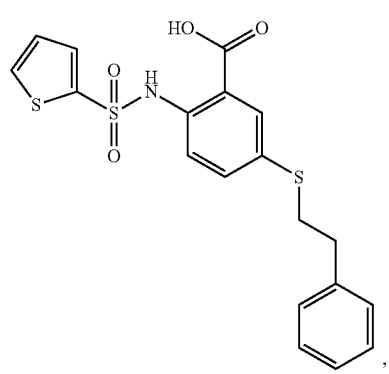
(387)
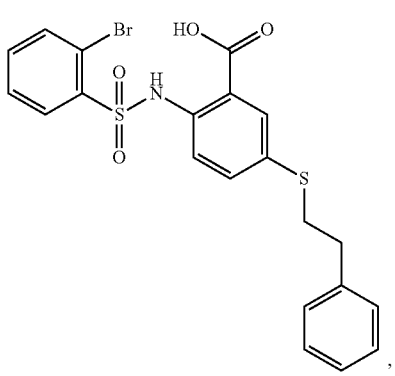
(386)
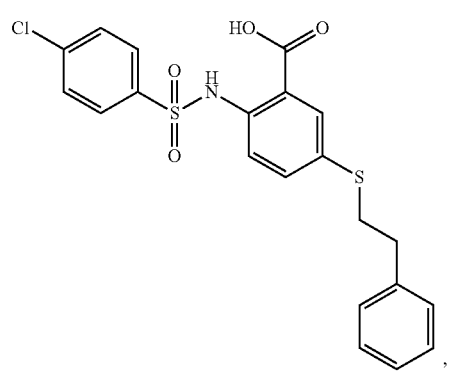
(381)
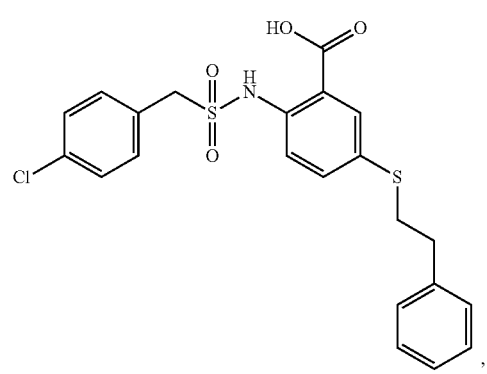
(398)
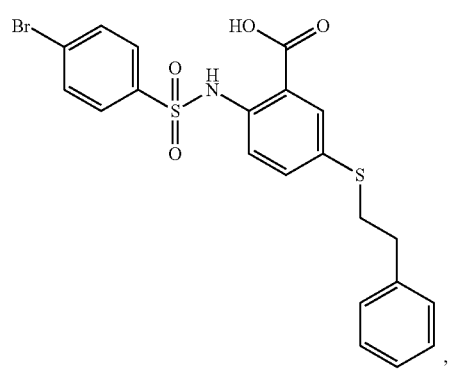
(389)
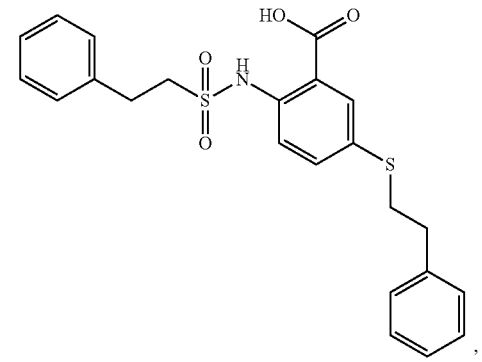
(443)

(454)
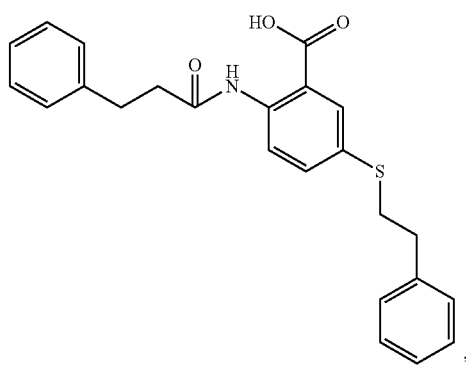
(382)
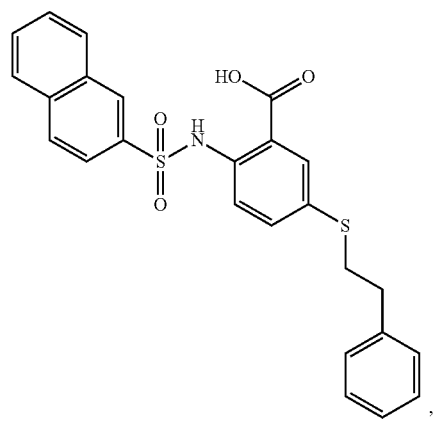
(378)
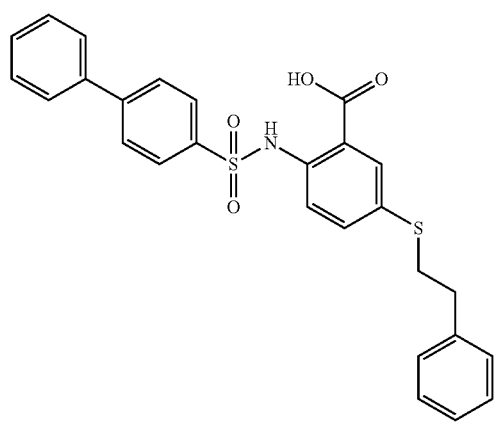
(458)
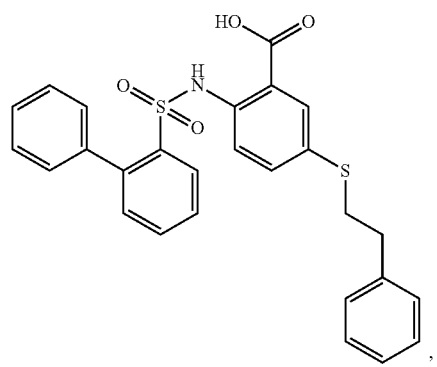
(418)
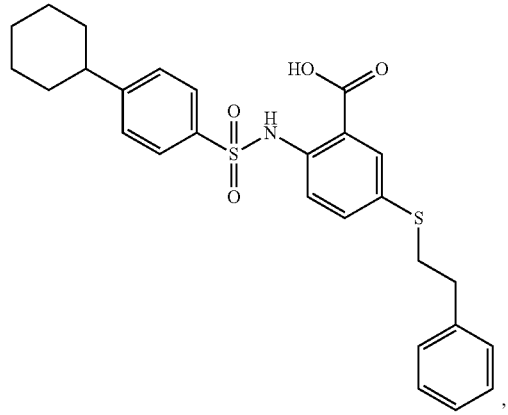
(380)
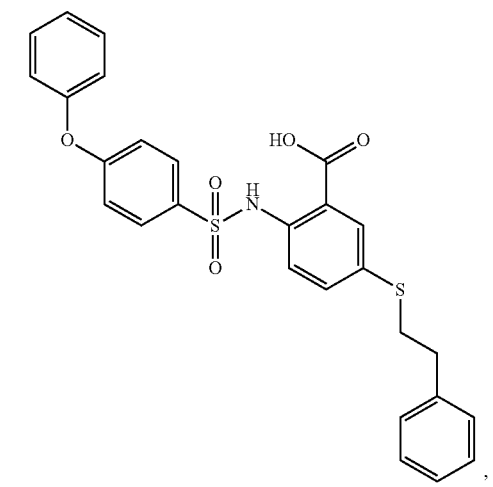
(376)

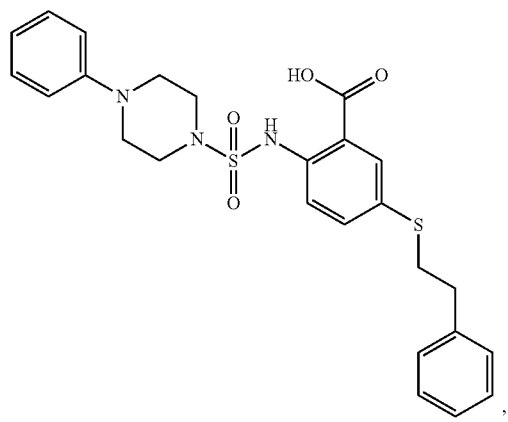
(396)
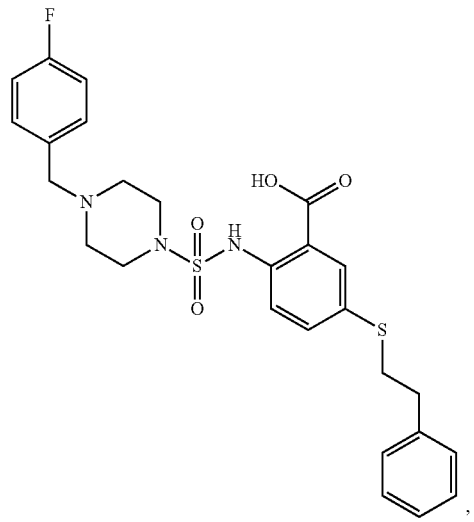
(462)
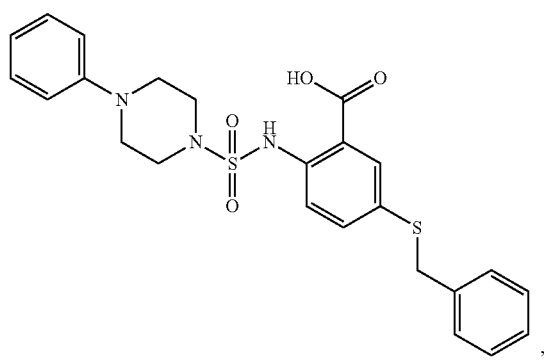
(456)
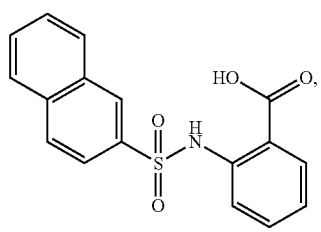
(453)
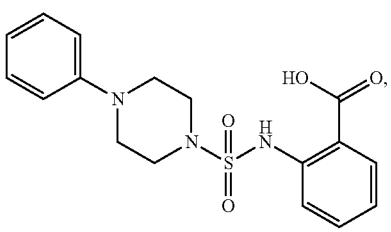
(460)
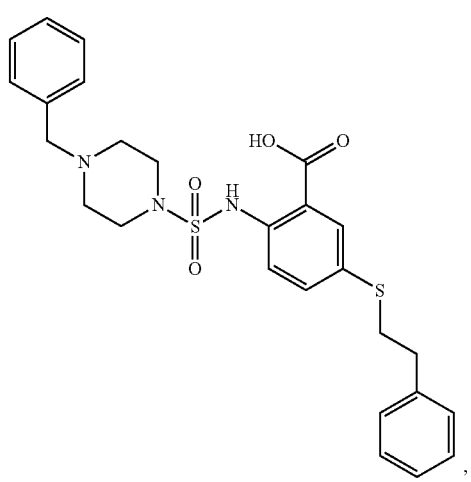
(414)
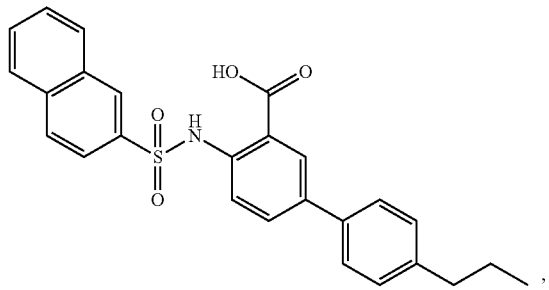
(466)

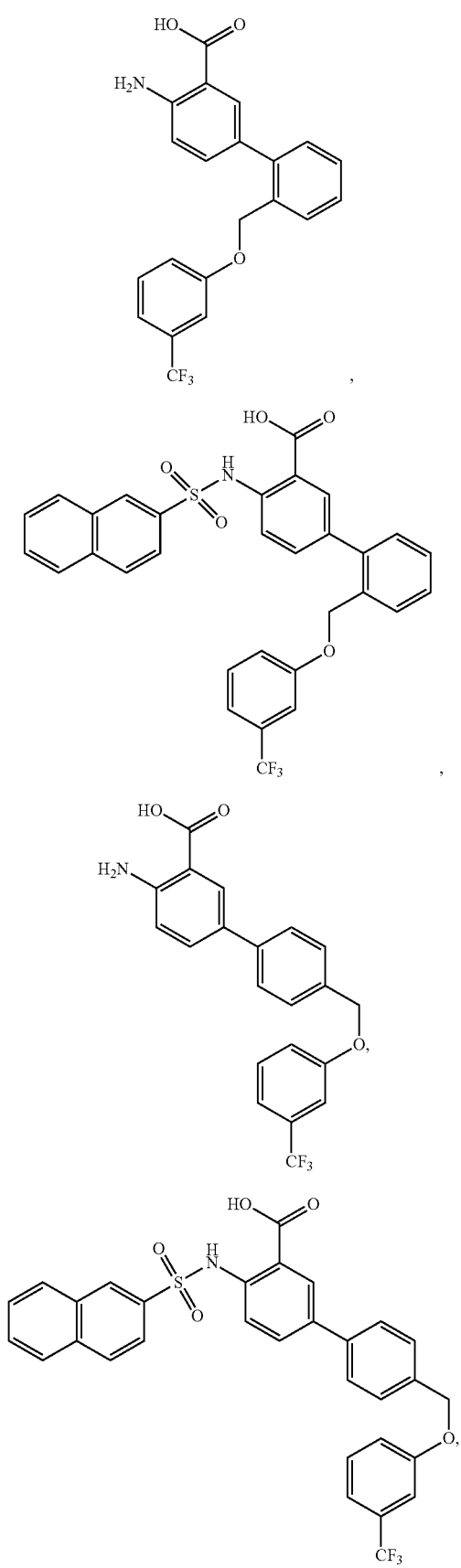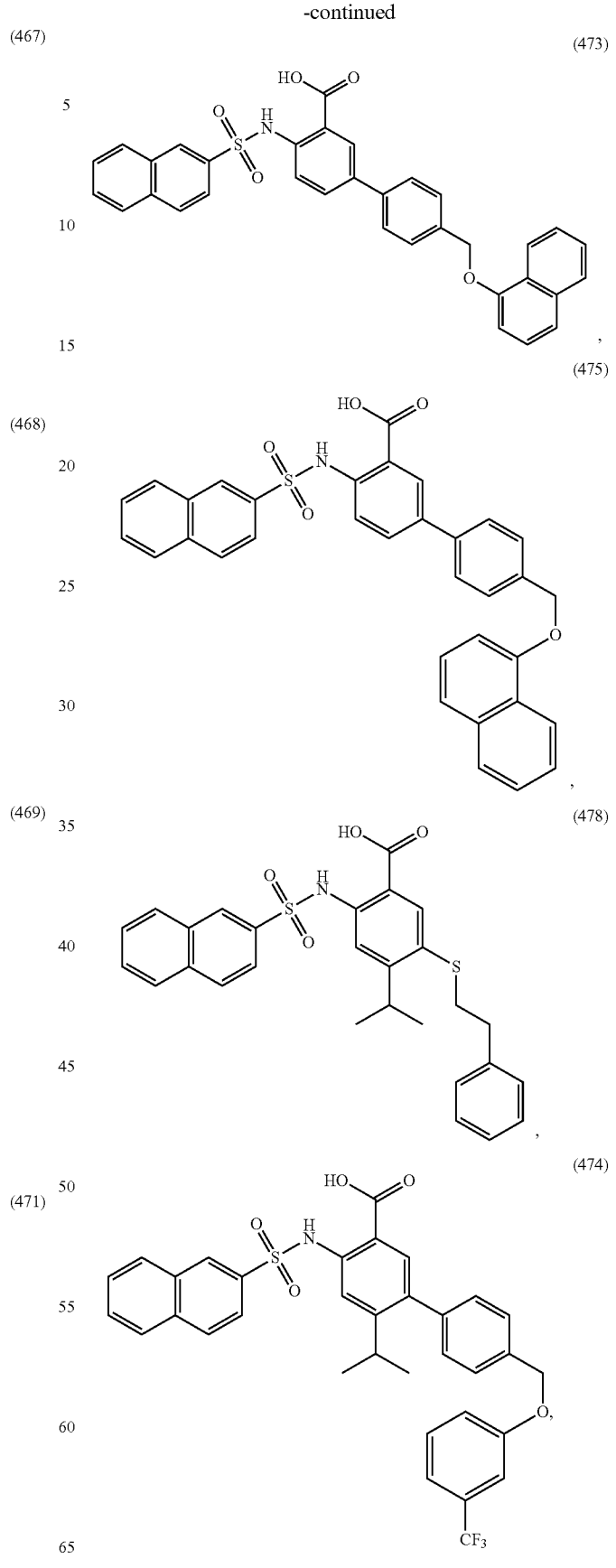

-continued
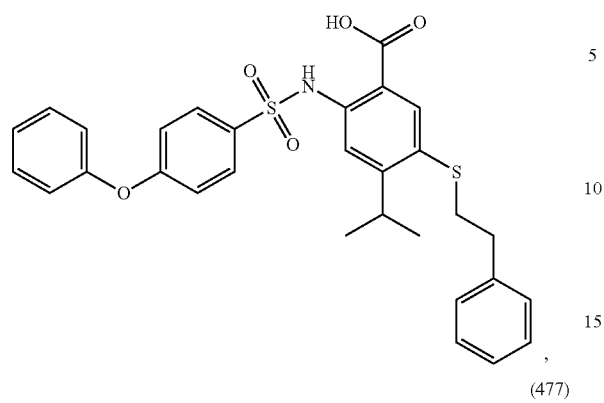
(476)
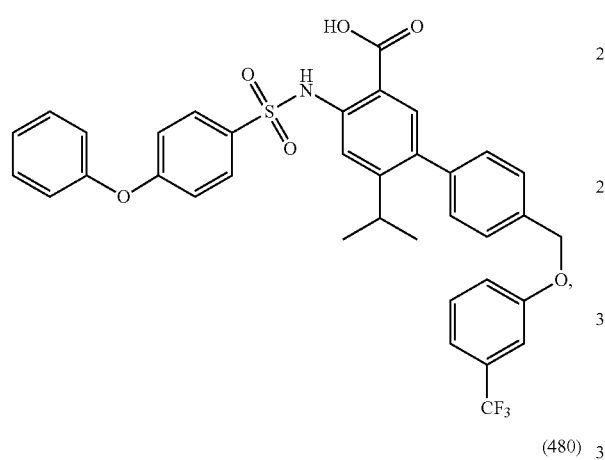
(477)
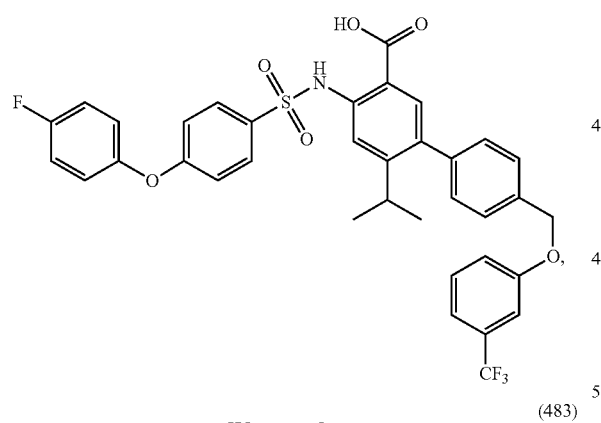
(480)
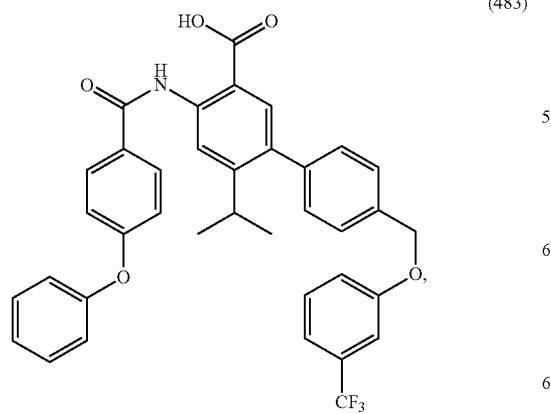
(483)
-continued
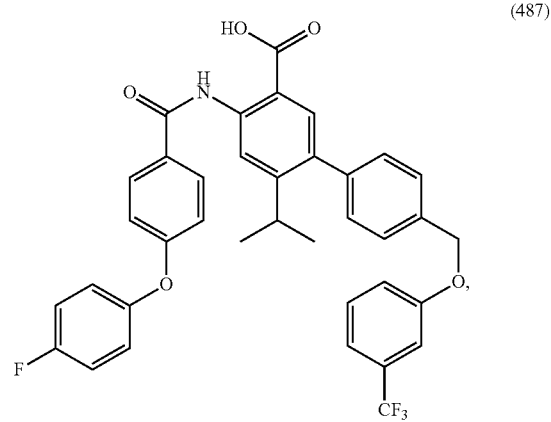 [SMILES: CC(C)c1cc(NC(=O)c2ccc(Oc3ccc(F)cc3)cc2)c(C(=O)O)cc1-c1ccc(COc2cccc(C(F)(F)F)c2)cc1]
(487)
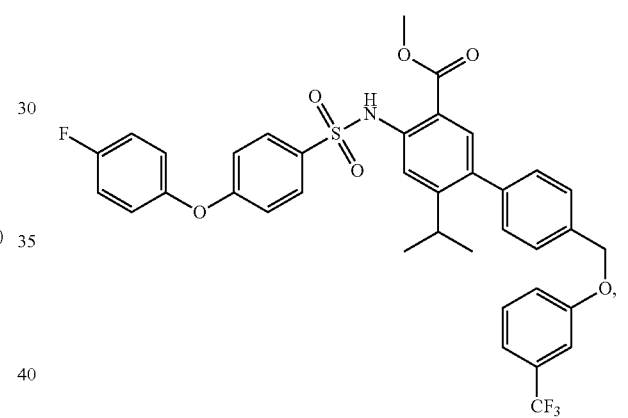
(481)
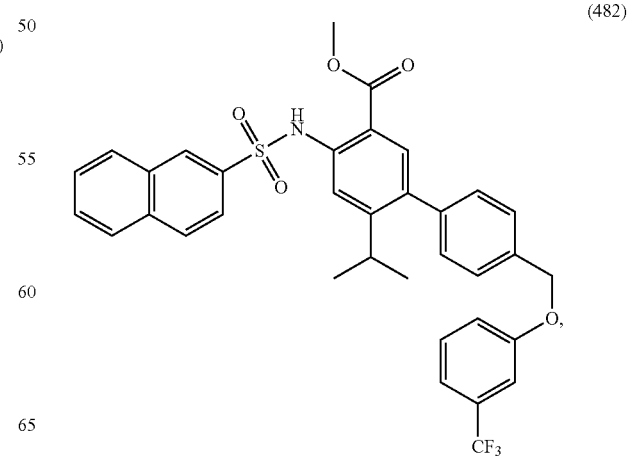
(482)

(486) 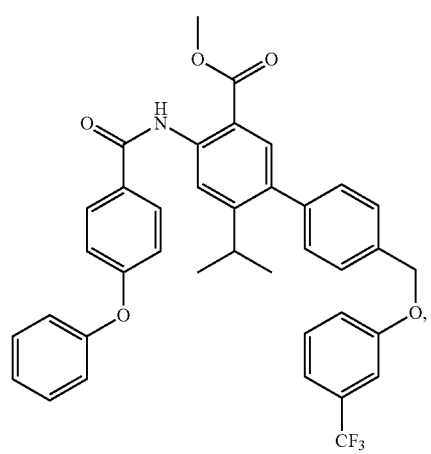
(460) 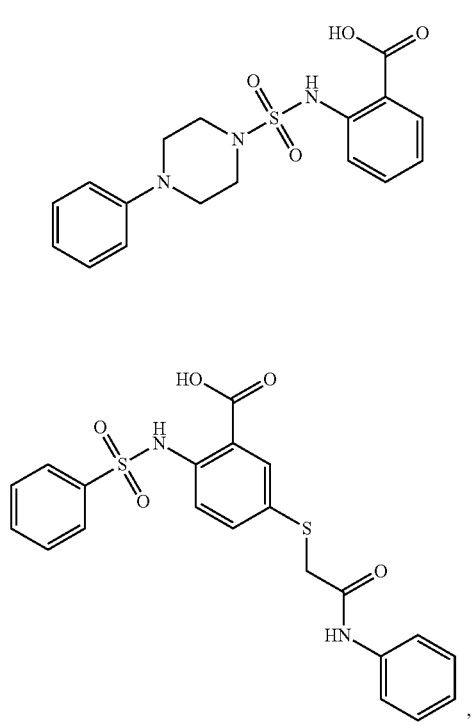
(395) 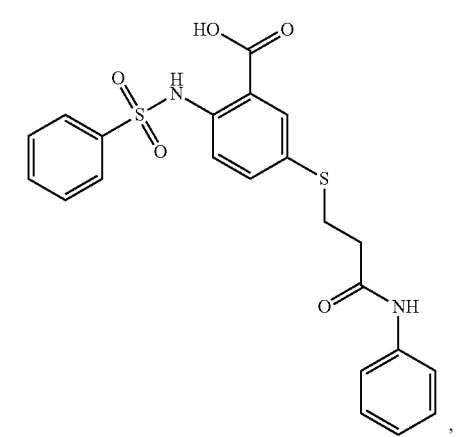
(410) 
(429) 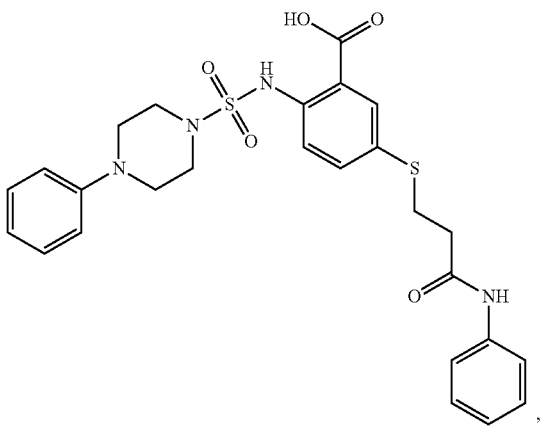
(435) 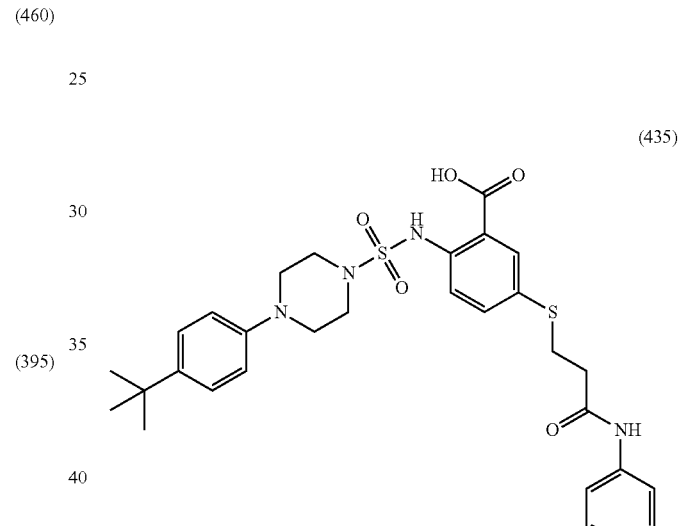
(479) 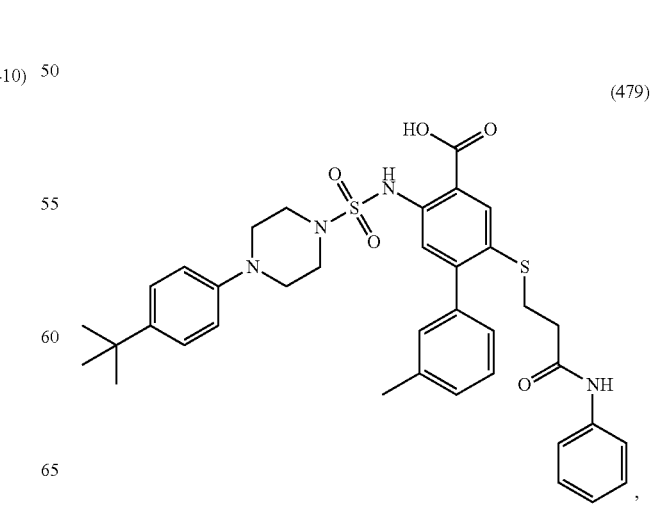

-continued

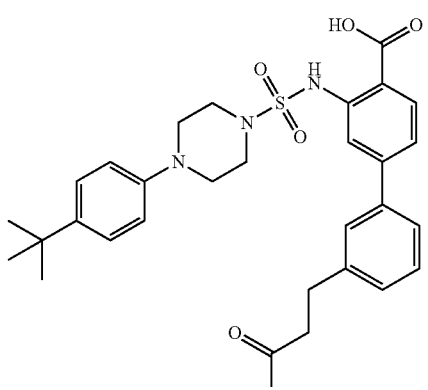
(484)

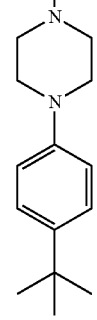
, and

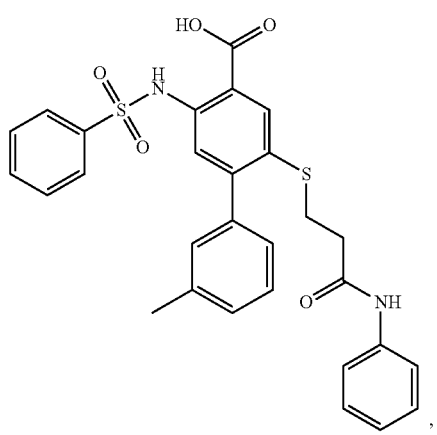
(485)

or a pharmaceutically acceptable salt, solvate, or prodrug thereof.

An important aspect of the present invention is that compounds of the invention induce cell cycle arrest and/or apoptosis and also potentiate the induction of cell cycle arrest and/or apoptosis either alone or in response to additional apoptosis induction signals. Therefore, it is contemplated that these compounds sensitize cells to induction of cell cycle arrest and/or apoptosis, including cells that are resistant to such inducing stimuli. The Mcl-1 inhibitors of the present invention (e.g., benzoic acid compounds) can be used to induce apoptosis in any disorder that can be treated, ameliorated, or prevented by the induction of apoptosis. In one embodiment, the inhibitors can be used to induce apoptosis in cells comprising functional Mcl-1 and/or Mcl-1-related proteins.

In some embodiments, the compositions and methods of the present invention are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. A non-limiting exemplary list of these diseases and conditions includes, but is not limited to, pancreatic cancer, breast cancer, prostate cancer, lymphoma, skin cancer, colon cancer, melanoma, malignant melanoma, ovarian cancer, brain cancer, primary brain carcinoma, head and neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic. In other embodiments, the cancer cells being treated are resistant to anticancer agents. In other embodiments, the disorder is any disorder having cells having Mcl-1 protein and/or Mcl-1-related protein expression.

Some embodiments of the present invention provide methods for administering an effective amount of a compound of the invention and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies). In a particular embodiment, the additional therapeutic agent(s) is an anticancer agent.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors; NF-κB modulators; anti-CDK compounds; HDAC inhibitors; and the like. Numerous other examples of chemotherapeutic compounds and anticancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); antiandrogens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of the invention and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 2 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 2

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2,4,6-triamine) | Hexalen | US Bioscience, West Conshohocken, PA |
| Amifostine (ethanethiol,2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |

TABLE 2-continued

| | | |
|---|---|---|
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus Calmette-Gukin* [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R.W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1 S,3 S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |

TABLE 2-continued

| | | |
|---|---|---|
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2', 2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2- | Gleevec | Novartis AG, Basel, Switzerland |

TABLE 2-continued

| | | |
|---|---|---|
| pyrimidinyl]amino]-phenyl]benzamide methanesulfonate) | | |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3',4': 6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S \cdot HCl$ | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6 H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylaminolbenzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum | Eloxatin | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R,3 S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegasparagase (monomethoxypolyethylene glycol succinimidyl L-asparaginase) | Oncaspar | Enzon |

TABLE 2-continued

| | | |
|---|---|---|
| Pegfilgrastim (covalent conjugate of recombinant methionyl human G-CSF (Filgrastim) and monomethoxy polyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N, N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |

TABLE 2-continued

| | | |
|---|---|---|
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity. Examples include, but are not limited to, 3-AP, 12-O-tetradecanoyl-phorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, huI4.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, 06-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering a compound of the invention with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy.

In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, a compound of the invention and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

This example describes synthetic routes for compounds described herein.

Scheme 1. Synthetic Route for LM and analogues[a]

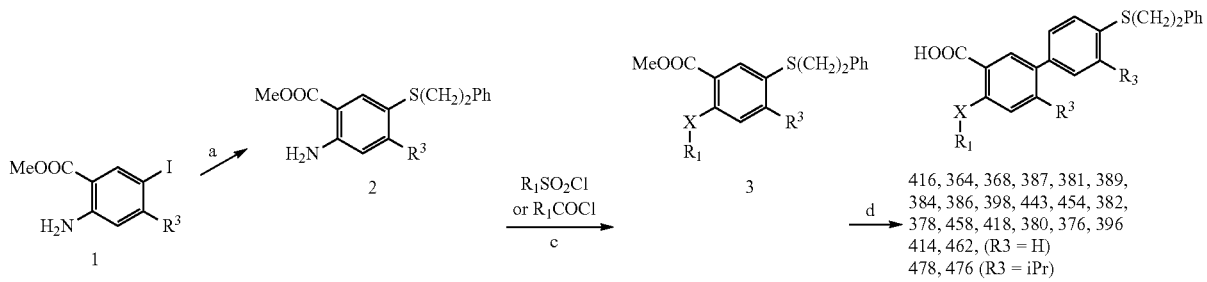

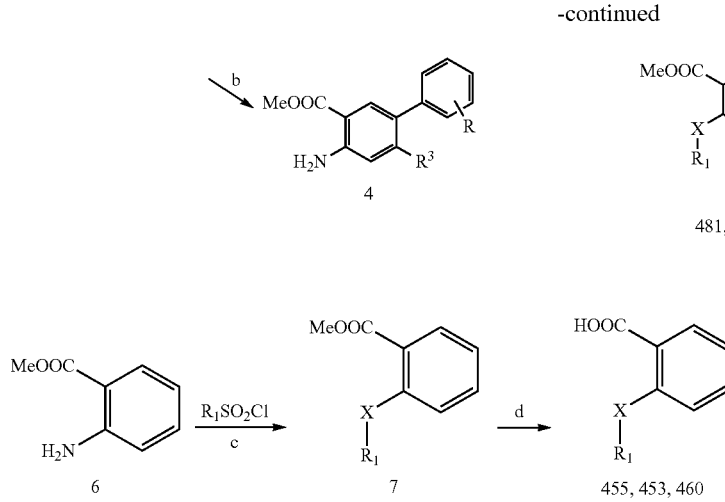
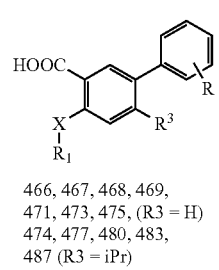

aReagents and conditions: (a) HS(CH₂)₂Ph, Pd₂(dba)₃, Xantphos, i-Pr₂NEt, 1,4-dioxane, reflux, 16 h; (b) RPhB(OH)₂, Pd(dppf)Cl₂, Na₂CO₃, DMF/H₂O, 80° C., 16 h; (c) pyridine, CH₂Cl₂, rt, 16 h or K₂CO₃, CH₂Cl₂, rt, 16 h or [imidazolium reagent], CH₃CN, 80° C., 16 h; (d) LiOH, MeOH/THF/H₂O, rT 16 h.

Synthesis. All analogues were synthesized through a novel, modular route (Scheme 1) which allows for facile access to a variety of analogues with variations at R1, R2 and R3 position in the benzoic acid scaffold. Methyl 2-amino-5-iodobenzoate (1, R3=H), which is commercially available, was subjected Pd-catalyzed C-S (see, e.g., Itoh, T; Mase, T. Org. Lett. 2004, 6, 4587-4590) or C-C (see, e.g., U.S. Patent Application Publication No. 2008/0293939) cross-coupling using conditions previously reported to provide desired intermediates (2, 4). Reaction of the amines with appropriate sulfonyl or acyl chlorides or 3-methyl-1-((piperazin-1-yl)sulfonyl)-1H-imidazol-3-iums (see, e.g., Beaudoin, S.; Kinsey, K. E.; Burns, J. F. J. Org. Chem. 2003, 68, 115-119) provided the penultimate compounds (3, 5), which were hydrolyzed with lithium hydroxide followed by purification by reverse-phase HPLC to afford the target compounds of >95% purity (Table 1). The analogues 478, 474, 476, 477, 480, 483, 487, 481, 482, 486 (Table 1) with isopropyl substituent at R3 position were obtained through modular route (Scheme 1) starting from methyl 2-amino-5-iodo-4-isopropylbenzoate (1, R3=iPr) which was synthesized based on the reported procedure (see, e.g., U.S. Patent Application Publication No. 2008/0293939). In the case of analogues with hydrogen at R2 and R3 positions, methyl 2-aminobenzoate (6) reacted with appropriate sulfonyl chlorides or 3-methyl-1-((piperazin-1-yl)sulfonyl)-1H-imidazol-3-iums to give the corresponding intermediates (7) which were hydrolyzed by LiOH to afford compounds 455 (Wydysh, E. A.; Medghalchi, S. M.; Vadlamudi, A.; Townsend, C. A. J. Med. Chem. 2009, 52, 3317-3327), 453 (Sosič, I.; Turk, S.; Sinreih, M.; Trošt, N.; Verlaine, O.; Amoroso, A.; Zervosen, A.; Luxen, A.; Joris, B.; Gobec, S. Acta Chim. Slov. 2012, 59, 380-388) and 460 (Table 1). Analogue 702 (Table 1) with phenylethanethio chain at R3 position was synthesized using conditions similar to those described for 368 starting from methyl 2-amino-4-iodobenzoate. Following the procedure of 368 and 396, phenylmethanethiol was used as the starting material to afford compound 392 and 456 (Table 1), respectively. The synthesis of 404 (Table 1) was completed starting from methyl 2-amino-5-nitrobenzoate. All reactions were performed under anhydrous conditions. Reagents were used as supplied without further purification. Reactions were monitored by TLC using precoated silica gel 60 F254 plates. Silica gel chromatography was performed with silica gel (40-60 m, 60A) obtained from Acros Organics. Purities of final compounds were assessed by analytical reverse-phase HPLC performed with method: Shimadzu system with a Restek Ultra C18 (4.6 mm×150 mm, 5 m particle size) column with the gradient 20% ACN/water (5 min), 20-100% ACN/water (24 min), 100% ACN/water (5 min) flow=1 mL/min. Semi-preparative HPLC was performed on a Shimadzu system with a Restek Ultra C18 (21.2 mm×150 mm, 5 m particle size) column. All NMR spectra were obtained in Actone-d6, Methanol-d4, DMSO-d6 or CDCl₃ and results were recorded at on a Bruker 300 MHz Ultrashield or 400 MHz Ascend or on a Varian 400 MHz or 500 MHz instrument. High resolution mass spectrometry (HRMS) analysis was performed on an Agilent Q-TOF system. All final compounds were purified to >95% purity.

Methyl 2-amino-5-(phenethylthio)benzoate (2)

Synthesized using reported procedure with modification (see, e.g., Itoh, T; Mase, T. Org. Lett. 2004, 6, 4587-4590). To a round-bottom-flask under nitrogen were added methyl 2-amino-5-iodobenzoate (1) (831 mg, 3 mmol, 1.0 equiv.), i-Pr₂Net (775 mg, 1.05 mL, 6 mmol, 2.0 equiv.) and dry 1,4-dioxane (30 mL). Catalyst Pd₂(dba)₃ (137 mg, 0.15 mmol, 0.05 equiv.), Xantphos (173 mg, 0.3 mmol, 0.1 equiv.) were then added and the mixture were stirred for 15 minutes. 2-Phenylethanethiol (415 mg, 0.4 mL, 3 mmol, 1.0 equiv.) was added and then the mixture was heated to reflux for 16 hours. The reaction mixture was then allowed to cool down to room temperature. The reaction mixture was then filtered and concentrated under reduced pressure. The crude product was purified by flash column chromatography (ethyl acetate:hexanes=15:85) on silica gel to afford 2 (862 mg, 82%) as yellow oil which solidified upon standing.

$^1$H NMR (300 MHz, CDCl$_3$) δ 7.99 (s, 1H), 7.37-7.14 (m, 6H), 6.62 (d, J=6.0 Hz, 1H), 5.80 (s, 2H), 3.87 (s, 3H), 3.04-2.99 (m, 2H), 2.87-2.82 (m, 2H); $^{13}$C NMR (75 MHz, CDCl$_3$) δ 168.01, 149.86, 140.36, 138.81, 135.95, 128.50, 128.41, 126.28, 120.81, 117.42, 111.11, 51.64, 37.81, 35.94.

2-Amino-5-(phenethylthio)benzoic acid (416)

To a round-bottom-flask LiOH (61 mg, 2.54 mmol, 5.0 equiv.) and H$_2$O (1 mL). MeOH (10 mL) were added, followed by methyl methyl 2-amino-5-(phenethylthio)benzoate (146 mg, 0.508 mmol, 1.0 equiv.) dissolved in THF (5 mL). The mixture was stirred for 16 hours. The reaction mixture was then acidified to pH=4 with 1N HCl solution. The resulting mixture was extracted with CH$_2$Cl$_2$ (2×50 mL). All the organic extractions were combined, dried over NaSO$_4$ and concentrated under reduced pressure to afford 416 (138 mg, 98%) as yellow solid.

$^1$H NMR (300 MHz, CDCl$_3$) δ 8.07 (s, 1H), 7.41-7.15 (m, 6H), 6.63 (d, J=9.0 Hz, 1H), 3.06-3.01 (m, 2H), 2.89-2.84 (m, 2H); $^{13}$C NMR (75 MHz, CDCl$_3$) δ 173.11, 150.48, 140.28, 139.71, 136.48, 126.30, 121.21, 117.63, 109.88, 37.68, 35.89. HRMS (ESI) m/z cacld for C$_{15}$H$_{15}$NO$_2$S [M+H]$^+$: 274.0896. Found: 274.0895.

Methyl 2-benzamido-5-(phenethylthio)benzoate (3a)

To a round-bottom-flask under nitrogen methyl 2-amino-5-iodobenzoate (2) (100 mg, 0.35 mmol, 1.0 equiv.) and dry CH$_2$Cl$_2$ (20 mL). K$_2$CO$_3$ (97 mg, 0.7 mmol, 2.0 equiv.) were added, followed by adding benzoyl chloride (59 mg, 0.049 mL, 0.42 mmol, 1.2 equiv.) and the mixture was stirred at room temperature for 16 hours. The reaction mixture was extracted with CH$_2$Cl$_2$ (2×20 mL), all organic extracts were combined, dried over NaSO$_4$ and concentrated under reduced pressure. The crude product was purified by flash column chromatography (ethyl acetate:hexanes=10:90) on silica gel to afford 3a (137 mg, 90%) as a yellow solid.

$^1$H NMR (400 MHz, CDCl$_3$) δ 11.97 (s, 1H), 8.90 (d, J=12.0 Hz, 1H), 8.10-8.03 (m, 3H), 7.62-7.18 (m, 9H), 3.97 (s, 3H), 3.18-3.14 (m, 2H), 2.94-2.90 (m, 2H); $^{13}$C NMR (100 MHz, CDCl$_3$) δ 168.52, 165.59, 140.34, 139.93, 136.58, 134.67, 132.59, 132.00, 129.87, 128.81, 128.50, 127.33, 126.48, 121.10, 115.74, 52.60, 36.06, 35.69.

2-Benzamido-5-(phenethylthio)benzoic acid (364)

Synthesized using the procedure for 416 except using 3a as the starting material, which afforded the title compound (73 mg, 98%) as a white solid.

$^1$H NMR (300 MHz, Acetone-d6) δ 12.21 (s, 1H), 8.94 (d, J=9.0 Hz, 1H), 8.18 (s, 1H), 8.04 (d, J=9.0 Hz, 2H), 7.75-7.56 (m, 4H), 7.34-7.19 (m, 5H), 3.29-3.24 (m, 2H), 2.98-2.93 (m, 2H); $^{13}$C NMR (75 MHz, Acetone-d6) δ 169.47, 164.81, 140.64, 140.23, 135.94, 134.92, 132.43, 132.06, 129.97, 128.86, 128.60, 128.39, 127.17, 126.31, 120.69, 115.97, 35.37, 35.28. HRMS (ESI) m/z cacld for C$_{22}$H$_{19}$NO$_3$S [M+H]$^+$: 378.1158. Found: 378.1154.

Methyl 5-(phenethylthio)-2-(phenylsulfonamido)benzoate (3b)

To a round-bottom-flask under nitrogen methyl 2-amino-5-iodobenzoate (2) (100 mg, 0.35 mmol, 1.0 equiv.) and dry CH$_2$Cl$_2$ (20 mL) were added. Pyridine (83 mg, 0.085 mL, 1.05 mmol, 3.0 equiv.) and corresponding benzenesulfonyl chloride (93 mg, 0.067 mL, 0.525 mmol, 1.5 equiv.) were added and the mixture was stirred at room temperature for 16 hours. The reaction mixture was then concentrated under reduced pressure. The crude product was purified by flash column chromatography (ethyl acetate:hexanes=15:85) on silica gel to afford 3b (131 mg, 88%) as a yellow oil.

$^1$H NMR (300 MHz, CDCl$_3$) δ 10.51 (s, 1H), 7.89-7.82 (m, 3H), 7.64 (d, J=9.0 Hz, 1H), 7.53-7.41 (m, 4H), 7.30-7.13 (m, 5H), 3.87 (s, 3H), 3.12-3.07 (m, 2H), 2.88-2.83 (m, 2H); $^{13}$C NMR (75 MHz, CDCl$_3$) δ 167.70, 139.74, 139.23, 138.59, 135.91, 133.08, 132.29, 130.88, 129.02, 128.52, 128.46, 127.20, 126.55, 120.02, 116.66, 52.61, 35.77, 35.54.

5-(Phenethylthio)-2-(phenylsulfonamido)benzoic acid (368)

Synthesized using the procedure for 416 except using 3b as the starting material, which afforded the title compound (66 mg, 85%) as a yellow solid.

$^1$H NMR (300 MHz, Acetone-d6) δ 7.97 (s, 1H), 7.88 (d, J=9.0 Hz, 2H), 7.72-7.53 (m, 5H), 7.30-7.17 (m, 5H), 3.22-3.17 (m, 2H), 2.90-2.85 (m, 2H); $^{13}$C NMR (75 MHz, Acetone-d6) δ 169.07, 140.07, 139.36, 138.93, 135.95, 133.35, 132.23, 131.10, 129.30, 128.55, 128.36, 127.14, 126.30, 119.63, 116.84, 35.20, 34.96. HRMS (ESI) m/z cacld for C$_{21}$H$_{19}$NO$_4$S$_2$[M+H]$^+$: 414.0828. Found: 414.0821.

Methyl 2-amino-4-(phenethylthio)benzoate (8)

Synthesized using the procedure for 2 except using methyl 2-amino-4-iodobenzoate as the starting material, which afforded the desired compound (218 mg, 80%) as a yellow oil.

$^1$H NMR (300 MHz, CDCl$_3$) δ 7.42 (d, J=9.0 Hz, 1H), 7.32-7.17 (m, 5H), 6.54-6.46 (m, 2H), 5.72 (s, 2H), 3.81 (s, 3H), 3.17-3.11 (m, 2H), 2.95-2.90 (m, 2H); $^{13}$C NMR (75 MHz, CDCl$_3$) δ 168.11, 150.44, 144.51, 139.79, 131.34, 128.44, 128.37, 126.46, 114.72, 113.34, 107.72, 51.30, 35.07, 33.04.

4-(Phenethylthio)-2-(phenylsulfonamido)benzoic acid (702)

Synthesized using the procedure for 416 except using E701LL8 as the starting material, which afforded the title compound (70 mg, 87%) as a yellow solid.

$^1$H NMR (300 MHz, Acetone-d6) δ 7.90 (d, J=9.0 Hz, 3H), 7.65-7.50 (m, 4H), 7.35-7.22 (m, 5H), 7.01 (d, J=9.0 Hz, 1H), 3.29-3.24 (m, 2H), 3.01-2.96 (m, 2H); $^{13}$C NMR (75 MHz, Acetone-d6) δ 169.44, 146.81, 141.30, 139.87, 139.40, 133.44, 131.93, 129.41, 128.65, 128.50, 127.11, 126.53, 120.69, 114.69, 111.97, 34.73, 32.69. HRMS (ESI) m/z cacld for C$_{21}$H$_{19}$NO$_4$S$_2$[M+H]$^+$: 414.0828. Found: 414.0824.

Methyl 2-amino-5-(benzylthio)benzoate (9)

Synthesized using the procedure for 2 except using phenylmethanethiol as the starting material, which afforded the desired compound (766 mg, 93%) as a yellow oil which solidified upon standing.

$^1$H NMR (300 MHz, CDCl$_3$) δ 7.87 (s, 1H), 7.28-7.14 (m, 6H), 6.51 (d, J=9.0 Hz, 1H), 5.78 (s, 2H), 3.93 (s, 2H), 3.84

(s, 3H); $^{13}$C NMR (75 MHz, CDCl$_3$) δ 167.99, 150.06, 139.52, 138.15, 136.84, 128.94, 128.29, 126.87, 120.41, 117.10, 110.98, 51.55, 41.76.

Methyl 5-(benzylthio)-2-(phenylsulfonamido)benzoate (391)

Synthesized using the procedure for 3b except using 9 as the starting material, which afforded the title compound (90 mg, 98%) as a yellow oil which solidified upon standing.

$^1$H NMR (300 MHz, CDCl$_3$) δ 10.52 (s, 1H), 7.83-7.80 (m, 3H), 7.61-7.15 (m, 10H), 4.01 (s, 2H), 3.84 (s, 3H); $^{13}$C NMR (75 MHz, CDCl$_3$) δ 167.68, 139.18, 139.04, 137.07, 137.01, 133.63, 133.07, 130.28, 129.00, 128.82, 128.47, 127.27, 127.19, 119.74, 116.42, 52.54, 39.79.

5-(Benzylthio)-2-(phenylsulfonamido)benzoic acid (392)

Synthesized using the procedure for 416 except using 391 as the starting material, which afforded the title compound (59 mg, 89%) as a yellow solid.

$^1$H NMR (300 MHz, Acetone-d6) δ 7.94-7.85 (m, 3H), 7.65-7.49 (m, 5H), 7.24-7.20 (m, 5H), 4.14 (s, 2H); $^{13}$C NMR (100 MHz, Acetone-d6) δ 169.36, 139.39, 139.34, 137.49, 136.39, 133.47, 133.29, 130.50, 129.27, 128.90, 128.33, 127.11, 119.30, 38.61.

HRMS (ESI) m/z cacld for C$_{20}$H$_{17}$NO$_4$S$_2$[M+H]$^+$: 400.0672. Found: 400.0670.

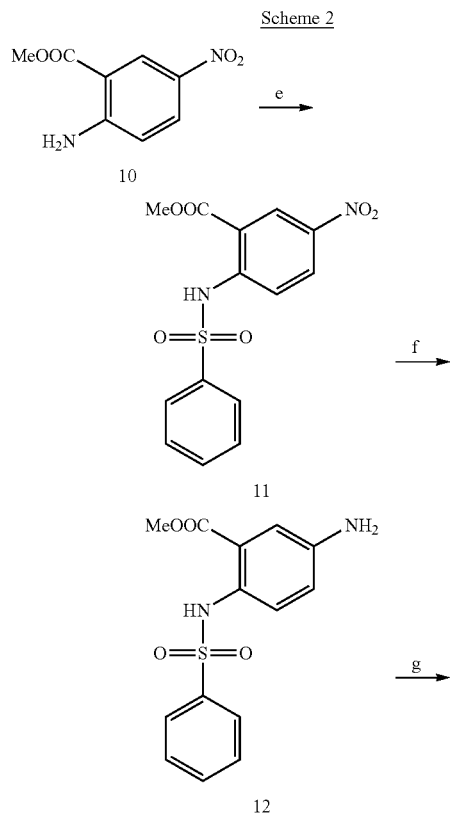

Scheme 2

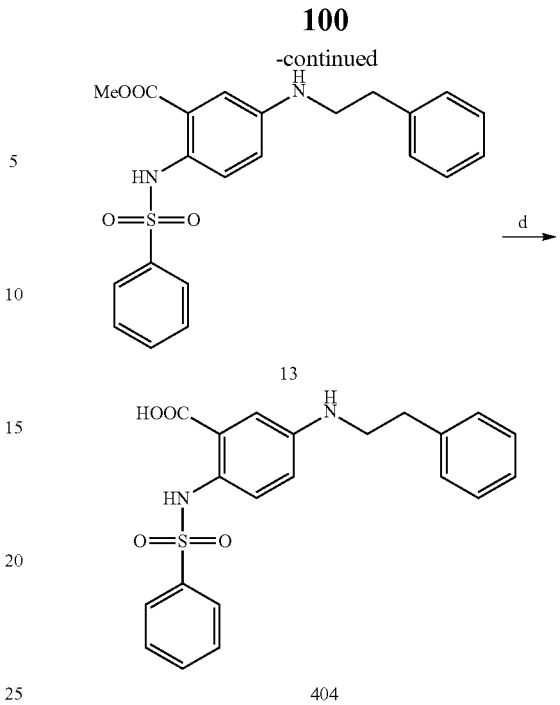

$^b$Reagents and conditions; (e) benzenesulfonyl chloride, NaH, THF, 0° C. to rt, 16 h; (f) iron powder, AcOH/EtOH, reflux, 4 h; (g) 1-(2-chloroethyl) benzene, K$_2$CO$_3$, DMF, 120° C., 16 h; (d) LiOH, MeOH/THF/H$_2$O, rt, 16 h.

methyl 5-nitro-2-(phenylsulfonamido)benzoate (11)

To a round-bottom-flask under nitrogen methyl 2-amino-5-nitrobenzoate 10 (500 mg, 2.55 mmol, 1.0 equiv.) and dry THF (30 mL) were added at 0° C. NaH (60% oil dispersion powder, 460 mg, 11.48 mmol, 4.5 equiv.) was added and the mixture was stirred for 1 hour, followed by addition of benzenesulfonyl chloride (1.35 g, 0.98 mL, 7.65 mmol, 3.0 equiv.) and the mixture was stirred at room temperature for additional 16 hours. The reaction mixture was then allowed to cool down at 0° C. and quenched by saturated NH$_4$Cl (20 mL). The resulting mixture was extracted with Et$_2$O (2×50 mL). All the organic extracts were combined, dried over NaSO$_4$ and concentrated. The crude product was purified by flash column chromatography (ethyl acetate:hexanes=20:80) on silica gel to afford reported compound 11 (1.1 g, 64%) as a yellow solid (see, e.g., U.S. Patent Application Publication No. 20040157836).

methyl 5-amino-2-(phenylsulfonamido)benzoate (12)

Synthesized using reported procedure with modification (see, e.g., Krolski, M. E.; Renaldo, A. F.; Rudisill, D. E.; Stille, J. K. J. Org. Chem. 1988, 53, 1176-1183). To a round-bottom-flask under nitrogen iron powder (321 mg, 5.75 mmol, 5.0 equiv.), AcOH (10 mL) and dry EtOH (10 mL) were added. Methyl 5-nitro-2-(phenylsulfonamido) benzoate 11 (388 mg, 1.15 mmol, 1.0 equiv.) was added and then the mixture was heated to reflux for 4 hours. The reaction mixture was then allowed to cool down to room temperature and diluted with H$_2$O (100 mL). Na$_2$CO$_3$ (20 g) was added to the mixture and then was extracted with Et$_2$O (2×100 mL). All the organic extracts were combined, dried over NaSO$_4$ and concentrated. The crude product was purified by flash column chromatography (ethyl acetate: hexanes=60:40) on silica gel to afford 12 (267 mg, 75%) as a yellow solid.

$^1$H NMR (300 MHz, CDCl$_3$) δ 9.71 (s, 1H), 7.68 (d, J=6.0 Hz, 2H), 7.54-7.34 (m, 4H), 7.12 (d, J=3.0 Hz, 1H), 6.82 (dd, J=9.0, 3.0 Hz, 1H), 3.72-3.68 (m, 5H); $^{13}$C NMR (75 MHz, CDCl$_3$) δ 167.73, 143.09, 138.84, 132.66, 130.57, 128.64, 127.17, 123.74, 120.98, 119.16, 116.07, 52.24.

methyl 5-(phenethylamino)-2-(phenylsulfonamido)benzoate (13)

To a round-bottom-flask under nitrogen methyl 5-amino-2-(phenylsulfonamido)benzoate 12 (184 mg, 0.6 mmol, 1.0 equiv.) and dry DMF (20 mL) were added. This was followed by addition of K$_2$CO$_3$ (691 mg, 3 mmol, 5.0 equiv.) and 1-(2-chloroethyl)benzene (0.199 mL, 211 mg, 1.5 mmol, 2.5 equiv.) and the mixture was heated at 120° C. for 16 hours. The reaction mixture was then allowed to cool down to room temperature and diluted with ice H$_2$O (20 mL). The resulting mixture was extracted with Et$_2$O (2×30 mL). All the organic extracts were combined, dried over NaSO$_4$ and concentrated. The crude product was purified by flash column chromatography (ethyl acetate:hexanes=50:50) on silica gel to afford 13 (211 mg, 85%) as yellow oil.

$^1$H NMR (400 MHz, CDCl$_3$) δ 7.62-7.12 (m, 11H), 6.71-6.64 (m, 2H), 3.92-3.69 (m, 6H), 3.03-2.85 (m, 2H); $^{13}$C NMR (100 MHz, CDCl$_3$) δ 166.57, 146.52, 139.75, 138.58, 133.08, 132.16, 131.83, 128.78, 128.64, 128.41, 127.73, 127.38, 126.31, 117.75, 117.00, 53.61, 52.04, 35.58.

5-(phenethylamino)-2-(phenylsulfonamido)benzoic acid (404)

Synthesized using the procedure for 416 except using 13 as the starting material, which afforded the desired compound (100 mg, 98%) as a yellow solid.

$^1$H NMR (400 MHz, CDCl$_3$) δ 7.63-7.08 (m, 11H), 6.69 (d, J=8.0 Hz, 1H), 6.57 (d, J=8.0 Hz, 1H), 3.95-3.62 (m, 2H), 2.98-2.76 (m, 2H); $^{13}$C NMR (100 MHz, CDCl$_3$) δ 168.07, 146.11, 138.71, 138.29, 133.58, 132.59, 130.76, 128.77, 128.71, 128.42, 127.85, 127.58, 126.37, 118.20, 117.74, 53.52, 35.14.

HRMS (ESI) m/z cacld for C$_{21}$H$_{20}$N$_2$O$_4$S [M+H]$^+$: 414.0828. Found: 414.0824.

methyl 2-(phenylsulfonamido)benzoate (7a)

Synthesized using the procedure for 3b except using 6 as the starting material, which afforded the desired compound (587 mg, 50%) as a white solid (see, e.g., Wydysh, E. A.; Medghalchi, S. M.; Vadlamudi, A.; Townsend, C. A. J. Med. Chem. 2009, 52, 3317-3327).

2-(phenylsulfonamido)benzoic acid (455)

Synthesized based on the procedure for 416 except using 7a as the starting material, which afforded the title compound (90 mg, 90%) as a white solid (see, e.g., Wydysh, E. A.; Medghalchi, S. M.; Vadlamudi, A.; Townsend, C. A. J. Med. Chem. 2009, 52, 3317-3327).

methyl 2-(naphthalene-2-sulfonamido)benzoate (7b)

Synthesized using the procedure for 3b except using 6 and naphthalene-2-sulfonyl chloride as the starting material, which afforded the desired compound (610 mg, 89%) as a white solid (see, e.g., Sosič, I.; et al., Acta Chim. Slov. 2012, 59, 380-388).

2-(naphthalene-2-sulfonamido)benzoic acid (453)

Synthesized using the procedure for 416 except using 7b as the starting material, which afforded the title compound (80 mg, 90%) as a white solid (see, e.g., Sosič, I.; et al., Acta Chim. Slov. 2012, 59, 380-388).

methyl 5-(phenethylthio)-2-(thiophene-2-sulfonamido)benzoate (3c)

Synthesized using the procedure for 3b except using thiophene-2-sulfonyl chloride as the starting material, which afforded the title compound (89 mg, 98%) as a yellow oil which solidified upon standing.

$^1$H NMR (400 MHz, CDCl$_3$) δ 10.59 (s, 1H), 7.92 (s, 1H), 7.73 (d, J=8.0 Hz, 1H), 7.59-6.99 (m, 9H), 3.89 (s, 3H), 3.12 (t, J=8.0 Hz, 2H), 2.88 (t, J=8.0 Hz, 2H); $^{13}$C NMR (100 MHz, CDCl$_3$) δ 167.69, 139.93, 139.75, 138.26, 135.82, 132.85, 132.49, 132.24, 131.36, 128.54, 128.47, 127.28, 126.57, 120.20, 116.89, 52.66, 35.74, 35.55.

5-(phenethylthio)-2-(thiophene-2-sulfonamido)benzoic acid (387)

Synthesized using the procedure for 416 except using 3c as the starting material, which afforded the desired compound (53 mg, 87%) as a yellow solid.

$^1$H NMR (400 MHz, CDCl$_3$) δ 10.46 (s, 1H), 8.02 (s, 1H), 7.73-6.99 (m, 10H), 3.14 (t, J=8.0 Hz, 2H), 2.89 (t, J=8.0 Hz, 2H); $^{13}$C NMR (100 MHz, CDCl$_3$) δ 171.65, 139.65, 139.59, 138.58, 136.49, 133.10, 132.79, 131.80, 128.55, 128.48, 127.39, 126.58, 119.98, 116.12, 35.55, 35.46. HRMS (ESI) m/z cacld for C$_{19}$H$_{17}$NO$_4$S$_3$[M+H]$^+$: 420.0392. Found: 420.0284.

methyl 2-(4-chlorophenylsulfonamido)-5-(phenethylthio)benzoate (3d)

Synthesized using the procedure for 3b except using 4-chlorobenzene-1-sulfonyl chloride as the starting material, which afforded the title compound (97 mg, 98%) as a yellow oil.

$^1$H NMR (400 MHz, CDCl$_3$) δ 10.50 (s, 1H), 7.89 (s, 1H), 7.78-7.15 (m, 11H), 3.88 (s, 3H), 3.11 (t, J=8.0 Hz, 2H), 2.87 (t, J=8.0 Hz, 2H); $^{13}$C NMR (100 MHz, CDCl$_3$) δ 167.72, 139.71, 139.65, 138.22, 137.76, 135.82, 132.21, 131.46, 129.34, 128.67, 128.54, 128.45, 126.58, 120.12, 116.81, 52.66, 35.69, 35.54.

2-(4-chlorophenylsulfonamido)-5-(phenethylthio) benzoic acid (381)

Synthesized using the procedure for 416 except using 3d as the starting material, which afforded the title compound (65 mg, 93%) as a yellow solid.

$^1$H NMR (400 MHz, CDCl$_3$) δ 10.37 (s, 1H), 8.00 (s, 1H), 7.79-7.15 (m, 11H), 3.13 (t, J=8.0 Hz, 2H), 2.88 (t, J=8.0 Hz, 2H); $^{13}$C NMR (100 MHz, CDCl$_3$) δ 171.71, 139.91, 139.60, 138.55, 137.50, 136.58, 132.82, 131.82, 129.50, 128.65, 128.55, 128.45, 126.59, 119.62, 115.77, 35.51, 35.43. HRMS (ESI) m/z cacld for C$_{21}$H$_{18}$ClNO$_4$S$_2$[M+H]$^+$: 448.0439. Found: 448.0431.

methyl 2-(4-bromophenylsulfonamido)-5-(phenethylthio)benzoate (3e)

Synthesized using the procedure for 3b except using 4-bromobenzene-1-sulfonyl chloride as the starting material, which afforded the title compound (100 mg, 98%) as a yellow oil which solidified upon standing.

$^1$H NMR (400 MHz, CDCl$_3$) δ 10.51 (s, 1H), 7.89 (s, 1H), 7.70-7.15 (m, 11H), 3.88 (s, 3H), 3.11 (t, J=8.0 Hz, 2H), 2.87 (t, J=8.0 Hz, 2H); $^{13}$C NMR (100 MHz, CDCl$_3$) δ 167.73, 139.71, 138.30, 138.19, 135.81, 132.32, 132.20, 131.49, 128.74, 128.55, 128.46, 128.17, 126.58, 120.12, 116.82, 52.66, 35.68, 35.54.

2-(4-bromophenylsulfonamido)-5-(phenethylthio)benzoic acid (389)

Synthesized using the procedure for 416 and 3e as the starting material, which afforded the desired compound (73 mg, 98%) as a yellow oil which solidified upon standing.

$^1$H NMR (400 MHz, CDCl$_3$) δ 10.26 (s, 1H), 8.01 (s, 1H), 7.74-7.16 (m, 11H), 3.15 (t, J=8.0 Hz, 2H), 2.90 (t, J=8.0 Hz, 2H); $^{13}$C NMR (100 MHz, CDCl$_3$) δ 171.68, 139.58, 138.61, 138.07, 136.78, 132.77, 132.52, 131.94, 128.71, 128.57, 128.50, 128.46, 126.62, 119.73, 115.37, 35.51, 35.45.

HRMS (ESI) m/z cacld for C$_{21}$H$_{18}$BrNO$_4$S$_2$[M+H]$^+$: 491.9933. Found: 491.9920.

methyl 2-(3-bromophenylsulfonamido)-5-(phenethylthio)benzoate (377)

Synthesized using the procedure for 3b except using 3-bromobenzene-1-sulfonyl chloride as the starting material, which afforded the title compound (99 mg, 98%) as a yellow oil.

$^1$H NMR (400 MHz, CDCl$_3$) δ 10.52 (s, 1H), 7.98 (s, 1H), 7.89 (s, 1H), 7.75-7.15 (m, 10H), 3.89 (s, 3H), 3.12 (t, J=8.0 Hz, 2H), 2.87 (t, J=8.0 Hz, 2H); $^{13}$C NMR (100 MHz, CDCl$_3$) δ 167.74, 141.08, 139.72, 138.05, 136.13, 135.84, 132.22, 131.62, 130.49, 130.13, 128.54, 128.47, 126.58, 125.75, 122.99, 120.30, 117.01, 52.73, 35.69, 35.55.

2-(3-bromophenylsulfonamido)-5-(phenethylthio)benzoic acid (384)

Synthesized using the procedure for 416 except using 3f as the starting material, which afforded the title compound (65 mg, 94%) as a yellow oil which solidified upon standing.

$^1$H NMR (400 MHz, CDCl$_3$) δ 10.39 (s, 1H), 8.01 (s, 2H), 7.76-7.15 (m, 10H), 3.13 (t, J=8.0 Hz, 2H), 2.88 (t, J=8.0 Hz, 2H); $^{13}$C NMR (100 MHz, CDCl$_3$) δ 171.62, 140.88, 139.62, 138.39, 136.56, 136.33, 132.83, 131.96, 130.65, 130.14, 128.55, 128.48, 126.59, 125.70, 123.12, 119.88, 35.52, 35.46.

HRMS (ESI) m/z cacld for C$_{21}$H$_{18}$BrNO$_4$S$_2$[M+H]$^+$: 491.9933. Found: 491.9924.

methyl 2-(2-bromophenylsulfonamido)-5-(phenethylthio)benzoate (383)

Synthesized using the procedure for 3b except using 2-bromobenzene-1-sulfonyl chloride as the starting material, which afforded the title compound (99 mg, 98%) as a yellow oil.

$^1$H NMR (400 MHz, CDCl$_3$) δ 11.15 (s, 1H), 8.26 (d, J=8.0 Hz, 1H), 7.95 (s, 1H), 7.67 (d, J=8.0 Hz, 1H), 7.48-7.12 (m, 9H), 3.94 (s, 3H), 3.08 (t, J=8.0 Hz, 2H), 2.85 (t, J=8.0 Hz, 2H); $^{13}$C NMR (100 MHz, CDCl$_3$) δ 167.59, 139.77, 138.27, 138.18, 136.16, 135.54, 134.17, 132.83, 132.24, 129.93, 128.50, 128.45, 127.52, 126.52, 120.39, 117.50, 115.72, 52.70, 35.93, 35.62.

2-(2-bromophenylsulfonamido)-5-(phenethylthio)benzoic acid (386)

Synthesized using the procedure for 416 except using 3g as the starting material, which afforded the title compound (70 mg, 92%) as a yellow oil which solidified upon standing.

$^1$H NMR (400 MHz, CDCl$_3$) δ 10.97 (s, 1H), 8.26 (d, J=8.0 Hz, 1H), 8.05 (s, 1H), 7.67 (d, J=8.0 Hz, 1H), 7.49-7.13 (m, 9H), 3.11 (t, J=8.0 Hz, 2H), 2.87 (t, J=8.0 Hz, 2H); $^{13}$C NMR (100 MHz, CDCl$_3$) δ 172.01, 139.65, 138.53, 137.98, 136.91, 135.61, 134.25, 133.29, 132.30, 130.58, 128.51, 128.47, 127.62, 126.53, 120.28, 117.59, 35.68, 35.52. HRMS (ESI) m/z cacld for C$_{21}$H$_{18}$BrNO$_4$S$_2$ [M+H]$^+$: 491.9933. Found: 491.9905.

methyl 5-(phenethylthio)-2-(2-phenylethylsulfonamido)benzoate (3i)

Synthesized using the procedure for 3b except using 2-phenylethanesulfonyl chloride as the starting material, which afforded the title compound (140 mg, 88%) as a yellow oil which solidified upon standing.

$^1$H NMR (300 MHz, CDCl$_3$) δ 10.36 (s, 1H), 8.01 (d, J=3.0 Hz, 1H), 7.70 (d, J=9.0 Hz, 1H), 7.51 (dd, J=9.0, 2.0 Hz, 1H), 7.32-7.08 (m, 10H), 3.93 (s, 3H), 3.44-3.38 (m, 2H), 3.17-3.09 (m, 4H), 2.93-2.88 (m, 2H); $^{13}$C NMR (75 MHz, CDCl$_3$) δ 167.76, 139.75, 139.13, 137.24, 136.49, 132.87, 130.42, 128.76, 128.53, 128.48, 128.23, 126.91, 126.55, 118.59, 115.74, 53.26, 52.70, 35.96, 35.63, 29.59.

5-(phenethylthio)-2-(2-phenylethylsulfonamido)benzoic acid (443)

Synthesized using the procedure for 416 except using 3i as the starting material, which afforded the title compound (110 mg, 95%) as a yellow oil which solidified upon standing.

$^1$H NMR (300 MHz, CDCl$_3$) δ 10.05 (s, 1H), 8.09 (d, J=2.0 Hz, 1H), 7.71 (d, J=9.0 Hz, 1H), 7.56 (dd, J=9.0, 3.0 Hz, 1H), 7.33-7.08 (m, 10H), 3.50-3.44 (m, 2H), 3.20-3.12 (m, 4H), 2.96-2.90 (m, 2H); $^{13}$C NMR (75 MHz, CDCl$_3$) δ 171.68, 139.64, 139.45, 137.38, 136.98, 133.34, 130.96, 128.83, 128.57, 128.50, 128.25, 127.02, 126.60, 118.36, 114.55, 53.28, 35.77, 35.54, 29.61. HRMS (ESI) m/z cacld for C$_{23}$H$_{23}$NO$_4$S$_2$[M+H]$^+$: 442.1141. Found: 442.1134.

methyl 5-(phenethylthio)-2-(3-phenylpropanamido)benzoate (3j)

Synthesized using the procedure for 3a except using 3-phenylpropanoyl chloride as the starting material, which afforded the title compound (106 mg, 98%) as a yellow oil.

$^1$H NMR (400 MHz, CDCl$_3$) δ 10.99 (s, 1H), 8.69 (d, J=8.0 Hz, 1H), 8.02 (s, 1H), 7.54 (d, J=8.0 Hz, 1H), 7.31-7.16 (m, 9H), 3.91 (s, 3H), 3.15-3.05 (m, 4H), 2.89 (t, J=8.0 Hz, 2H), 2.75 (d, J=8.0 Hz, 2H); $^{13}$C NMR (100 MHz, CDCl$_3$) δ 170.98, 168.11, 140.51, 139.99, 139.92, 136.50, 132.50, 129.57, 128.49, 128.32, 126.46, 126.20, 121.03, 115.39, 52.41, 40.12, 36.07, 35.67, 31.31.

5-(phenethylthio)-2-(3-phenylpropanamido)benzoic acid (454)

Synthesized using the procedure for 416 except using 3j as the starting material, which afforded the title compound (68 mg, 94%) as a yellow oil which solidified upon standing.

$^1$H NMR (400 MHz, CDCl$_3$) δ 10.80 (s, 1H), 8.71 (d, J=8.0 Hz, 1H), 8.11 (d, J=4.0 Hz, 1H), 7.59 (d, J=8.0 Hz, 1H), 7.30-7.17 (m, 10H), 3.15 (t, J=8.0 Hz, 2H), 3.09 (t, J=8.0 Hz, 2H), 2.91 (t, J=8.0 Hz, 2H), 2.78 (t, J=8.0 Hz, 2H); $^{13}$C NMR (100 MHz, CDCl$_3$) δ 171.55, 171, 44, 140.33, 140.23, 139.84, 137.26, 133.06, 130.33, 128.59, 128.54, 128.50, 128.33, 126.54, 126.35, 121.31, 114.52, 40.23, 35.93, 35.64, 31.39. HRMS (ESI) m/z cacld for C$_{24}$H$_{23}$NO$_3$S [M+H]$^+$: 406.1471. Found: 406.1468.

methyl 2-(naphthalene-2-sulfonamido)-5-(phenethylthio)benzoate (3k 379)

Synthesized using the procedure for 3b except using naphthalene-2-sulfonyl chloride as the starting material, which afforded the title compound (206 mg, 98%) as a yellow oil.

$^1$H NMR (300 MHz, CDCl$_3$) δ 10.66 (s, 1H), 8.44 (s, 1H), 7.91-7.08 (m, 14H), 3.82 (s, 3H), 3.07-3.02 (m, 2H), 2.83-2.78 (m, 2H); $^{13}$C NMR (75 MHz, CDCl$_3$) δ 167.67, 139.65, 138.51, 136.01, 135.84, 134.82, 132.20, 131.82, 130.75, 129.40, 129.18, 128.94, 128.81, 128.40, 128.37, 127.78, 127.52, 126.42, 122.07, 119.72, 116.48, 52.51, 35.62, 35.42.

2-(naphthalene-2-sulfonamido)-5-(phenethylthio) benzoic acid (382)

Synthesized using the procedure for 416 except using 3k as the starting material, which afforded the title compound (137 mg, 92%) as a yellow oil which solidified upon standing.

$^1$H NMR (300 MHz, Acetone-d6) δ 11.12 (br, 1H), 8.58 (s, 1H), 8.10-7.54 (m, 9H), 7.22-7.16 (m, 5H), 3.14-3.09 (m, 2H), 2.82-2.77 (m, 2H); $^{13}$C NMR (75 MHz, Acetone-d6) δ 169.16, 140.01, 138.96, 136.29, 135.60, 134.98, 132.26, 132.03, 131.02, 129.68, 129.31, 129.17, 128.89, 128.52, 128.33, 127.92, 127.77, 126.28, 122.08, 119.50, 116.69, 35.16, 34.92.

HRMS (ESI) m/z cacld for C$_{25}$H$_{21}$NO$_4$S$_2$[M+H]$^+$: 464.0985. Found: 464.0978.

methyl 2-([1,1'-biphenyl]-4-ylsulfonamido)-5-(phenethylthio)benzoate (3l)

Synthesized using the procedure for 3b except using biphenyl-4-sulfonyl chloride as the starting material, which afforded the title compound (255 mg, 98%) as a yellow oil.

$^1$H NMR (300 MHz, CDCl$_3$) δ 10.56 (s, 1H), 7.91-7.88 (m, 3H), 7.71-7.12 (m, 14H), 3.86 (s, 3H), 3.12-3.07 (m, 2H), 2.88-2.83 (m, 2H); $^{13}$C NMR (75 MHz, CDCl$_3$) δ 167.71, 145.91, 139.70, 138.96, 138.58, 137.74, 135.89, 132.27, 130.86, 128.98, 128.51, 128.48, 128.42, 127.71, 127.57, 127.20, 126.50, 119.94, 116.62, 52.59, 35.70, 35.50.

2-([1,1'-biphenyl]-4-ylsulfonamido)-5-(phenethylthio)benzoic acid ((378)

Synthesized using the procedure for 416 except using 3l as the starting material, which afforded the title compound (148 mg, 87%) as a yellow oil which solidified upon standing.

$^1$H NMR (300 MHz, Acetone-d6) δ 11.07 (br, 1H), 7.99-7.14 (m, 17H), 3.19-3.14 (m, 2H), 2.88-2.83 (m, 2H); $^{13}$C NMR (75 MHz, Acetone-d6) δ 169.19, 145.70140.05, 138.96, 138.76, 138.05, 135.66, 132.34, 131.08, 129.05, 128.58, 128.54, 128.35, 127.83, 127.60, 127.17, 126.29, 119.54, 116.83, 35.21, 34.97.

HRMS (ESI) m/z cacld for C$_{27}$H$_{23}$NO$_4$S$_2$[M+H]$^+$: 490.1141. Found: 490.1134.

methyl 2-([1,1'-biphenyl]-2-ylsulfonamido)-5-(phenethylthio)benzoate (3m)

Synthesized using the procedure for 3b except using biphenyl-2-sulfonyl chloride as the starting material, which afforded the title compound (232 mg, 92%) as a yellow oil.

$^1$H NMR (400 MHz, CDCl$_3$) δ 9.82 (s, 1H), 8.33 (dd, J=8.0, 4.0 Hz, 1H), 7.88 (d, J=2.0 Hz, 1H), 7.59-7.118 (m, 15H), 3.79 (s, 3H), 3.05 (t, J=4.0 Hz, 2H), 2.83 (t, J=4.0 Hz, 2H); $^{13}$C NMR (100 MHz, CDCl$_3$) δ 166.60, 141.21, 139.82, 138.57, 138.32, 137.23, 136.16, 132.91, 132.86, 132.78, 130.39, 128.97, 128.74, 128.50, 128.44, 128.07, 127.78, 126.51, 116.74, 115.01, 52.32, 36.11, 35.59.

2-([1,1'-biphenyl]-2-ylsulfonamido)-5-(phenethylthio)benzoic acid (458)

Synthesized using the procedure for 416 except using 3m as the starting material, which afforded the title compound (88 mg, 76%) as a yellow oil which solidified upon standing.

$^1$H NMR (400 MHz, CDCl$_3$) δ 9.50 (s, 1H), 8.37 (d, J=8.0 Hz, 1H), 8.00 (s, 1H), 7.62-7.17 (m, 15H), 3.13 (t, J=8.0 Hz, 2H), 2.90 (t, J=8.0 Hz, 2H); $^{13}$C NMR (100 MHz, CDCl$_3$) δ 171.54, 141.12, 139.69, 138.81, 138.61, 137.15, 137.04, 133.10, 133.06, 133.02, 130.42, 129.48, 129.02, 128.58, 128.46, 128.28, 127.92, 126.60, 116.76, 113.75, 35.89, 35.52.

HRMS (ESI) m/z cacld for C$_{27}$H$_{23}$NO$_4$S$_2$[M+H]$^+$: 490.1141. Found: 490.1132.

methyl 2-(4-cyclohexylphenylsulfonamido)-5-(phenethylthio)benzoate (3n)

Synthesized using the procedure for 3b except using 4-cyclohexylbenzene-1-sulfonyl chloride as the starting material, which afforded the title compound (110 mg, 98%) as a yellow oil which solidified upon standing.

$^1$H NMR (300 MHz, CDCl$_3$) δ 10.48 (s, 1H), 7.89-7.13 (m, 12H), 3.86 (s, 3H), 3.12-3.07 (m, 2H), 2.88-2.83 (m, 2H), 2.51 (s, 1H), 1.82-1.76 (m, 5H), 1.39-1.32 (m, 5H); $^{13}$C NMR (75 MHz, CDCl$_3$) δ 167.68, 153.76, 139.74, 138.80, 136.49, 135.99, 132.37, 130.45, 128.49, 128.44, 127.48, 127.28, 126.51, 119.83, 116.51, 52.56, 44.45, 35.80, 35.55, 33.94, 26.54, 25.85.

2-(4-cyclohexylphenylsulfonamido)-5-(phenethylthio)benzoic acid (418)

Synthesized using the procedure for 416 except using 3n as the starting material, which afforded the title compound (60 mg, 77%) as a yellow oil which solidified upon standing.

$^1$H NMR (300 MHz, Acetone-d6) δ 10.95 (br, 1H), 7.98-7.18 (m, 12H), 3.21-3.16 (m, 2H), 2.88-2.83 (m, 2H), 2.56 (s, 1H), 1.78-1.68 (m, 5H), 1.43-1.20 (m, 5H); $^{13}$C NMR (75 MHz, Acetone-d6) δ 169.04, 153.89, 140.07, 139.17, 136.82, 135.78, 132.39, 130.76, 128.55, 128.36, 127.66, 127.32, 126.31, 119.41, 116.53, 44.19, 35.25, 35.04, 33.73, 26.39, 25.65.

methyl 2-(4'-chloro-[1,1'-biphenyl]-4-ylsulfonamido)-5-(phenethylthio)benzoate (3o 374)

Synthesized using the procedure for 3b except using 4-chlorobiphenyl-4-sulfonyl chloride as the starting material, which afforded the title compound (105 mg, 98%) as a yellow oil.

$^1$H NMR (300 MHz, CDCl$_3$) δ 10.58 (s, 1H), 7.91-7.13 (m, 16H), 3.87 (s, 3H), 3.13-3.07 (m, 2H), 2.88-2.83 (m, 2H); $^{13}$C NMR (75 MHz, CDCl$_3$) δ 167.74, 144.66, 139.71, 138.55, 138.15, 137.44, 135.92, 134.82, 132.29, 130.93, 129.21, 128.52, 128.48, 128.44, 127.85, 127.46, 126.55, 119.88, 116.59, 52.64, 35.72, 35.52.

2-(4'-chloro-[1,1'-biphenyl]-4-ylsulfonamido)-5-(phenethylthio)benzoic acid (380)

Synthesized using the procedure for 416 except using 3o as the starting material, which afforded the title compound (67 mg, 96%) as a yellow oil which solidified upon standing.

$^1$H NMR (300 MHz, Acetone-d6) δ 11.07 (br, 1H), 7.99-7.15 (m, 16H), 3.20-3.15 (m, 2H), 2.87-2.82 (m, 2H); $^{13}$C NMR (75 MHz, Acetone-d6) δ 166.20, 144.28, 140.05, 138.87, 138.40, 137.50, 135.59, 134.26, 132.32, 131.13, 129.09, 128.83, 128.53, 128.34, 127.91, 127.57, 126.29, 119.54, 35.19, 34.93.

HRMS (ESI) m/z cacld for C$_{27}$H$_{22}$ClNO$_4$S$_2$[M+H]$^+$: 524.0752. Found: 524.0744.

HRMS (ESI) m/z cacld for C$_{27}$H$_{29}$NO$_4$S$_2$[M+H]$^+$: 496.1611. Found: 496.1606.

Methyl 5-(phenethylthio)-2-(4-phenoxyphenylsulfonamido)benzoate (3p)

Synthesized using the procedure for 3b except using 4-phenoxybenzene-1-sulfonyl chloride as the starting material, which afforded the title compound (88 mg, 98%) as a yellow oil.

$^1$H NMR (300 MHz, CDCl$_3$) δ 10.49 (s, 1H), 7.91 (d, J=2.4 Hz, 1H), 7.80-7.76 (m, 2H), 7.64 (d, J=9 Hz, 1H), 7.46-7.14 (m, 9H), 7.03-6.92 (m, 4H), 3.88 (s, 3H), 3.14-3.08 (m, 2H), 2.90-2.85 (m, 2H); $^{13}$C NMR (75 MHz, CDCl$_3$) δ 167.73, 161.91, 154.85, 139.75, 138.73, 135.96, 132.68, 132.36, 130.72, 130.16, 129.50, 128.54, 128.47, 126.56, 125.04, 120.33, 119.85, 117.39, 116.55, 52.62, 35.80, 35.56.

5-(Phenethylthio)-2-(4-phenoxyphenylsulfonamido)benzoic acid (376)

Synthesized using the procedure for 416 except using 3p as the starting material, which afforded the title compound (57 mg, 98%) as a yellow oil which solidified upon standing.

$^1$H NMR (300 MHz, Acetone-d6) δ 10.92 (br, 1H), 8.00-7.02 (m, 17H), 3.23-3.16 (m, 2H), 2.91-2.86 (m, 2H); $^{13}$C NMR (75 MHz, Acetone-d6) δ 169.06, 161.96, 155.03, 140.09, 138.99, 135.62, 132.96, 132.30, 131.01, 130.29, 129.69, 128.56, 128.37, 126.31, 125.07, 120.30, 119.68, 117.45, 116.96, 35.21, 35.00.

HRMS (ESI) m/z cacld for C$_{27}$H$_{23}$NO$_5$S$_2$[M+H]$^+$: 506.1090. Found: 506.1083.

Scheme 3

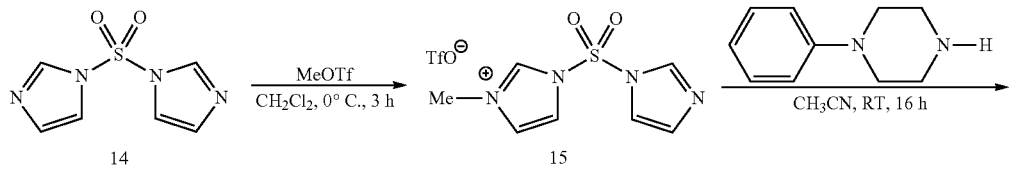

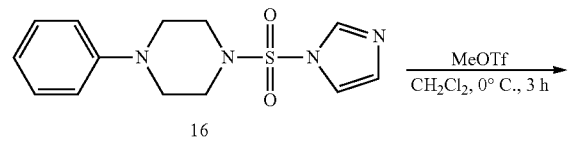

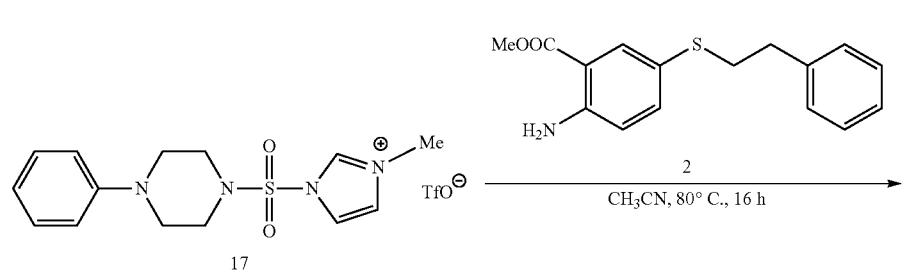

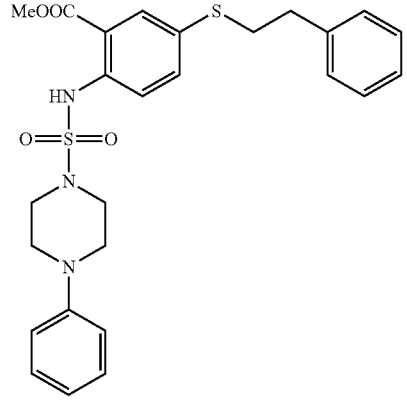

3q

Methyl 5-(phenethylthio)-2-(1-phenylpiperazine-4-sulfonamido)benzoate (3q)

Synthesized using reported procedure with modification (see, e.g., Beaudoin, S.; Kinsey, K. E.; Burns, J. F. J. Org. Chem. 2003, 68, 115-119). To a round-bottom-flask under nitrogen 1-(1H-imidazol-1-ylsulfonyl)-1H-imidazole 14 (80 mg, 0.4 mmol, 2 equiv.) and dry $CH_2Cl_2$ (10 mL) were added at 0° C. MeOTf (72 mg, 0.05 mL, 0.44 mmol, 2.2 equiv.) was added and then the mixture was stirred for 3 hours. The solvent was removed under reduced pressure and re dissolved in dry $CH_3CN$ (10 mL) at room temperature. 1-Phenylpiperazine (65 mg, 0.061 mL, 0.4 mmol, 2 equiv.) was added and then the mixture was stirred for 16 hours. The reaction mixture was concentrated under reduced pressure. The crude product was dissolved in dry $CH_2Cl_2$ (10 mL) at 0° C. MeOTf (72 mg, 0.05 mL, 0.44 mmol, 2.2 equiv.) was added, followed by stirring the mixture for 2 hours. The solvent was removed under reduced pressure and re dissolved in dry $CH_3CN$ (10 mL) at room temperature. Methyl 2-amino-5-(phenethylthio)benzoate 2 (57.5 mg, 0.2 mmol, 1.0 equiv.) was added and then the mixture was heated to reflux for 16 hours. The reaction mixture was then allowed to cool down and concentrated under reduced pressure. The crude product was purified by flash column chromatography (ethyl acetate:hexanes=30:70) on silica gel to afford 3q (75 mg, 73% over 2 steps) as yellow oil which solidified upon standing.

$^1$H NMR (300 MHz, $CDCl_3$) δ 10.45 (s, 1H), 8.02 (d, J=2.1 Hz, 1H), 7.68 (d, J=9.0 Hz, 1H), 7.51 (dd, J=9.0, 3.0 Hz, 1H), 7.31-7.16 (m, 7H), 6.92-6.86 (m, 3H), 3.94 (s, 3H), 3.44-3.41 (m, 4H), 3.19-3.11 (m, 6H), 2.92-2.87 (m, 2H); $^{13}$C NMR (75 MHz, $CDCl_3$) δ 167.98, 150.59, 139.81, 139.76, 136.43, 132.74, 129.78, 129.22, 128.52, 128.48, 126.53, 120.80, 119.24, 116.79, 115.36, 52.67, 49.07, 46.28, 36.07, 35.64.

5-(Phenethylthio)-2-(1-phenylpiperazine-4-sulfonamido)benzoic acid (396)

Synthesized using the procedure for 416 except using 3q as the starting material, which afforded the compound (60 mg, 98%) as a yellow oil which solidified upon standing.

$^1$H NMR (300 MHz, Acetone-d6) δ 10.77 (br, 1H), 8.10 (s, 1H), 7.77-7.67 (m, 2H), 7.31-7.19 (m, 7H), 6.96-6.80 (m, 3H), 3.42-3.39 (m, 4H), 3.26-3.19 (m, 6H), 2.94-2.89 (m, 2H); $^{13}$C NMR (75 MHz, Acetone-d6) δ 169.20, 151.01, 140.15, 136.19, 132.69, 129.81, 128.97, 128.57, 128.37, 126.29, 120.07, 119.36, 116.52, 115.58, 48.71, 46.23, 35.34.

HRMS (ESI) m/z cacld for $C_{25}H_{27}N_3O_4S_2[M+H]^+$: 498.1516. Found: 498.1516.

methyl 5-(benzylthio)-2-(1-phenylpiperazine-4-sulfonamido)benzoate (18)

Synthesized using the procedure for 3q except using 9 as the starting material, which afforded the title compound (181 mg, 74%) as a yellow oil which solidified upon standing.

$^1$H NMR (400 MHz, $CDCl_3$) δ 10.44 (s, 1H), 7.95 (s, 1H), 7.61 (d, J=8.0 Hz, 1H), 7.41-6.86 (m, 11H), 4.04 (s, 2H), 3.91 (s, 3H), 3.41-3.38 (m, 4H), 3.16-3.13 (m, 4H); $^{13}$C NMR (100 MHz, $CDCl_3$) δ 167.93, 150.58, 140.12, 137.49, 137.14, 134.00, 129.21, 129.19, 128.84, 128.46, 127.24, 120.78, 118.99, 116.76, 115.16, 52.58, 49.03, 46.24, 40.02.

5-(benzylthio)-2-(1-phenylpiperazine-4-sulfonamido)benzoic acid (456)

Synthesized using the procedure for 416 except using 18 as the starting material, which afforded the title compound (88 mg, 98%) as a yellow oil which solidified upon standing.

$^1$H NMR (400 MHz, $CDCl_3$) δ 10.51 (br, 1H), 8.74 (br, 1H), 8.01 (d, J=2.4 Hz, 1H), 7.60 (d, J=8.8 Hz, 1H), 7.41-7.11 (m, 11H), 4.06 (s, 2H), 3.53 (t, J=4.6 Hz, 4H), 3.32 (t, J=4.8 Hz, 1H); $^{13}$C NMR (125 MHz, $CDCl_3$) δ 170.47, 147.52, 139.83, 137.42, 136.94, 134.14, 130.33, 129.78, 128.88, 128.50, 127.31, 124.42, 119.45, 118.41, 115.49, 51.02, 45.48, 39.68, 30.93.

HRMS (ESI) m/z cacld for $C_{24}H_{25}N_3O_4S_2[M+H]^+$: 484.1359. Found: 484.1366.

methyl 2-(1-benzylpiperazine-4-sulfonamido)-5-(phenethylthio)benzoate (3r)

Synthesized using the procedure for 3q except using 1-benzylpiperazine as the starting material, which afforded the title compound (155 mg, 85%) as a yellow oil.

$^1$H NMR (300 MHz, $CDCl_3$) δ 10.54 (s, 1H), 8.01 (s, 1H), 7.53-7.18 (m, 12H), 4.13 (s, 2H), 3.93 (s, 3H), 3.62 (br, 4H), 3.18-3.12 (m, 6H), 2.91 (t, J=6.0 Hz, 2H); $^{13}$C NMR (75 MHz, $CDCl_3$) δ 168.07, 139.75, 138.36, 136.03, 132.32, 131.28, 130.95, 130.28, 129.38, 128.48, 127.76, 126.51, 119.33, 115.92, 60.90, 52.79, 50.18, 43.46, 35.71, 35.49.

2-(1-benzylpiperazine-4-sulfonamido)-5-(phenethylthio)benzoic acid (414)

Synthesized using the procedure for 416 except using 3r as the starting material, which afforded the title compound (64 mg, 83%) as a yellow oil which solidified upon standing.

$^1$H NMR (400 MHz, CDCl$_3$) δ 8.01 (d, J=2.0 Hz, 1H), 7.57 (d, J=8.8 Hz, 1H), 7.41-7.17 (m, 11H), 4.09 (s, 2H), 3.50-3.11 (m, 10H), 2.90 (t, J=7.8 Hz, 2H); $^{13}$C NMR (125 MHz, CDCl$_3$) δ 171.22, 139.93, 138.34, 134.84, 132.70, 131.46, 131.02, 130.23, 129.30, 128.51, 128.48, 127.84, 126.46, 120.09, 119.13, 60.83, 50.54, 43.77, 35.57, 35.49.

HRMS (ESI) m/z cacld for C$_{26}$H$_{29}$N$_3$O$_4$S$_2$[M+H]$^+$: 512.1672. Found: 512.1673.

methyl 2-(1-(4-fluorobenzyl)piperazine-4-sulfonamido)-5-(phenethylthio)benzoate (3s)

Synthesized using the procedure for 3q except using 1-(4-fluorobenzyl)piperazine as the starting material, which afforded the title compound (100 mg, 53%) as a yellow oil.

1H NMR (400 MHz, CDCl$_3$) δ 10.38 (s, 1H), 8.02 (s, 1H), 7.65-6.95 (m, 11H), 3.93 (s, 3H), 3.44 (s, 2H), 3.29 (s, 4H), 3.14 (t, J=8.0 Hz, 2H), 2.90 (t, J=8.0 Hz, 2H), 2.43 (s, 4H); $^{13}$C NMR (100 MHz, CDCl$_3$) δ 167.93, 163.31, 139.90, 139.83, 136.48, 132.81, 130.53, 130.46, 129.46, 128.53, 128.48, 126.53, 119.09, 115.25, 115.04, 61.72, 52.62, 52.00, 46.20, 36.13, 35.67.

2-(1-(4-fluorobenzyl)piperazine-4-sulfonamido)-5-(phenethylthio)benzoic acid (462)

Synthesized using the procedure for 416 except using 3s as the starting material, which afforded the title compound (41 mg, 60%) as a yellow oil which solidified upon standing.

$^1$H NMR (400 MHz, CDCl$_3$) δ 10.85 (s, 1H), 8.01 (s, 1H), 7.56 (d, J=8.0 Hz, 1H), 7.43-7.01 (m, 10H), 4.06 (s, 2H), 3.51 (br, 4H), 3.15-3.12 (m, 6H), 2.90 (t, J=8.0 Hz, 2H); $^{13}$C NMR (100 MHz, CDCl$_3$) δ 171.16, 164.93, 162.43, 139.90, 138.80, 135.01, 133.10, 133.01, 132.65, 131.67, 128.51, 126.50, 123.87, 120.13, 118.76, 116.58, 116.36, 60.07, 50.55, 43.77, 35.56, 35.48.

HRMS (ESI) m/z cacld for C$_{26}$H$_{29}$N$_3$O$_4$S$_2$[M+H]$^+$: 530.1578. Found: 5530.172.

methyl 2-(1-phenylpiperazine-4-sulfonamido)benzoate (7c)

Synthesized using the procedure for 3q except using methyl 2-aminobenzoate as the starting material, which afforded the title compound (195 mg, 86%) as a yellow oil which solidified upon standing.

$^1$H NMR (400 MHz, CDCl$_3$) δ 10.54 (s, 1H), 8.02 (t, J=4.0 Hz, 1H), 7.74 (d, J=8.0 Hz, 1H), 7.53-6.86 (m, 8H), 3.94 (s, 3H), 3.44-3.42 (m, 4H), 3.17-3.15 (m, 4H); 13C NMR (100 MHz, CDCl$_3$) δ 168.49, 150.63, 141.27, 134.54, 131.19, 129.19, 122.24, 120.72, 118.51, 116.74, 114.77, 52.49, 49.04, 46.23.

2-(1-phenylpiperazine-4-sulfonamido)benzoic acid (460)

Synthesized using the procedure for 416 except using 7c as the starting material, which afforded the title compound (94 mg, 98%) as a yellow oil which solidified upon standing.

$^1$H NMR (400 MHz, CDCl$_3$) δ 8.08 (t, J=8.0 Hz, 1H), 7.71-6.87 (m, 8H), 3.43 (d, J=4.0 Hz, 4H), 3.15 (d, J=4.0 Hz, 4H); $^{13}$C NMR (100 MHz, CDCl$_3$) δ 170.14, 150.47, 140.96, 134.26, 131.75, 129.05, 122.25, 120.76, 118.18, 116.76, 115.24, 49.03, 46.02.

HRMS (ESI) m/z cacld for C$_{17}$H$_{19}$N$_3$O$_4$S [M+H]$^+$: 362.1169. Found: 362.1167.

methyl 4-amino-4'-propyl-[1,1'-biphenyl]-3-carboxylate (4a)

Synthesized using reported procedure with modification (US Patent Application Publication Culshaw et al., Pub. No. US 2008/0293939 A1, Nov. 27, 2008). To a round-bottom-flask under nitrogen methyl 2-amino-5-iodobenzoate (1) (831 mg, 3 mmol, 1.0 equiv.), 4-propylphenylboronic acid (541 mg, 3.3 mmol, 1.1 equiv.) and DMF (20 mL) were added, followed by addition of catalyst Pd(dppf)Cl$_2$ (110 mg, 0.15 mmol, 0.05 equiv.) and the mixture were stirred for 15 minutes. 2M Na$_2$CO$_3$ solution (7.5 mL, 15 mmol, 5.0 equiv.) was added and then the mixture was heated at 80° C. for 16 hours. The reaction mixture was allowed to cool down to room temperature. The reaction mixture was filtered and concentrated under reduced pressure. H$_2$O (20 mL) was added to the residue which was extracted with EtOAc (2×20 mL). All the organic extracts were combined, dried over NaSO$_4$ and concentrated under reduced pressure. The crude product was purified by flash column chromatography (ethyl acetate:hexanes=20:80) on silica gel to afford 4a (418 mg, 51%) as yellow solid.

$^1$H NMR (400 MHz, CDCl$_3$) δ 8.11 (s, 1H), 7.53-7.20 (m, 5H), 6.71 (d, J=8.0 Hz, 1H), 5.74 (s, 2H), 3.88 (s, 3H), 2.60 (t, J=8.0 Hz, 2H), 1.71-1.61 (m, 2H), 0.96 (t, J=8.0 Hz, 3H); $^{13}$C NMR (100 MHz, CDCl$_3$) δ 168.56, 149.48, 140.96, 137.74, 132.70, 129.37, 129.23, 128.81, 126.03, 117.13, 110.90, 51.54, 37.61, 24.55, 13.82.

methyl 4-(naphthalene-2-sulfonamido)-4'-propyl-[1,1'-biphenyl]-3-carboxylate (5a)

Synthesized using the procedure for 3k except using 4a as the starting material, which afforded the title compound (400 mg, 98%) as a yellow oil.

$^1$H NMR (400 MHz, CDCl$_3$) δ 10.74 (s, 1H), 8.47 (s, 1H), 8.08 (s, 1H), 7.91-7.18 (m, 12H), 3.84 (s, 3H), 2.58 (d, J=8.0 Hz, 2H), 1.67-1.58 (m, 2H), 0.93 (t, J=8.0 Hz, 3H); $^{13}$C NMR (100 MHz, CDCl$_3$) δ 168.26, 142.23, 139.08, 136.35, 136.28, 135.93, 134.87, 132.71, 131.91, 129.39, 129.22, 128.94, 128.88, 128.82, 127.79, 127.47, 126.40, 122.18, 119.44, 116.21, 52.42, 37.54, 24.41, 13.72.

4-(naphthalene-2-sulfonamido)-4'-propyl-[1,1'-biphenyl]-3-carboxylic acid (466)

Synthesized using the procedure for 416 except using 5a as the starting material, which afforded the desired compound (80 mg, 69%) as a yellow oil which solidified upon standing.

$^1$H NMR (400 MHz, CDCl$_3$) δ 8.49 (s, 1H), 8.18 (s, 1H), 7.95-7.55 (m, 8H), 7.40 (d, J=12.0 Hz, 2H), 7.19 (d, J=8.0 Hz, 2H), 2.58 (d, J=8.0 Hz, 2H), 1.68-1.59 (m, 2H), 0.93 (t, J=8.0 Hz, 3H); $^{13}$C NMR (100 MHz, CDCl$_3$) δ 170.06, 142.06, 139.05, 136.36, 135.97, 135.74, 134.84, 132.48, 131.85, 129.85, 129.40, 129.14, 128.83, 128.81, 127.72, 127.41, 126.30, 121.96, 118.76, 116.41, 37.43, 24.32, 13.56.

HRMS (ESI) m/z cacld for C$_{26}$H$_{23}$NO$_4$S [M+H]$^+$: 446.1421. Found: 446.1411.

methyl 4-amino-2'-((3-(trifluoromethyl)phenoxy) methyl)-[1,1'-biphenyl]-3-carboxylate (4b)

Synthesized using the procedure for 4a except using 2-((3-(trifluoromethyl)phenoxy)methyl)phenylboronic acid as the starting material, which afforded the title compound (600 mg, 75%) as a yellow oil which solidified upon standing.
$^1$H NMR (400 MHz, CDCl$_3$) δ 7.95 (s, 1H), 7.56-7.02 (m, 9H), 6.67 (d, J=12.0 Hz, 1H), 5.78 (s, 2H), 4.94 (s, 2H), 3.71 (s, 3H); $^{13}$C NMR (100 MHz, CDCl$_3$) δ 168.35, 158.58, 149.70, 141.65, 134.80, 133.20, 131.88, 131.77, 131.56, 130.11, 129.96, 129.86, 128.60, 128.06, 127.30, 125.27, 122.57, 117.92, 117.46, 117.42, 116.65, 111.81, 111.77, 110.38, 68.51, 51.35.

4-amino-2'-((3-(trifluoromethyl)phenoxy)methyl)-[1,1'-biphenyl]-3-carboxylic acid (467)

Synthesized using the procedure for 416 except using 4b as the starting material, affording the desired compound (100 mg, 96%) as a yellow oil which solidified upon standing.
$^1$H NMR (400 MHz, CDCl$_3$) δ 7.97 (s, 1H), 7.58-7.02 (m, 9H), 6.70 (d, J=12.0 Hz, 1H), 4.98 (s, 2H); $^{13}$C NMR (100 MHz, CDCl$_3$) δ 170.92, 158.55, 149.94, 141.44, 135.11, 133.31, 132.39, 131.45, 130.12, 129.81, 129.52, 128.41, 128.16, 127.26, 122.52, 118.06, 117.43, 117.39, 116.60, 111.82, 111.78, 110.13, 68.
HRMS (ESI) m/z cacld for C$_{21}$H$_{16}$F3NO$_3$ [M+H]$^+$: 388.1155. Found: 388.1155.

methyl 4-(naphthalene-2-sulfonamido)-2'-((3-(trifluoromethyl)phenoxy)methyl)-[1,1'-biphenyl]-3-carboxylate (5b)

Synthesized using the procedure for 3k except using 4b as the starting material, which afforded the title compound (255 mg, 86%) as a yellow oil which solidified upon standing.
$^1$H NMR (400 MHz, CDCl$_3$) δ 10.80 (s, 1H), 8.49 (s, 1H), 8.00-6.92 (m, 17H), 4.80 (s, 2H), 3.68 (s, 3H); $^{13}$C NMR (100 MHz, CDCl$_3$) δ 168.10, 158.32, 140.43, 139.72, 136.36, 135.03, 134.93, 134.76, 133.08, 131.96, 131.78, 131.60, 130.30, 130.06, 129.93, 129.45, 129.24, 128.98, 128.86, 128.82, 128.14, 127.85, 127.56, 122.22, 118.63, 117.72, 117.63, 117.60, 115.44, 111.72, 111.69, 68.27, 52.30.

4-(naphthalene-2-sulfonamido)-2'-((3-(trifluoromethyl)phenoxy)methyl)-[1,1'-biphenyl]-3-carboxylic acid (468)

Synthesized using the procedure for 416 except using 5b as the starting material, which afforded the title compound (106 mg, 90%) as a yellow oil which solidified upon standing.
$^1$H NMR (400 MHz, CDCl$_3$) δ 10.51 (s, 1H), 8.51 (s, 1H), 8.09 (s, 1H), 7.93-6.94 (m, 16H), 4.85 (s, 2H); $^{13}$C NMR (100 MHz, CDCl$_3$) δ 171.67, 158.32, 140.27, 140.08, 136.21, 136.13, 135.05, 135.03, 133.24, 132.73, 131.99, 130.18, 130.14, 129.99, 129.67, 129.28, 129.14, 129.01, 128.84, 128.29, 127.92, 127.69, 122.06, 118.45, 118.23, 117.80, 117.76, 114.11, 111.51, 68.31.
HRMS (ESI) m/z cacld for C$_{31}$H$_{22}$F3NO$_5$S [M+H]$^+$: 578.1244. Found: 578.1234.

methyl 4-amino-4'-((3-(trifluoromethyl)phenoxy) methyl)-[1,1'-biphenyl]-3-carboxylate (4c)

Synthesized using the procedure for 4a except using 4-((3-(trifluoromethyl)phenoxy) methyl)phenylboronic acid as the starting material, which afforded the title compound (550 mg, 68%) as a yellow oil which solidified upon standing.
$^1$H NMR (400 MHz, CDCl$_3$) δ 8.13 (s, 1H), 7.58-7.12 (m, 9H), 6.73 (d, J=8.0 Hz, 1H), 5.79 (s, 2H), 5.10 (s, 2H), 3.89 (s, 3H); $^{13}$C NMR (100 MHz, CDCl$_3$) δ 168.47, 158.86, 149.84, 140.40, 134.30, 132.72, 132.01, 131.69, 129.98, 129.50, 128.70, 128.07, 126.44, 118.26, 117.62, 117.59, 117.22, 111.74, 111.70, 110.93.

4-amino-4'-((3-(trifluoromethyl)phenoxy)methyl)-[1,1'-biphenyl]-3-carboxylic acid (469)

Synthesized using the procedure for 416 except using 4c as the starting material, which afforded the title compound (107 mg, 91%) as a yellow oil which solidified upon standing.
$^1$H NMR (400 MHz, DMSO) δ 8.02 (s, 1H), 7.63-7.29 (m, 9H), 6.87 (d, J=8.0 Hz, 1H), 5.21 (s, 2H); $^{13}$C NMR (100 MHz, DMSO) δ 169.95, 159.12, 151.44, 140.00, 134.72, 132.56, 131.18, 130.96, 130.64, 129.34, 128.97, 126.50, 125.93, 119.58, 117.69, 117.62, 111.86, 111.82, 110.38, 69.90.
HRMS (ESI) m/z cacld for C$_{21}$H$_{16}$F3NO$_3$ [M+H]$^+$: 388.1155. Found: 388.1155.

methyl 4-(naphthalene-2-sulfonamido)-4'-((3-(trifluoromethyl)phenoxy)methyl)-[1,1'-biphenyl]-3-carboxylate (5c)

Synthesized using the procedure for 3k except using 4c as the starting material, which afforded the title compound (290 mg, 98%) as a yellow oil.
$^1$H NMR (400 MHz, CDCl$_3$) δ 10.79 (s, 1H), 8.50 (s, 1H), 8.12 (s, 1H), 7.95-7.11 (m, 16H), 5.10 (s, 2H), 3.88 (s, 3H); $^{13}$C NMR (100 MHz, CDCl$_3$) δ 168.23, 158.71, 139.54, 139.04, 136.21, 135.65, 135.37, 134.97, 132.92, 131.97, 130.02, 129.50, 129.30, 129.01, 128.93, 128.06, 127.86, 127.58, 126.94, 122.18, 119.41, 118.23, 117.70, 116.22, 111.72, 69.84, 52.56.

4-(naphthalene-2-sulfonamido)-4'-((3-(trifluoromethyl)phenoxy)methyl)-[1,1'-biphenyl]-3-carboxylic acid (471)

Synthesized using the procedure for 416 except using 5c as the starting material, which afforded the title compound (145 mg, 91%) as a yellow oil which solidified upon standing.
$^1$H NMR (400 MHz, CDCl$_3$) δ 8.50 (s, 1H), 8.20 (s, 1H), 7.96-7.12 (m, 16H), 5.10 (s, 2H); 10 $^{13}$C NMR (100 MHz, CDCl$_3$) δ 169.97, 158.63, 139.57, 139.04, 136.02, 135.42, 135.09, 134.88, 132.64, 131.88, 130.10, 129.92, 129.47, 129.17, 128.90, 128.84, 127.94, 127.76, 127.47, 126.80, 121.98, 118.75, 118.13, 117.60, 117.56, 111.64, 111.60, 69.78.
HRMS (ESI) m/z cacld for C$_{31}$H$_{22}$F3NO$_5$S [M+H]$^+$: 578.1244. Found: 578.1246.

methyl 4-amino-2'-((naphthalen-1-yloxy)methyl)-[1,1'-biphenyl]-3-carboxylate (4d)

Synthesized using the procedure for 4a except using 2-((naphthalen-1-yloxy)methyl) phenylboronic acid as the starting material, which afforded the title compound (744 mg, 97%) as a yellow oil.

¹H NMR (400 MHz, CDCl₃) δ 8.32 (d, J=8.0 Hz, 1H), 8.01 (s, 1H), 7.76-7.24 (m, 10H), 6.68 (d, J=8.0 Hz, 1H), 6.54 (d, J=8.0 Hz, 1H), 5.68 (s, 2H), 5.03 (s, 2H), 3.36 (s, 3H); ¹³C NMR (100 MHz, CDCl₃) δ 168.33, 154.17, 149.56, 141.63, 134.75, 134.42, 133.85, 131.72, 130.17, 129.91, 128.35, 128.20, 127.27, 127.13, 126.25, 125.79, 125.65, 125.02, 122.26, 120.17, 116.58, 110.31, 104.73, 68.35, 50.95.

methyl 2'-((naphthalen-1-yloxy)methyl)-4-(naphthalene-2-sulfonamido)-[1,1'-biphenyl]-3-carboxylate (5d)

Synthesized using the procedure for 3k except using 4d as the starting material, which afforded the title compound (339 mg, 98%) as a yellow oil.
¹H NMR (400 MHz, CDCl₃) δ 10.76 (s, 1H), 8.46 (s, 1H), 8.23 (d, J=8.0 Hz, 1H), 8.08 (d, J=4.0 Hz, 1H), 7.91-7.23 (m, 17H), 6.61 (d, J=8.0 Hz, 1H), 4.92 (s, 2H), 3.22 (s, 3H); ¹³C NMR (100 MHz, CDCl₃) δ 168.11, 153.96, 140.53, 139.56, 136.35, 134.99, 134.92, 134.47, 133.79, 131.96, 131.85, 130.67, 129.93, 129.42, 129.28, 128.94, 128.84, 128.66, 128.04, 127.85, 127.53, 127.38, 126.38, 125.78, 125.58, 125.12, 122.23, 122.15, 120.40, 118.73, 115.50, 104.61, 68.17, 51.83.

2'-((naphthalen-1-yloxy)methyl)-4-(naphthalene-2-sulfonamido)-[1,1'-biphenyl]-3-carboxylic acid (473)

Synthesized using the procedure for 416 and 5d as the starting material, which afforded the desired compound (137 mg, 83%) as a yellow oil which solidified upon standing.
¹H NMR (400 MHz, CDCl₃) δ 10.40 (s, 1H), 8.46 (s, 1H), 8.21 (d, J=8.0 Hz, 1H), 8.09 (d, J=2.0 Hz, 1H), 7.82-7.22 (m, 17H), 6.62 (d, J=8.0 Hz, 1H), 5.00 (s, 2H); ¹³C NMR (100 MHz, CDCl₃) δ 171.72, 154.06, 140.04, 139.87, 136.13, 136.07, 135.41, 134.97, 134.46, 134.07, 132.69, 131.95, 129.98, 129.61, 129.28, 129.08, 128.95, 128.49, 128.22, 127.88, 127.62, 127.40, 126.48, 125.65, 125.62, 125.18, 122.09, 122.04, 120.59, 118.71, 114.42, 104.91, 68.14.
HRMS (ESI) m/z cacld for $C_{34}H_{25}NO_5S$ [M+H]⁺: 560.1526. Found: 560.1510.

methyl 4-amino-4'-((naphthalen-1-yloxy)methyl)-[1,1'-biphenyl]-3-carboxylate (4e)

Synthesized using the procedure for 4a except using 4-((naphthalen-1-yloxy)methyl) phenylboronic acid as the starting material, which afforded the title compound (626 mg, 82%) as a yellow oil which solidified upon standing.
¹H NMR (400 MHz, CDCl₃) δ 8.36 (d, J=4.0 Hz, 1H), 8.14 (s, 1H), 7.80-7.34 (m, 10H), 6.89 (d, J=4.0 Hz, 1H), 6.71 (d, J=8.0 Hz, 1H), 5.77 (s, 2H), 5.24 (s, 2H), 3.88 (s, 3H); ¹³C NMR (100 MHz, CDCl₃) δ 168.48, 154.48, 149.77, 140.04, 135.26, 134.52, 132.72, 129.47, 128.84, 127.87, 127.43, 126.40, 126.33, 125.80, 125.75, 125.19, 122.17, 120.45, 117.21, 110.91, 105.19, 69.89, 51.58.

methyl 4'-((naphthalen-1-yloxy)methyl)-4-(naphthalene-2-sulfonamido)-[1,1'-biphenyl]-3-carboxylate (5e)

Synthesized using the procedure for 3k except using 4c as the starting material, which afforded the title compound (288 mg, 84%) as a yellow oil.

¹H NMR (400 MHz, CDCl₃) δ 10.78 (s, 1H), 8.49 (s, 1H), 8.33-8.31 (m, 1H), 8.13 (d, J=4.0 Hz, 1H), 7.94-7.24 (m, 17H), 6.86 (d, J=8.0 Hz, 1H), 5.25 (s, 2H), 3.86 (s, 3H); ¹³C NMR (100 MHz, CDCl₃) δ 168.23, 154.34, 139.51, 138.72, 136.60, 136.30, 135.48, 134.94, 134.53, 132.90, 131.97, 129.48, 129.29, 128.96, 128.90, 127.88, 127.85, 127.55, 127.46, 126.84, 126.43, 125.75, 125.70, 125.23, 122.21, 122.06, 120.58, 119.43, 116.21, 105.20, 69.67, 52.53.

4'-((naphthalen-1-yloxy)methyl)-4-(naphthalene-2-sulfonamido)-[1,1'-biphenyl]-3-carboxylic acid (475)

Synthesized using the procedure for 416 except using 5d as the starting material, which afforded the title compound (103 mg, 74%) as a yellow oil which solidified upon standing.
¹H NMR (400 MHz, DMSO) δ 11.35 (br, 1H), 8.66 (s, 1H), 8.20-7.39 (m, 19H), 7.06 (d, J=8.0 Hz, 1H), 5.32 (s, 2H); ¹³C NMR (100 MHz, DMSO) δ 170.12, 154.11, 139.47, 138.22, 137.08, 136.20, 135.03, 134.97, 134.54, 132.94, 132.06, 130.34, 129.87, 129.83, 129.67, 129.07, 128.61, 128.35, 127.96, 126.95, 126.61, 125.87, 125.49, 122.24, 121.97, 120.65, 119.38, 117.81, 106.27, 69.52.
HRMS (ESI) m/z cacld for $C_{34}H_{25}NO_5S$ [M+H]⁺: 560.1526. Found: 560.1506.

methyl 2-amino-4-isopropyl-5-(phenethylthio)benzoate (2b)

Synthesized using the procedure for 2 except using methyl 2-amino-5-iodo-4-isopropylbenzoate (1 R3=isopropyl) as the starting material, which afforded the desired compound (188 mg, 81%) as a yellow oil.
¹H NMR (400 MHz, CDCl₃) δ 8.55 (s, 2H), 7.99 (s, 1H), 7.31-7.18 (m, 5H), 6.91 (s, 1H), 3.91 (s, 3H), 3.52-3.46 (m, 1H), 3.07 (t, J=8.0 Hz), 2.90 (t, J=8.0 Hz, 2H), 1.20 (d, J=8.0 Hz, 6H); ¹³C NMR (100 MHz, CDCl₃) δ 167.74, 156.85, 142.24, 140.10, 134.08, 128.50, 128.47, 127.22, 126.46, 117.12, 113.27, 52.22, 36.62, 35.51, 30.61, 22.93.

methyl 4-isopropyl-2-(naphthalene-2-sulfonamido)-5-(phenethylthio)benzoate (3t)

Synthesized using the procedure for 3k except using 2b as the starting material, which afforded the title compound (164 mg, 89%) as a yellow oil.
¹H NMR (400 MHz, CDCl₃) δ 10.61 (s, 1H), 8.46 (s, 1H), 7.90-7.08 (m, 13H), 3.84 (s, 3H), 3.43-3.36 (m, 1H), 3.00 (t, J=8.0 Hz, 2H), 2.80 (t, J=8.0 Hz, 2H), 1.18 (d, J=8.0 Hz, 6H); ¹³C NMR (100 MHz, CDCl₃) δ 167.80, 156.23, 139.89, 138.94, 135.95, 134.92, 132.42, 131.86, 129.39, 129.27, 129.13, 129.06, 128.96, 128.48, 128.41, 127.87, 127.60, 126.48, 122.33, 116.32, 113.99, 52.40, 35.86, 35.41, 30.82, 22.96.

4-isopropyl-2-(naphthalene-2-sulfonamido)-5-(phenethylthio)benzoic acid (478)

Synthesized using the procedure for 416 and 3t as the starting material, which afforded the desired compound (90 mg, 98%) as a tan solid powder after HPLC purification. HPLC ($t_R$=26.21 min), purity >99%.
¹H NMR (400 MHz, CDCl₃) δ 10.34 (s, 1H), 8.49 (s, 1H), 7.93-7.12 (m, 13H), 3.42-3.35 (m, 1H), 3.07 (d, J=8.0 Hz, 2H), 2.85 (d, J=8.0 Hz, 2H), 1.19 (d, J=8.0 Hz, 6H); ¹³C NMR (125 MHz, CDCl₃) δ 171.81, 157.07, 139.71, 139.24, 135.66, 134.96, 132.62, 131.83, 129.66, 129.60, 129.42, 129.10, 128.51, 128.42, 127.89, 127.70, 126.52, 122.15, 116.04, 112.74, 35.55, 35.26, 30.88, 22.84.

HRMS (ESI) m/z cacld for $C_{28}H_{27}NO_4S_2[M+H]^+$: 506.1454. Found: 506.1451.

methyl 4-isopropyl-5-(phenethylthio)-2-(4-phenoxyphenylsulfonamido)benzoate (3u)

Synthesized using the procedure for 3p except using 2b as the starting material, which afforded the title compound (55 mg, 54%) as a yellow oil.

$^1$H NMR (400 MHz, CDCl$_3$) δ 10.46 (s, 1H), 7.88 (s, 1H), 7.81-7.77 (m, 2H), 7.59 (s, 1H), 7.38-6.93 (m, 12H), 3.88 (s, 3H), 3.47-3.40 (m, 1H), 3.07 (t, J=8.0 Hz, 2H), 2.87 (t, J=8.0 Hz, 2H), 1.18 (d, J=8.0 Hz, 6H); $^{13}$C NMR (100 MHz, CDCl$_3$) δ 167.77, 161.83, 156.23, 154.99, 139.91, 139.03, 132.73, 132.39, 130.13, 129.70, 129.04, 128.53, 128.44, 126.54, 124.96, 120.20, 117.42, 116.43, 114.04, 52.43, 35.92, 35.43, 30.84, 22.95.

4-isopropyl-5-(phenethylthio)-2-(4-phenoxyphenylsulfonamido)benzoic acid (476)

Synthesized using the procedure for 416 except using 3u as the starting material, which afforded the title compound (27 mg, 61%) as a yellow oil which solidified upon standing.

$^1$H NMR (400 MHz, CDCl$_3$) δ 10.23 (s, 1H), 7.97 (s, 1H), 7.81 (d, J=8.0 Hz, 2H), 7.60 (s, 1H), 7.38-6.94 (m, 12H), 3.46-3.39 (m, 1H), 3.11 (d, J=8.0 Hz, 2H), 2.90 (d, J=8.0 Hz, 2H), 1.19 (d, J=8.0 Hz, 6H); $^{13}$C NMR (100 MHz, CDCl$_3$) δ 170.89, 162.01, 156.99, 154.88, 139.78, 139.37, 132.66, 132.43, 130.16, 129.74, 129.55, 128.56, 128.45, 126.57, 125.03, 120.27, 117.46, 116.20, 112.87, 35.66, 35.31, 30.91, 22.86.

HRMS (ESI) m/z cacld for $C_{30}H_{29}NO_5S_2[M+H]^+$: 548.1560. Found: 548.1554.

methyl 4-amino-6-isopropyl-4'-((3-(trifluoromethyl)phenoxy)methyl)-[1,1'-biphenyl]-3-carboxylate (4f)

Synthesized using the procedure for 4c except using methyl 2-amino-5-iodo-4-isopropylbenzoate (1 R3=isopropyl) as the starting material, which afforded the title compound (180 mg, 68%) as a yellow oil.

$^1$H NMR (400 MHz, CDCl$_3$) δ 7.69 (s, 1H), 7.46-7.16 (m, 8H), 6.65 (s, 1H), 5.52 (s, 2H), 5.13 (s, 2H), 3.83 (s, 3H), 3.05-2.98 (m, 1H), 1.13 (d, J=8.0 Hz, 6H); $^{13}$C NMR (100 MHz, CDCl$_3$) δ 168.37, 158.91, 153.37, 141.42, 134.41, 132.56, 132.05, 131.73, 130.01, 129.87, 127.36, 125.30, 122.59, 118.28, 117.68, 117.64, 113.46, 111.74, 111.70, 108.69, 70.19, 51.39, 29.54, 23.80.

methyl 6-isopropyl-4-(naphthalene-2-sulfonamido)-4'-((3-(trifluoromethyl)phenoxy)methyl)-[1,1'-biphenyl]-3-carboxylate (482)

Synthesized using the procedure for 5c except using 4f as the starting material, which afforded the title compound (170 mg, 98%) as a yellow oil.

$^1$H NMR (400 MHz, CDCl$_3$) δ 10.77 (s, 1H), 8.52 (s, 1H), 7.93-7.14 (m, 16H), 5.10 (s, 2H), 3.81 (s, 3H), 3.02-2.95 (m, 1H), 1.12 (d, J=8.0 Hz, 6H); $^{13}$C NMR (100 MHz, CDCl$_3$) δ 168.23, 158.77, 153.96, 140.08, 139.66, 136.00, 135.52, 135.19, 134.97, 132.55, 132.06, 131.91, 131.73, 130.04, 129.53, 129.48, 129.30, 129.14, 128.99, 127.89, 127.61, 127.42, 125.25, 122.55, 122.37, 118.24, 117.77, 117.73, 115.89, 112.99, 111.71, 111.67, 69.99, 52.99, 29.98, 23.70.

HRMS (ESI) m/z cacld for $C_{35}H_{30}F_3NO_5S [M+H]^+$: 634.1870. Found: 634.1867.

6-isopropyl-4-(naphthalene-2-sulfonamido)-4'-((3-(trifluoromethyl)phenoxy)methyl)-[1,1'-biphenyl]-3-carboxylic acid (474)

Synthesized using the procedure for 416 except using 5f as the starting material, which afforded the title compound (92 mg, 78%) as a yellow oil which solidified upon standing.

$^1$H NMR (400 MHz, CDCl$_3$) δ 10.32 (s, 1H), 7.88-6.97 (m, 17H), 5.14 (s, 2H), 3.08-3.02 (m, 1H), 1.11 (d, J=8.0 Hz, 6H); $^{13}$C NMR (125 MHz, CDCl$_3$) δ 172.02, 158.77, 155.35, 140.26, 139.73, 135.92, 135.73, 135.34, 135.01, 133.58, 132.04, 131.85 (q, J=32.5 Hz), 92, 131.78, 130.05, 129.64, 129.54, 129.40, 129.15, 129.08, 127.93, 127.70, 127.49, 123.91 (q, J=271.25 Hz), 122.27, 118.24, 117.77 (q, J=3.75 Hz), 115.86, 111.70 (q, J=3.75 Hz), 69.98, 30.09, 23.71.

HRMS (ESI) m/z cacld for $C_{34}H_{28}F3NO_5S [M+H]^+$: 620.1713. Found: 620.1704.

methyl 6-isopropyl-4-(4-phenoxyphenylsulfonamido)-4'-((3-(trifluoromethyl)phenoxy)methyl)-[1,1'-biphenyl]-3-carboxylate (5g)

Synthesized using the procedure for 3u except using 4f as the starting material, which afforded the title compound (48 mg, 96%) as a yellow oil.

$^1$H NMR (400 MHz, CDCl$_3$) δ 10.61 (s, 1H), 7.88-7.84 (m, 2H), 7.75 (s, 1H), 7.67 (s, 1H), 7.48-6.97 (m, 15H), 5.13 (s, 2H), 3.85 (s, 3H), 3.05-2.98 (m, 1H), 1.11 (d, J=8.0 Hz, 6H); $^{13}$C NMR (100 MHz, CDCl$_3$) δ 168.19, 161.87, 158.79, 155.06, 153.98, 140.15, 139.76, 135.52, 135.26, 132.87, 132.56, 130.15, 130.06, 129.76, 129.58, 127.49, 124.97, 120.18, 118.28, 117.76, 117.55, 116.07, 113.09, 111.72, 111.68, 70.02, 52.33, 30.00, 23.72.

6-isopropyl-4-(4-phenoxyphenylsulfonamido)-4'-((3-(trifluoromethyl)phenoxy)methyl)-[1,1'-biphenyl]-3-carboxylic acid (477)

Synthesized using the procedure for 416 except using 5g as the starting material, which afforded the title compound (27 mg, 58%) as a white solid powder after HPLC purification. HPLC (t$_R$=28.03 min), purity >99%.

$^1$H NMR (400 MHz, CDCl$_3$) δ 10.48 (s, 1H), 8.54 (s, 1H), 7.93-7.14 (m, 18H), 5.11 (s, 2H), 3.02-2.97 (m, 1H), 1.11 (d, J=8.0 Hz, 6H); $^{13}$C NMR (100 MHz, CDCl$_3$) δ 171.65, 158.78, 155.19, 140.23, 139.77, 135.92, 135.65, 135.32, 135.00, 133.52, 132.08, 131.92, 131.76, 130.17, 130.05, 129.63, 129.54, 129.41, 129.16, 129.06, 127.92, 127.67, 127.47, 125.26, 122.55, 122.29, 118.25, 117.78, 117.75, 115.77, 111.72, 111.68, 69.99, 30.06, 23.69.

HRMS (ESI) m/z cacld for $C_{36}H_{30}F_3NO_6S [M+H]^+$: 662.1819. Found: 662.1803.

methyl 4-(4-(4-fluorophenoxy)phenylsulfonamido)-6-isopropyl-4'-((3-(trifluoromethyl)phenoxy)methyl)-[1,1'-biphenyl]-3-carboxylate (481)

Synthesized using the procedure for 5g except using 4-(4-fluorophenoxy)benzene-1-sulfonyl chloride as the starting material, which afforded the title compound (83 mg, 67%) as a yellow oil.

¹H NMR (400 MHz, CDCl₃) δ 10.61 (s, 1H), 7.86 (d, J=8.0 Hz, 2H), 7.75 (s, 1H), 7.68 (s, 1H), 7.48-6.94 (m, 14H), 5.13 (s, 2H), 3.85 (s, 3H), 3.05-2.98 (m, 1H), 1.11 (d, J=8.0 Hz, 6H); ¹³C NMR (100 MHz, CDCl₃) δ 168.14, 161.95, 160.91, 158.80, 158.48, 153.95, 150.81, 150.78, 140.14, 139.83, 135.45, 135.28, 133.17, 132.54, 132.09, 131.77, 130.06, 129.80, 129.57, 127.49, 125.26, 122.55, 121.84, 121.75, 118.28, 117.83, 117.79, 117.76, 117.72, 117.13, 116.94, 116.70, 116.08, 115.99, 113.03, 111.74, 111.70, 111.66, 69.99, 52.31, 30.00, 23.73.

HRMS (ESI) m/z cacld for $C_{37}H_{31}F4NO_6S$ [M+H]⁺: 694.1881. Found: 694.1876.

4-(4-(4-fluorophenoxy)phenylsulfonamido)-6-isopropyl-4'-((3-(trifluoromethyl)phenoxy)methyl)-[1,1'-biphenyl]-3-carboxylic acid (480)

Synthesized using the procedure for 416 except using 5h as the starting material, which afforded the title compound (45 mg, 77%) % as a yellow solid powder after HPLC purification. HPLC ($t_R$=27.97 min), purity 97%.

¹H NMR (400 MHz, CDCl₃) δ 10.32 (s, 1H), 7.88-6.94 (m, 18H), 5.14 (s, 2H), 3.09-3.02 (m, 1H), 1.13 (d, J=8.0 Hz, 6H); ¹³C NMR (100 MHz, CDCl₃) δ 171.19, 162.15, 160.95, 158.79, 158.52, 155.32, 150.70, 150.67, 140.34, 139.77, 135.76, 135.44, 133.50, 132.89, 132.11, 131.79, 130.08, 129.82, 129.56, 127.55, 127.37, 125.27, 122.56, 121.92, 121.83, 118.29, 117.83, 117.79, 117.16, 116.97, 116.74, 116.12, 111.73, 111.69, 69.99, 30.11, 23.72.

HRMS (ESI) m/z cacld for $C_{36}H_{29}F4NO_6S$ [M+H]⁺: 680.1724. Found: 680.1710.

methyl 6-isopropyl-4-(4-phenoxybenzamido)-4'-((3-(trifluoromethyl)phenoxy)methyl)-[1,1'-biphenyl]-3-carboxylate (486)

To a round-bottom-flask under nitrogen 4-phenoxybenzoic acid (143 mg, 0.668 mmol, 2.0 equiv.), dry CH₂Cl₂ (20 mL) and SOCl₂ (0.243 mL, 398 mg, 3.34 mmol, 10.0 equiv.) were added. The mixture was heated at 40° C. for 2 hours and the solvent and excess SOCl₂ were removed under reduced pressure. The residue was re dissolved in dry CH₂Cl₂ (20 mL). 4f (148 mg, 0.334 mmol, 1.0 equiv.) and K₂CO₃ (231 mg, 1.67 mmol, 5.0 equiv.) were added and the mixture was stirred at room temperature for 16 hours. H₂O (20 mL) was added to the reaction mixture and extracted with CH₂Cl₂ (2×20 mL). All the organic extractions were combined, dried over NaSO₄ and concentrated under reduced pressure. The crude product was purified by flash column chromatography (ethyl acetate:hexanes=20:80) on silica gel to afford 486 (181 mg, 85%) as a yellow oil.

¹H NMR (400 MHz, CDCl₃) δ 12.06 (s, 1H), 8.99 (s, 1H), 8.06-8.03 (m, 2H), 7.92 (s, 1H), 7.51-7.08 (m, 15H), 5.15 (s, 2H), 3.91 (s, 3H), 3.15-3.08 (m, 1H), 1.24 (d, J=8.0 Hz, 6H); ¹³C NMR (100 MHz, CDCl₃) δ 169.00, 165.67, 161.25, 158.85, 155.69, 154.42, 141.23, 140.71, 135.47, 135.12, 132.36, 132.09, 131.77, 130.05, 130.02, 129.69, 129.42, 128.87, 127.49, 125.29, 124.48, 120.14, 118.28, 117.81, 117.72, 112.69, 111.73, 111.69, 70.07, 52.35, 30.29, 23.79.

HRMS (ESI) m/z cacld for $C_{38}H_{32}F3NO_5$ [M+H]⁺: 640.2305. Found: 640.2303.

6-isopropyl-4-(4-phenoxybenzamido)-4'-((3-(trifluoromethyl)phenoxy)methyl)-[1,1'-biphenyl]-3-carboxylic acid (483)

Synthesized using the procedure for 416 and 5i as the starting material, which afforded the desired compound (87 mg, 86%) as a white solid powder after HPLC purification. HPLC ($t_R$=29.19 min), purity >99%.

¹H NMR (400 MHz, CDCl₃) δ 11.77 (s, 1H), 9.04 (s, 1H), 8.01 (d, J=8.0 Hz, 3H), 7.53-7.07 (m, 15H), 5.16 (s, 2H), 3.16-3.09 (m, 1H), 1.25 (d, J=8.0 Hz, 6H); ¹³C NMR (100 MHz, CDCl₃) δ 171.97, 165.40, 161.14, 158.85, 155.72, 155.64, 141.99, 140.49, 135.54, 135.21, 133.20, 132.43, 132.11, 131.79, 131.47, 130.07, 130.00, 129.71, 129.35, 129.02, 127.55, 125.29, 124.43, 122.58, 120.01, 118.28, 117.93, 117.89, 117.80, 117.76, 111.77, 111.73, 111.69, 111.40, 70.08, 30.39, 23.80.

HRMS (ESI) m/z cacld for $C_{37}H_{30}F3NO_5$ [M+H]⁺: 662.1819. Found: 662.1803.

methyl 4-(4-(4-fluorophenoxy)benzamido)-6-isopropyl-4'-((3-(trifluoromethyl)phenoxy)methyl)-[1,1'-biphenyl]-3-carboxylate (5j)

Synthesized using the procedure for 5i except using 4-(4-fluorophenoxy)benzoic acid as the starting material, which afforded the title compound (79 mg, 75%) as a yellow oil.

¹H NMR (400 MHz, CDCl₃) δ 12.02 (s, 1H), 9.02 (s, 1H), 8.07-8.04 (m, 2H), 7.92 (s, 1H), 7.51-7.08 (m, 14H), 5.15 (s, 2H), 3.91 (s, 3H), 3.17-3.06 (m, 1H), 1.24 (d, J=8.0 Hz, 6H); ¹³C NMR (100 MHz, CDCl₃) δ 169.01, 165.21, 161.31, 160.67, 158.85, 158.26, 154.39, 151.48, 151.45, 141.42, 140.75, 135.31, 135.10, 132.34, 132.09, 131.77, 131.45, 130.05, 129.70, 129.42, 129.17, 127.49, 125.29, 122.58, 121.75, 121.67, 118.28, 117.76, 117.72, 117.70, 117.35, 116.74, 116.51, 112.56, 111.77, 111.73, 111.69, 111.65, 70.08, 52.33, 30.29, 23.83.

4-(4-(4-fluorophenoxy)benzamido)-6-isopropyl-4'-((3-(trifluoromethyl)phenoxy)methyl)-[1,1'-biphenyl]-3-carboxylic acid (487)

Synthesized using the procedure for 416 and 5j as the starting material, affording the desired compound (40 mg, 78%) as a white solid powder after HPLC purification. HPLC ($t_R$=29.26 min), purity >99%.

¹H NMR (400 MHz, CDCl₃) δ 11.78 (s, 1H), 9.04 (s, 1H), 8.02-7.99 (m, 3H), 7.53-7.03 (m, 14H), 5.16 (s, 2H), 3.16-3.09 (m, 1H), 1.25 (d, J=8.0 Hz, 6H); ¹³C NMR (125 MHz, CDCl₃) δ 170.61, 165.28, 165.20, 161.15, 160.34, 158.78, 158.41, 154.26, 151.44 (d, J=2.5 Hz), 141.41, 140.73, 135.23, 134.95, 132.99, 131.84 (q, J=31.25 Hz), 130.01, 129.67, 129.38, 129.17, 127.41, 123.89 (q, J=271.25 Hz), 121.56 (d, J=8.75 Hz), 118.23, 117.67 (q, J=3.75 Hz), 117.50, 117.45, 117.27, 116.65, 116.46, 112.69, 111.67 (q, J=3.75 Hz), 70.06, 30.20, 23.78.

HRMS (ESI) m/z cacld for $C_{37}H_{29}F4NO_5$ [M+H]⁺: 644.2055. Found: 644.2048.

Example II

This example describes de-novo and SAR studies.

The de-novo design was based on a validated hit compound E238

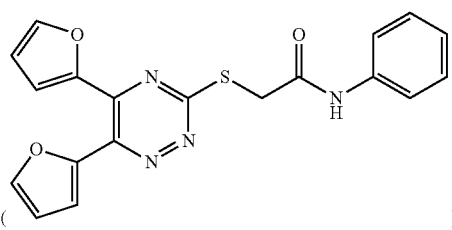

with 5,6-difuran-2-yl-1,2,4-triazine core identified with high throughput screening (see, e.g., Du, Y., et al., Assay and drug development technologies 9, 382-393). The hit compound E238 (FIG. 1), was resynthesized and its binding to Mcl-1 was confirmed with a $K_i$ value of 2.09±0.18 µM in the FP assay using Bid BH3 peptide as a probe. The direct and specific binding of E238 to Mcl-1 protein was confirmed with HSQC NMR spectroscopy and the obtained HSQC spectra showed concentration-dependent perturbations of residues backbone amides (FIG. 1). Overall analysis of the chemical shift changes of the compound E238 in complex with Mcl-1 showed that E238 affects the residues forming the BH3-binding groove and provided conclusive evidence that it binds Mcl-1 protein at the same site where the conserved BH3 peptides interact with Mcl-1 protein. These results also confirmed the predicted binding model of E238 to Mcl-1 obtained by using reported complex structure of inhibitor and Mcl-1: PDB: 4HW2. This model revealed that the compound forms a hydrogen bond between the oxygen atom of one furan ring and Arg 263 residue of the protein of Mcl-1, mimicking the conserved aspartate in pro-apoptotic proteins. The second furan ring has weak hydrophobic interaction with residues Phe 318 and Phe 319, which are located proximal to the conserved h4 pocket (FIG. 1). These two residues were identified that contribute to additional hydrophobic contacts with the staple of a reported stabilized α-helix (see, e.g., Stewart, M. L., et al., Nat Chem Biol 6, 595-601). The sulfur-amide chain does not have direct interactions with the Mcl-1 protein, playing the role of a linker and directing the distal phenyl ring of E238 into the hydrophobic pocket 2 (h2), mimicking the conserved hydrophobic residues in the BH3 binding motif of many different BH3 peptides.

In order to optimize these interactions and extend the molecule towards the h4 hydrophobic pocket, compound 368

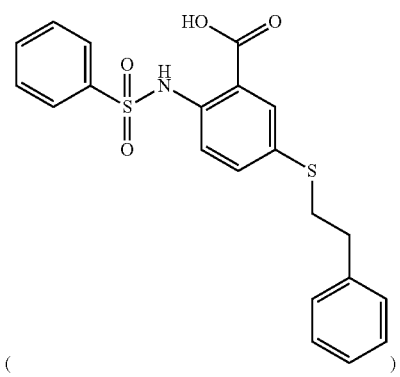 [SMILES: O=C(O)c1cc(SCCc2ccccc2)ccc1NS(=O)(=O)c1ccccc1]

( )

was de-novo designed (FIG. 1). In the 368, one furan ring was replaced with carboxylate moiety in order to improve the conserved hydrogen bond, the other furan ring was replaced with phenylsulfonamido and the side chain was changed to phenethylthio substituent in order to allow further modification for improving hydrophobic interactions. Interestingly this compound binds to Mcl-1 with improved binding affinity with $K_i$=0.490±0.01 µM, and showed large chemical shift perturbations in 15N-HSQC NMR spectrum indicative of robust binding (FIG. 1). Based on this finding extensive medicinal chemistry efforts were applied to systematically modify 368 and developed a series of compounds with significantly improved binding affinity against Mcl-1 protein (Table 1).

TABLE 1

Binding affinity of Mcl-1 inhibitors using FP based assay

| Cpd # | $K_i$ [µM] |
|---|---|
| 416 | 1.451 ± 0.132 |
| 364 | 0.891 ± 0.185 |
| 368 | 0.490 ± 0.088 |
| 702 | 2.364 ± 0.116 |
| 392 | 0.993 ± 0.178 |
| 455 | >2 |
| 404 | 5.741 ± 0.749 |
| 386 | 0.381 ± 0.066 |
| 398 | 0.241 ± 0.089 |
| 443 | 0.343 ± 0.033 |
| 454 | 0.874 ± 0.246 |
| 382 | 0.158 ± 0.023 |
| 378 | 0.048 ± 0.012 |
| 458 | 0.079 ± 0.025 |
| 418 | 0.031 ± 0.010 |
| 380 | 0.031 ± 0.007 |
| 376 | 0.044 ± 0.014 |
| 396 | 0.200 ± 0.030 |
| 456 | 0.387 ± 0.138 |
| 414 | 0.275 ± 0.021 |
| 462 | 0.495 ± 0.172 |
| 453 | >2 |
| 460 | >2 |
| 466 | 0.094 ± 0.017 |
| 467 | 1.160 ± 0.196 |
| 468 | 0.050 ± 0.011 |
| 469 | 2.357 ± 0.080 |
| 471 | 0.036 ± 0.006 |
| 473 | 0.031 ± 0.009 |
| 475 | 0.027 ± 0.005 |
| 478 | 0.070 ± 0.021 |
| 474 | 0.023 ± 0.003 |
| 476 | 0.035 ± 0.013 |
| 477 | 0.013 ± 0.003 |
| 480 | 0.010 ± 0.003 |
| 483 | 0.007 ± 0.002 |
| 487 | 0.008 ± 0.002 |
| 481 | >2 |
| 482 | >2 |
| 460 | >2 |
| 486 | >2 |
| 395 | >2 |
| 410 | 0.233 ± 0.021 |
| 429 | 2.236 ± 0.431 |
| 435 | 0.245 ± 0.048 |
| 479 | 0.066 ± 0.027 |
| 484 | 0.042 ± 0.017 |
| 485 | 0.437 ± 0.067 |

As such, a first goal was to optimize the R1 substituent which based on modeling studies was projecting towards the h2 hydrophobic pocket, which is bigger and deeper than the other hydrophobic pockets in the BH3 binding groove of Mcl-1. By applying structural based analysis, we were able to improve the binding potency by 16 fold with compound 380

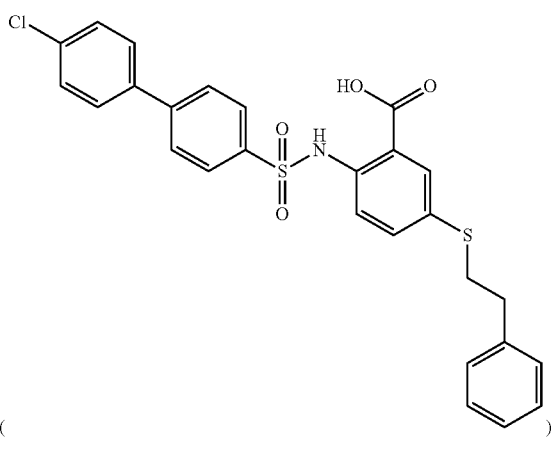 [SMILES: O=C(O)c1cc(SCCc2ccccc2)ccc1NS(=O)(=O)c1ccc(-c2ccc(Cl)cc2)cc1]

with $K_i$ of 31 nM (Table 1). The importance of the phenethylthio substituent was confirmed with compound 460

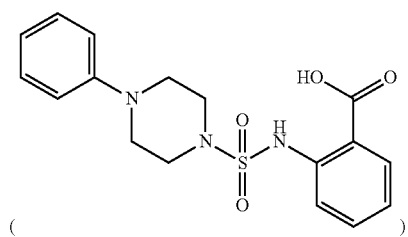 [SMILES: O=C(O)c1ccccc1NS(=O)(=O)N1CCN(c2ccccc2)CC1]

where this substituent was removed producing a deleterious to Mcl-1 binding.

Example III

This example describes crystallographic studies.

In order to better understand the key binding elements for this series of compounds and progress these inhibitors, co-crystal structures of 382

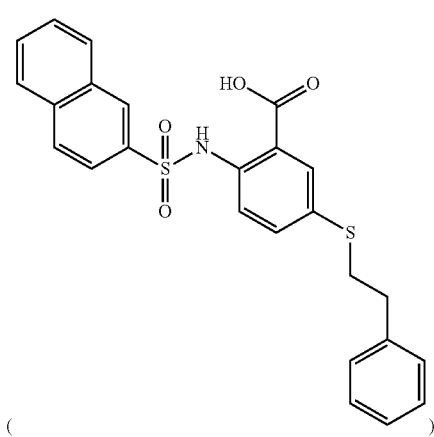 [SMILES: O=C(O)c1cc(SCCc2ccccc2)ccc1NS(=O)(=O)c1ccc2ccccc2c1]

and 396

Figure 2A:
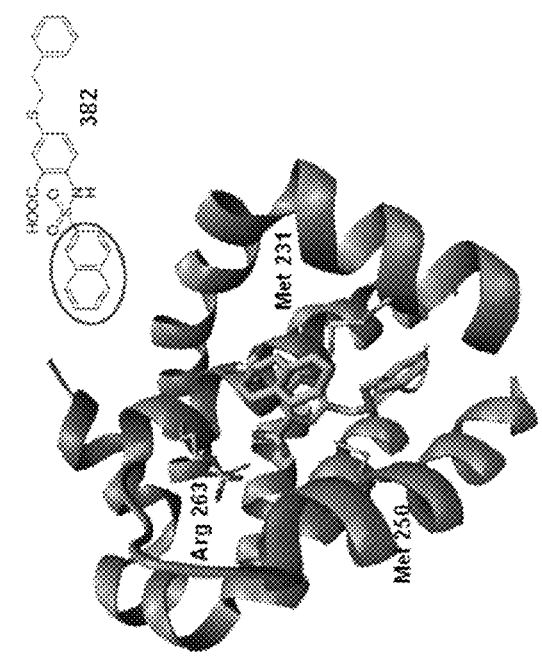
FIG. 2A-B: Crystal structures of the Mcl-1 with the bound (A) 396 and (B) 382. These inhibitors are bound to the Mcl-1 BH3 binding site in a flipped folded conformation where the interaction between the carboxylic group and Arg263 is the anchor point.
Figure 2B:
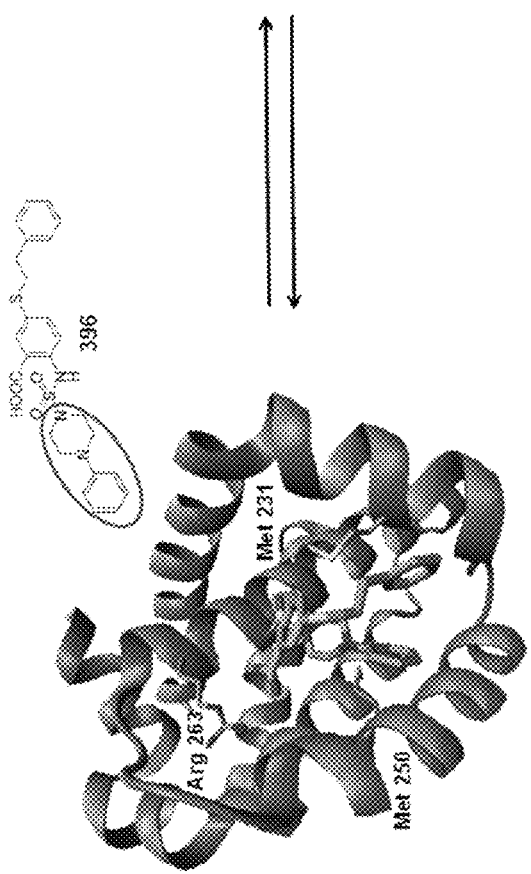

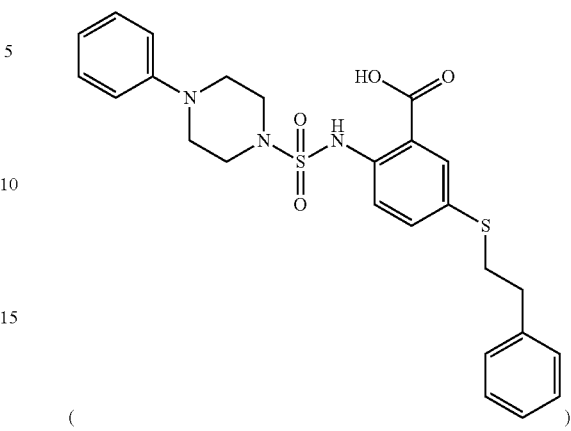

bound to Mcl-1 were obtained at 2.75 and 2.54 Å respectively (FIG. 2). As expected the acid moiety of both ligands interacts with Arg 263 of Mcl-1 and mimics the hydrogen bond interaction with conserved Asp of the pro-apoptotic proteins Bim and Noxa. However, interestingly the overall orientation of these ligands is different. The S-substituted ethylthiobenzene moiety from 382 is buried inside the h2 pocket interacting with the hydrophobic side chains of the Mcl-1 α3 helix and sulfur-containing side chain of Met 250, similarly as in the docking predictions for the 368 compound. (FIG. 2). The compound's R1 naphthalene moiety is placed in the vicinity of the Mcl-1 h3 binding pocket. In contrast 396 is bound to the Mcl-1 BH3 binding site in a flipped folded conformation. The 396 R1 phenylpiperazine-sulfonamido substituent is placed in the Mcl-1 h2 binding pocket and the phenyl moiety interacts with the side chains of Val 249, Val 253 and Leu 235 through hydrophobic interactions. The R2 S-substituted ethylbenzene moiety is dissimilar to the 382 Mcl-1 complex located on top of the Mcl-1 α3 helix and to some extend interacts with the sulfur-containing side chain of Met 231 as well as side chain of Leu 235 (FIG. 2). This folded conformation of 396 is stabilized by the π-π stacking of the two distal phenyl groups. These structural findings and SAR studies indicate that the binding mode depends on the particular substitution pattern.

Example IV

Figure 3:
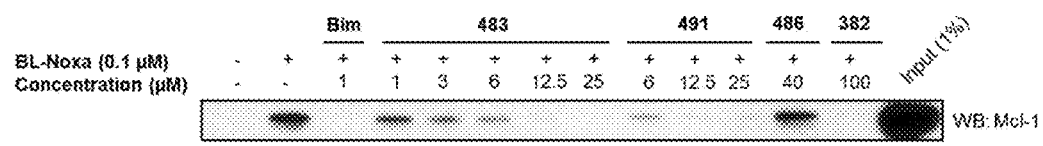
FIG. 3: Mcl-1 inhibitors recognize and bind endogenous Mcl-1 protein. Biotin-labeled Noxa (BL-Noxa, 0. µM) was incubated with whole cell lysates of 2LMP cells with or without tested Mcl-1 inhibitors and Bim BH3 peptide as a positive control, followed by incubation with precleared streptavidin agarose beads. Eluted beads were subjected to Western blot analysis with anti-Mcl-1 antibody.

This example demonstrates the specific binding of novel inhibitors to endogenous Mcl-1 protein (FIG. 3), by employing a pull-down assay using biotin-labeled Noxa (BL-Noxa) and whole cell lysate from the human breast cancer cell line 2LMP. As shown in FIG. 3, Mcl-1 was pulled down by BL-Noxa and, as was expected, the Bim BH3 peptide disrupted the interaction between BL-Noxa and Mcl-1. Preincubation with Mcl-1 inhibitors, 483, and 491, dose-dependent blocked the binding of BL-Noxa to Mcl-1, demonstrating that these inhibitors can recognize and specifically bind to the BH3 binding groove of endogenous Mcl-1 protein.

Example V

This example describes structure-based optimization of the LM series. Encouraged by the initial inhibition properties of the LM series of compounds further optimization of their potency was conducted. The crystal structures were analyzed and compared with several reported complex structures of small molecule Mcl-1 inhibitors. Based on this analysis it was decided to take 382 as a starting point for further optimization of the R2 substituent. The most potent inhibitor 475

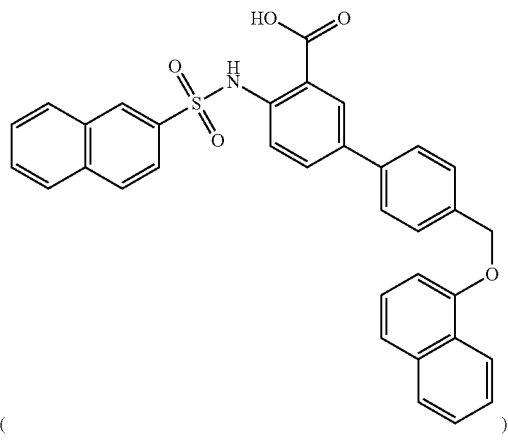 [SMILES: O=C(O)c1cc(-c2ccc(COc3cccc4ccccc34)cc2)ccc1NS(=O)(=O)c1ccc2ccccc2c1]

exhibited the inhibition activity of 27±5.0 nM, 6 fold improvement in comparison with 382.

Furthermore, from the structural-based analysis of the 382 complex structure, it was determined that 382 could be further optimized by introducing an additional lipophilic substituent at its R3 position on the phenyl carboxylic core. This new substituent was aimed to interact with the vacant part of the h3 Mcl-1 pocket and form hydrophobic interactions with the Phe 228, Phe 270 and Met 231 residues. This h3 accommodation is possible due to the slight side chain movement of Met 231, which was observed experimentally when larger moieties were occupying this pocket. To verify this structure-based hypothesis 478

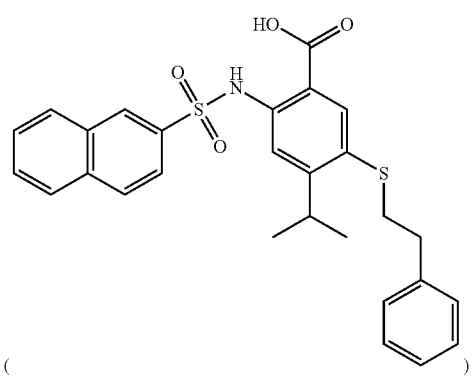 [SMILES: CC(C)c1cc(NS(=O)(=O)c2ccc3ccccc3c2)c(C(=O)O)cc1SCCc1ccccc1]

was synthesized where iso-propyl group was introduced at the R3 position and showed a 2.5 fold improvement over the 382 compound. By further variation of the substituents at the R2 position and a subsequent replacement of the R1 naphthalene moiety of 382 with phenoxyphenyl moiety, the most potent compound 483

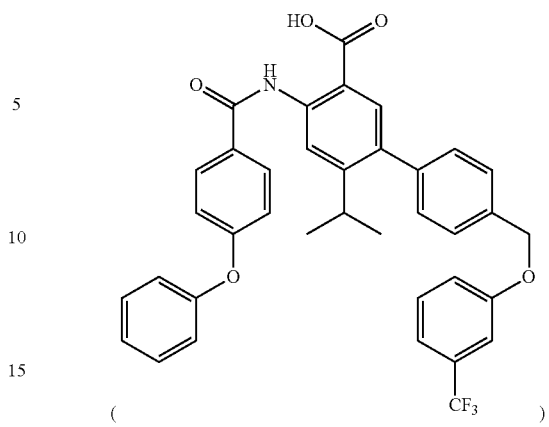

of this series was obtained with binding affinity of Ki=7.0±2.0 nM to Mcl-1, and high selectivity towards Bcl-2, Bcl-xL and Bcl-w (Ki>1,000 nM).

Example VI

This example demonstrates that 483 and 487 antagonize Mcl-1 function.

Figure 4:
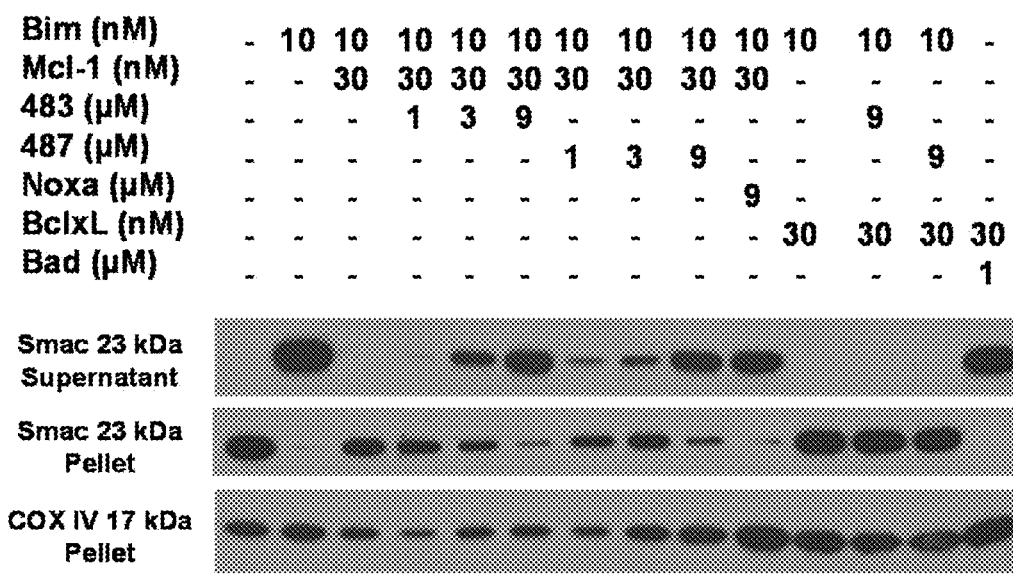
FIG. 4: 483 and 487 antagonize the function of Mcl-1 but not Bcl-xL resulting in triggering the release of Smac.

To provide direct evidence that 483 and 487 also selectively antagonize Mcl-1 function, a cell-free functional assay was established using purified mitochondria, recombinant Mcl-1 and Bcl-xL proteins, and the BIM BH3 peptide which binds to both proteins with high affinities. At 10 nM the BIM BH3 peptide induces substantial release of Smac protein from mitochondria, and 30 nM of Mcl-1 and Bcl-xL completely inhibit this release (FIG. 4). 483 and 487 antagonize Mcl-1 and restore BIM-induced release of Smac protein from mitochondria in dose dependent manner starting from 1 μM, and at 9 μM their efficacy is in a similar level as Noxa BH3 peptide at 9 μM. Consistent with 483 and 487 selectivity binding profile, in the Bcl-xL functional assay both compounds fail to release Smac at concentrations as high as 9 μM. These data show that 483 and 487, function as potent selective antagonists of Mcl-1 protein in a similar manner as Noxa.

Example VII

This example demonstrates that 483 has on-target cellular activity.

Wild-type, Bax/Bak double knockout and Mcl-1 knockout MEFs cells have been employed as models to establish the mechanism-based apoptosis and on-target activity (see, e.g., Lindsten, T., and Thompson, C. B. (2006) Cell death and differentiation 13, 1272-1276). 483 primarily causes cell death in wild-type MEFs and didn't show cytotoxicity against Bax/Bak and Mcl-1 knockout MEFs cells. As was expected ABT-263 showed increased growth-inhibitory activity in the Mcl-1−/− cells (FIG. 5A). These results demonstrate that 483 have on-target activity and did not kill murine embryonic fibroblasts lacking the apoptosis effector proteins Bak and Bax, indicating that they do not kill cells indiscriminately through a non-apoptotic mechanism. The specificity of this class Mcl-1 inhibitors was further confirmed by using cell lines developed by retroviral transduction of lymphoma cells isolated from Eg-myc transgenic mice which survival depends on the expression of individual prosurvival protein. 483 led to sensitization of Eg-myc lymphomas overexpressing Mcl-1 but did not show effect on cells overexpressing Bcl-2 anti-apoptotic protein, opposite of ABT-263 (FIG. 5B). These data demonstrate that 483 selectively kills Mcl-1-dependent cell lines, consistent with its binding affinity profile.

Example VIII

This example demonstrates that 483 synergizes with ABT-263 to kill Panc-1 cells.

Figure 6:
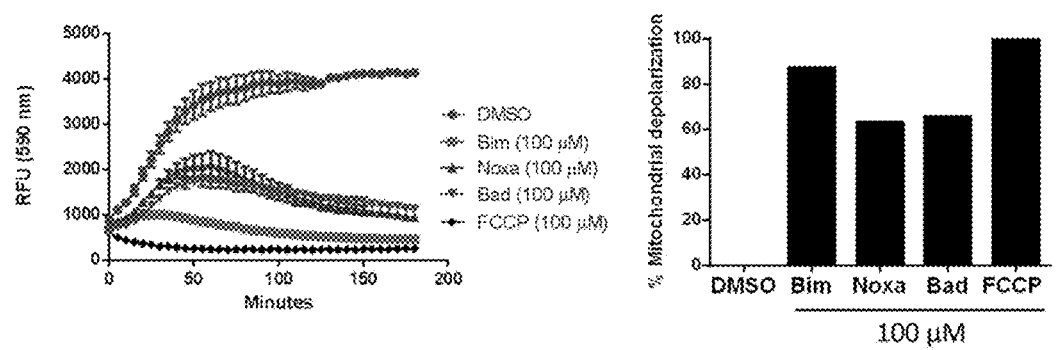
FIG. 6: Panc-1 cells are co-dependent on anti-apoptotic Bcl-2 family proteins: Mcl-1, Bcl-2 and Bcl-xL. Panc-1 cell line was subjected to whole cell BH3 profiling with JC-1 dye. The graph on the left is showing the kinetic fluorescent readings for 180 minutes and is color coded according to the key on the right of each set. The bar graphs are normalized to that of DMSO and FCCP (0% loss and 100% loss of mitochondrial membrane potential respectively) and are derived from the area under the curve.
Figure 7:
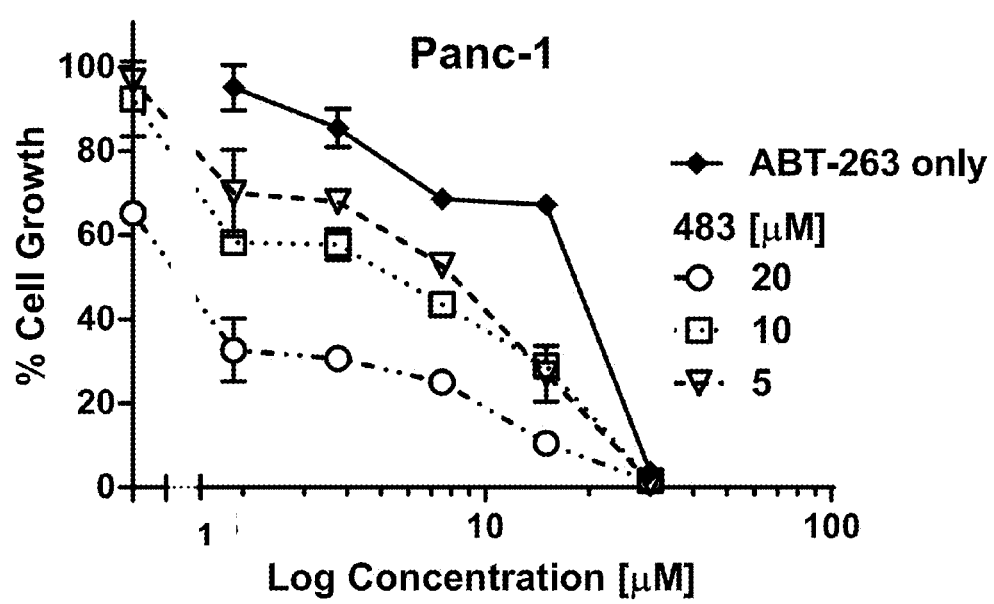
FIG. 7: 483 synergizes with ABT-263 to kill Panc-1 cells. Cell growth inhibition of ABT263 against Panc-1 in the presence of 483 for 48 h determined by MTT assay.

Mcl-1 has been well characterized as a resistance factor for the Bcl-2/Bcl-xL inhibitors and many reports have demonstrated that siRNA-mediated knockdown of Mcl-1 sensitize cancer cells to killing by Bcl-2/Bcl-xL inhibitors, such as ABT-737 (see, e.g., Konopleva, M., et al., (2006) Cancer cell 10, 375-388; Chen, S., et al., (2007) Cancer research 67, 782-791; Lin, X., et al., (2007) Oncogene 26, 3972-3979. Furthermore, using BH3 profiling functional assay we have demonstrated that Panc-1 cells are co-dependent on anti-apoptotic Bcl-2 family proteins: Mcl-1, Bcl-2 and Bcl-xL (FIG. 6). Thus the combination of ABT-263 and 483 in Panc-1 cancer cell line was tested. As expected, ABT-263 had little effect on this cell line (FIG. 7). 483 substantially shifted the dose-response curve of ABT-263 in Panc-1 cells, $IC_{50}$ of cell growth inhibition is improved more than 660 fold, indicating an ability to potentiate the effect of Bcl-1/Bcl-xL inhibition. These data further demonstrate that the 483 is indeed cell-active Mcl-1 inhibitors that behave as predicted in sensitizing cancer cells to the effects of Bcl-2/Bcl-xL inhibitors.

Example IX

This example demonstrates that 483LM disrupts the Mcl-1/BAK protein-protein interactions in Panc-1 cell line.

Figure 8:
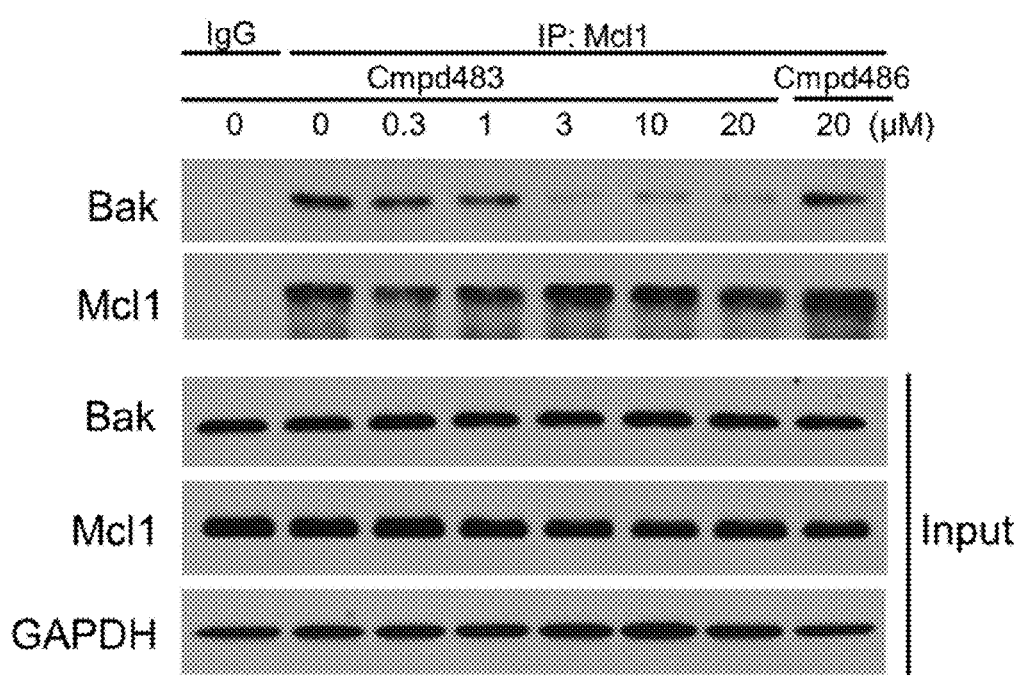
FIG. 8: 483LM disrupts the Mcl-1/BAK protein-protein interactions in Panc-1 cell line. Immunoprecipitation of Mcl-1 protein after treatment of Panc-1 cells with different concentrations of 483 and inactive compound 486 using Mcl-1 antibody followed by Western blot analysis.

Consistent with inhibition of Mcl-1 anti-apoptotic function, co-immunoprecipitation of Mcl-1 protein after treatment of Panc-1 with different concentrations of 483 and inactive compound 486 showed that 483 caused dose-dependent disruption of the protein-protein interactions between Mcl-1 and Bak, but not with inactive compound 486, demonstrating that the observed Mcl-1/Bak disruption is specific (FIG. 8).

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

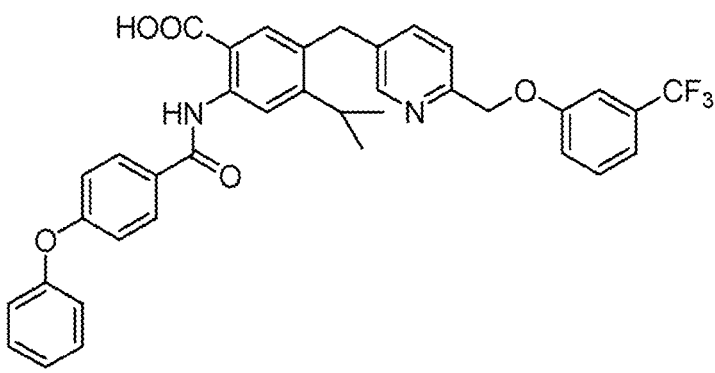

What is claimed is:

1. A compound selected from the group consisting of:

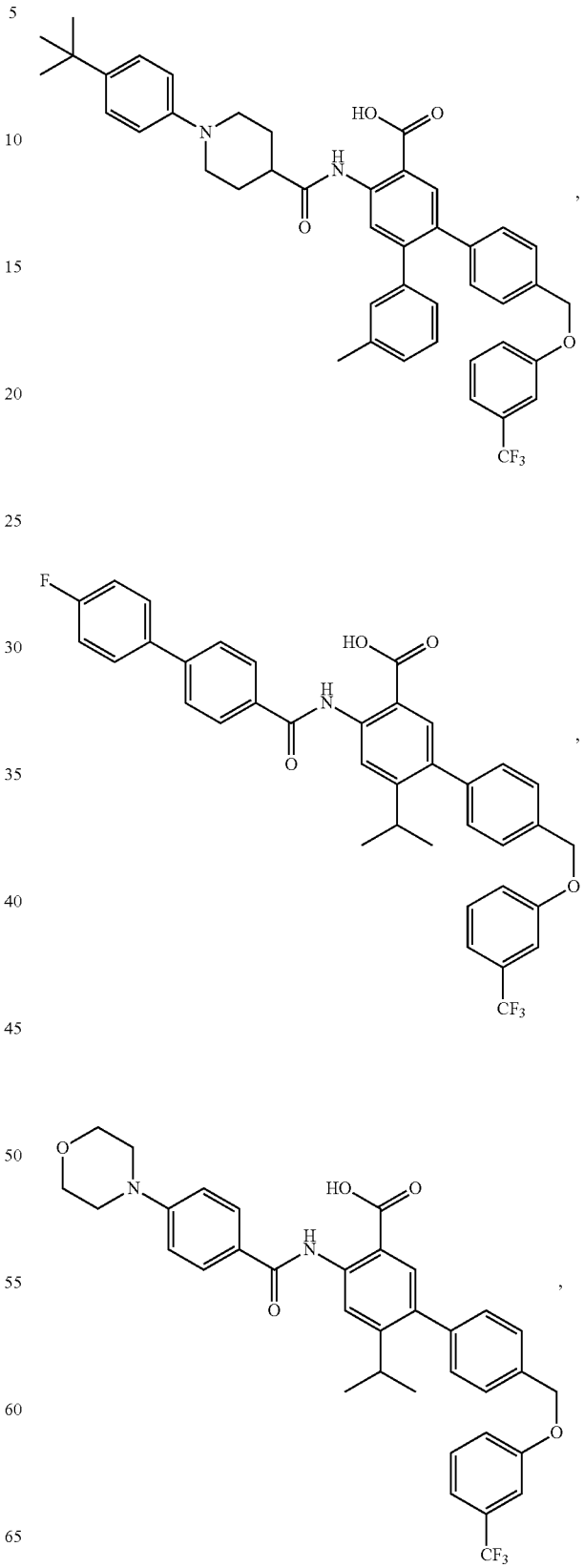

129
-continued
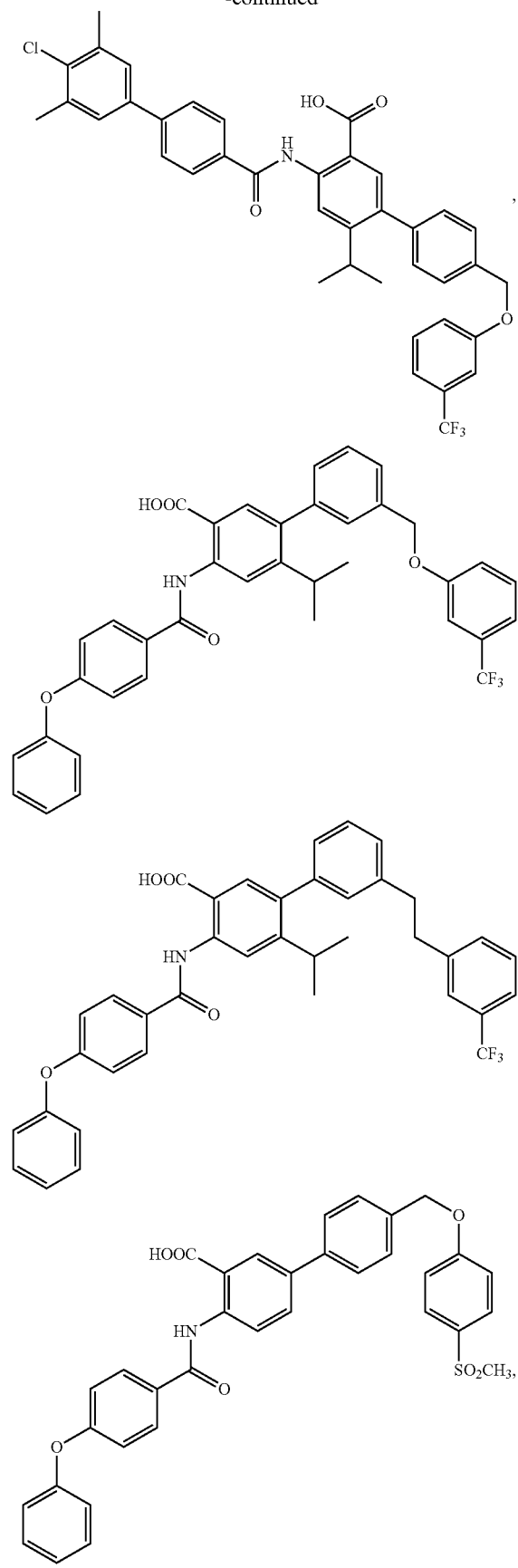
130
-continued
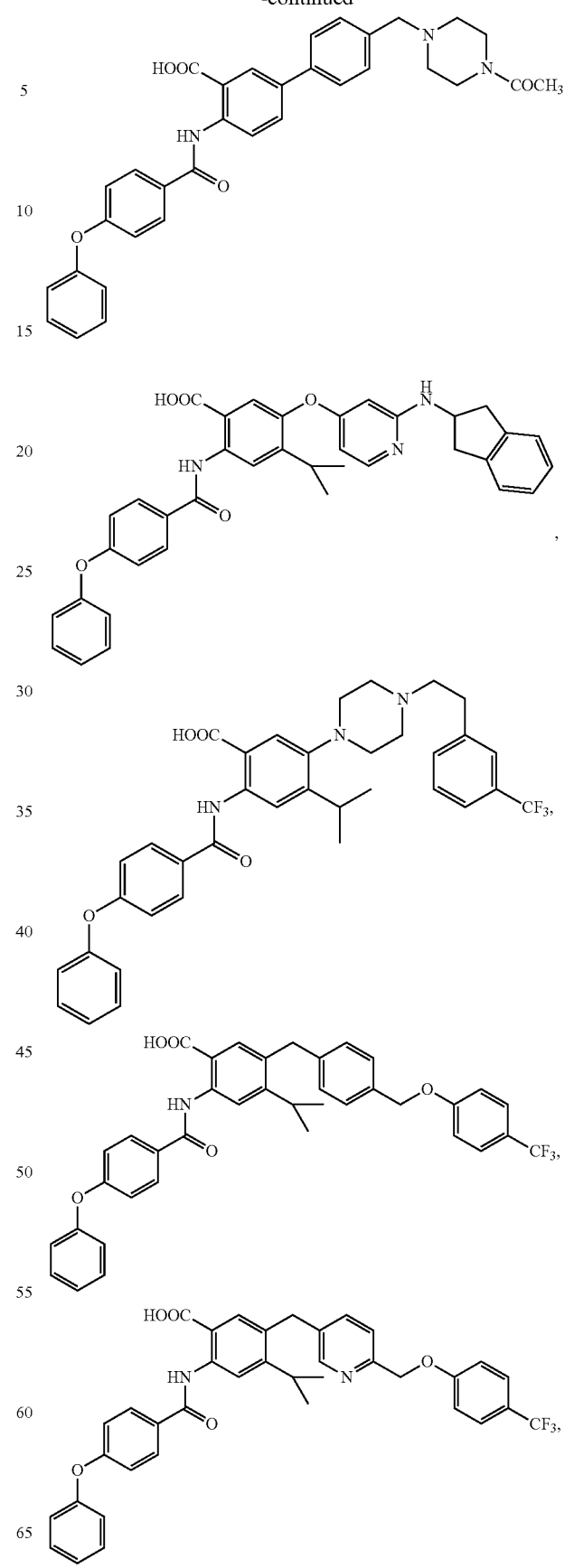

131
-continued
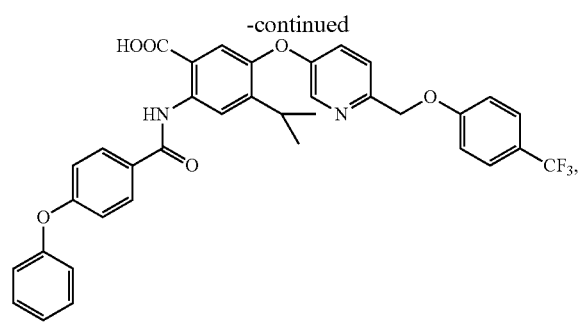
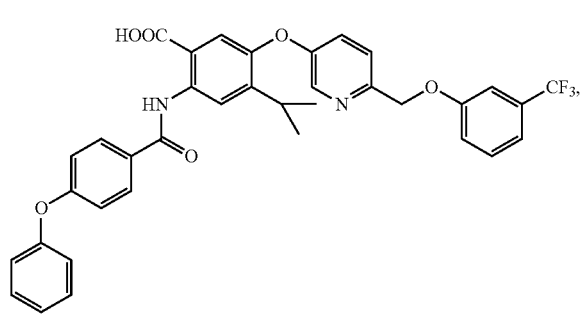
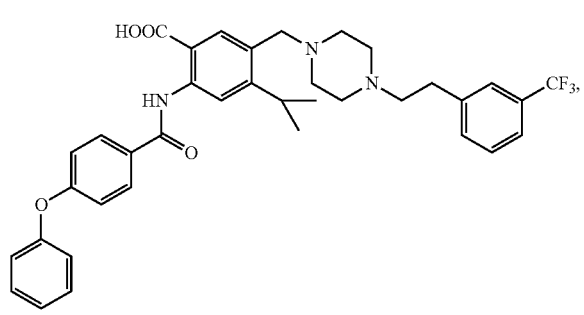
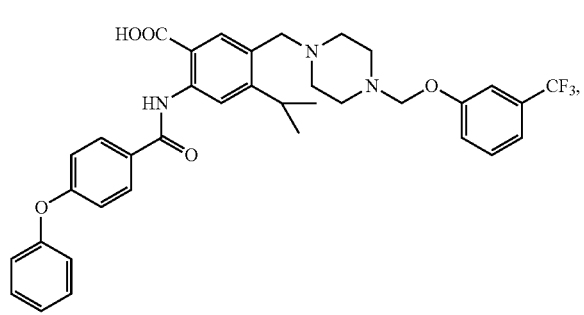
132
-continued
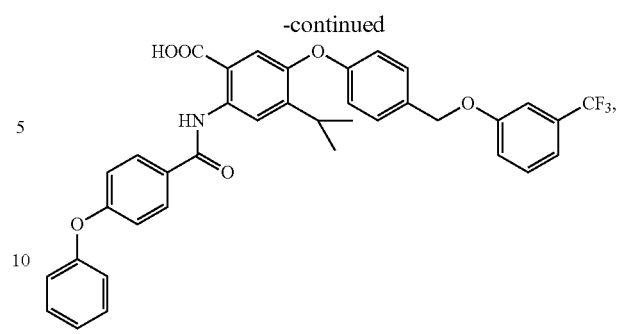
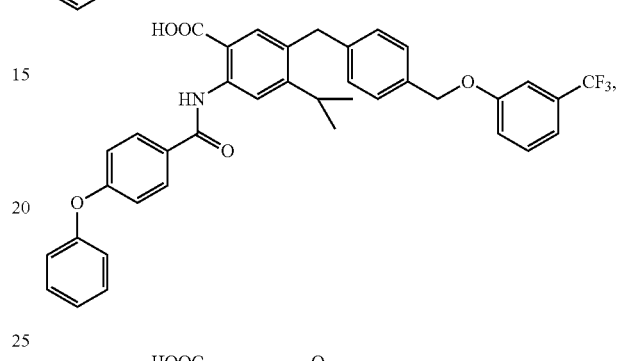
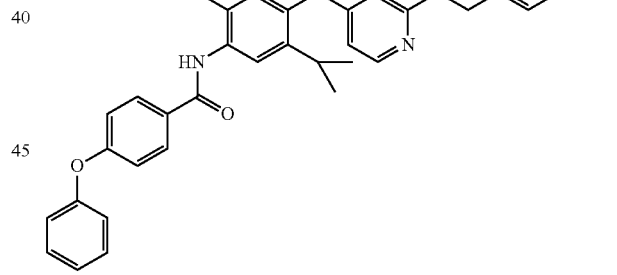
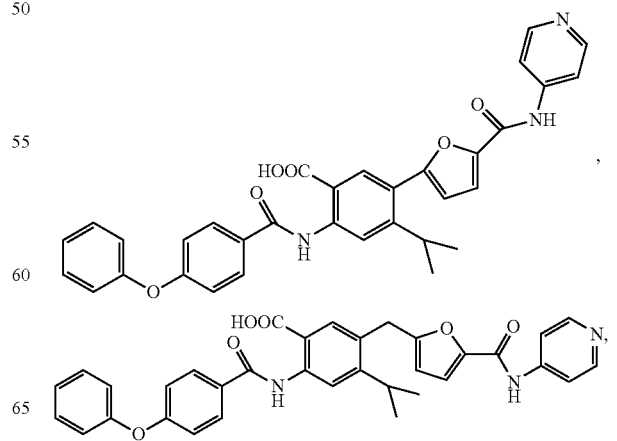

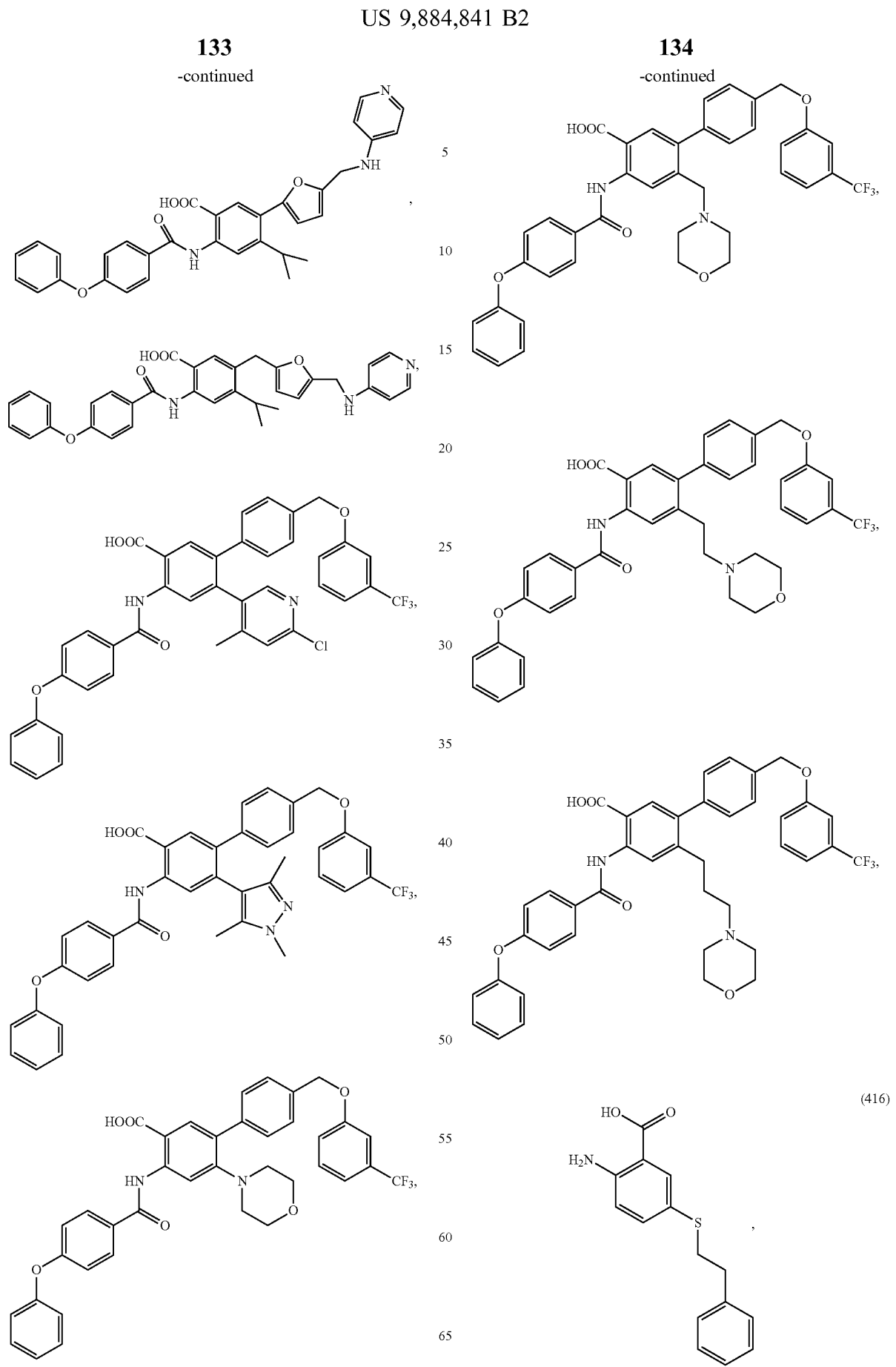

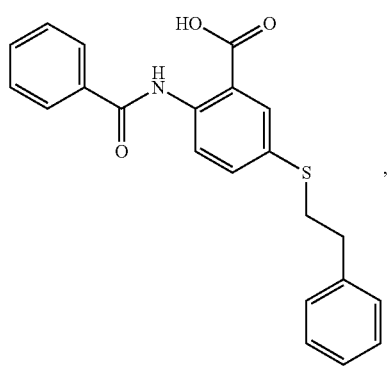 (364)
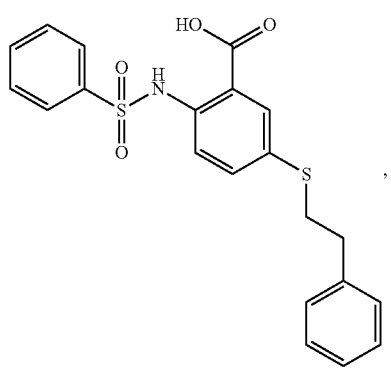 (368)
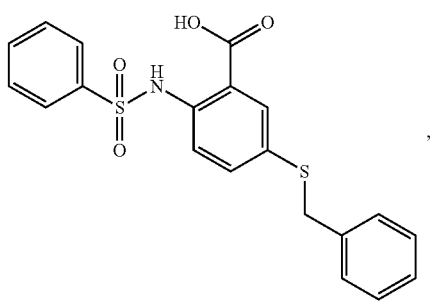 (392)
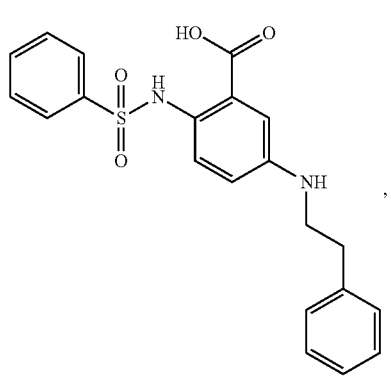 (404)
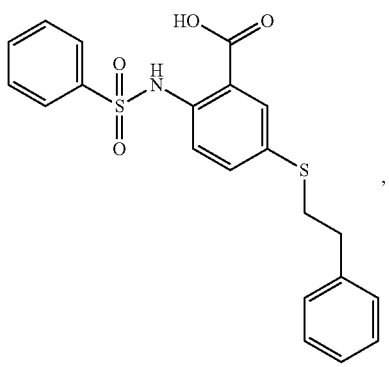 (368)
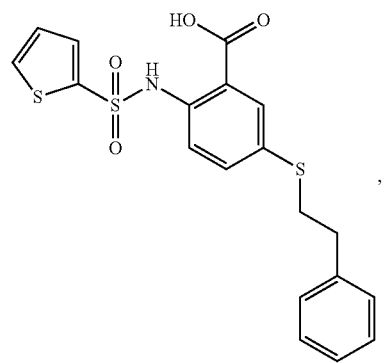 (387)
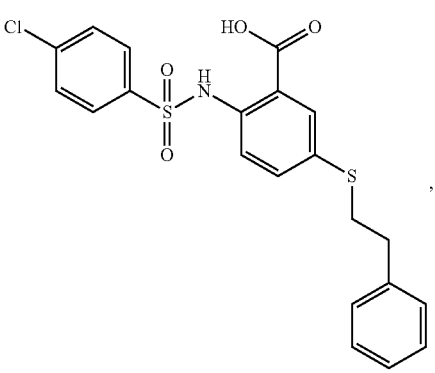 (381)
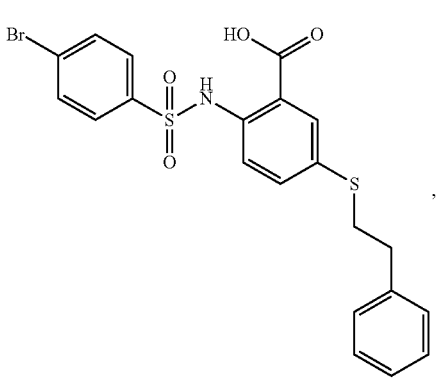 (389)

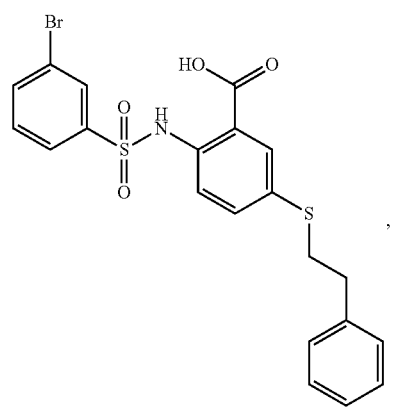
(384)
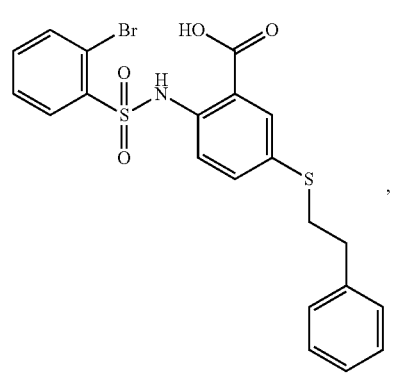
(386)
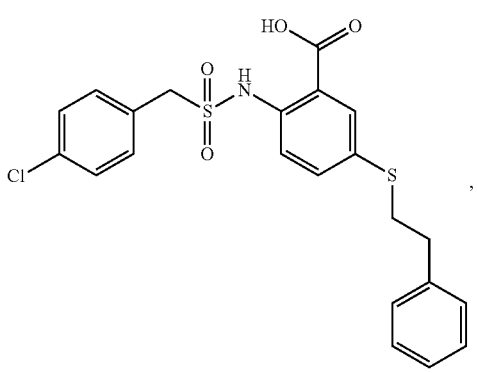
(398)
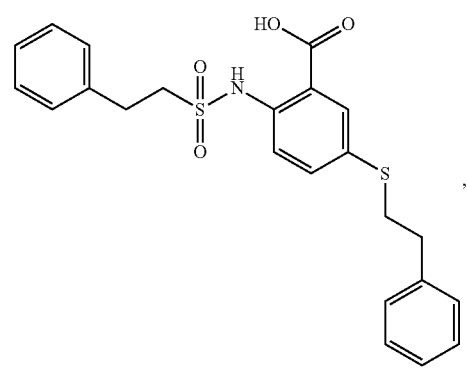
(443)
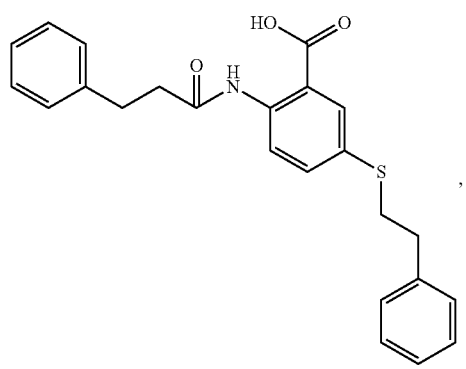
(454)
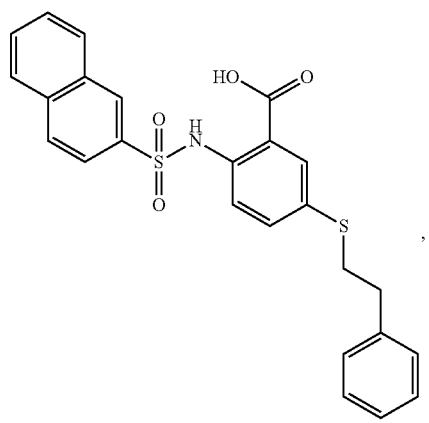
(382)
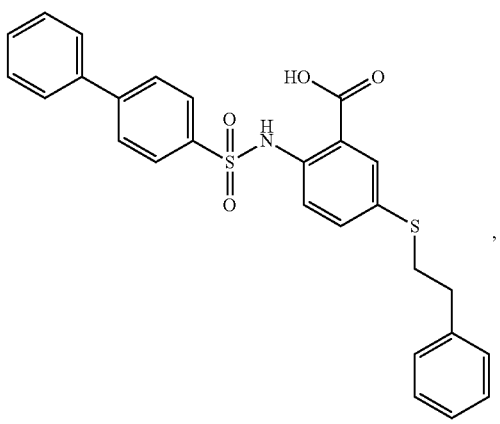
(378)
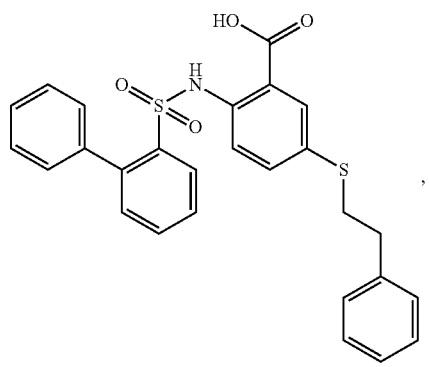
(458)

(418)
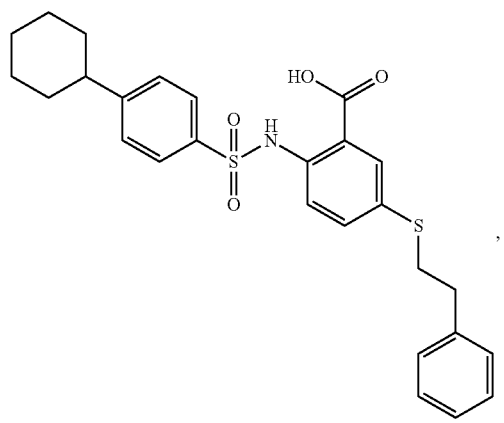
(380)
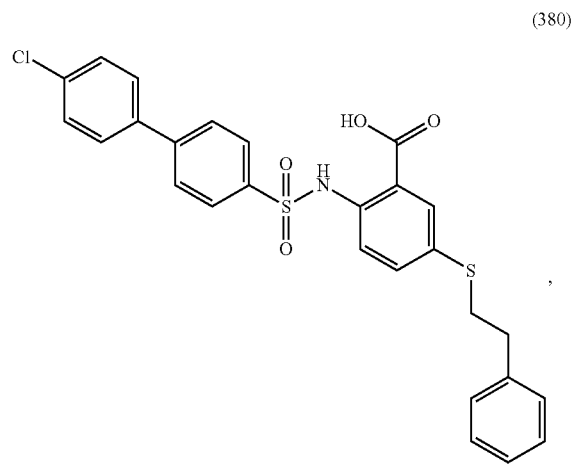
(376)
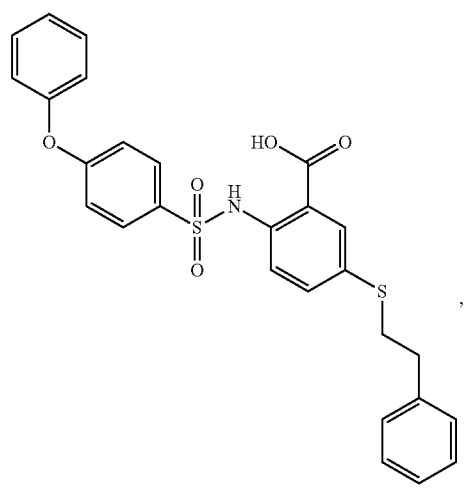
(396)
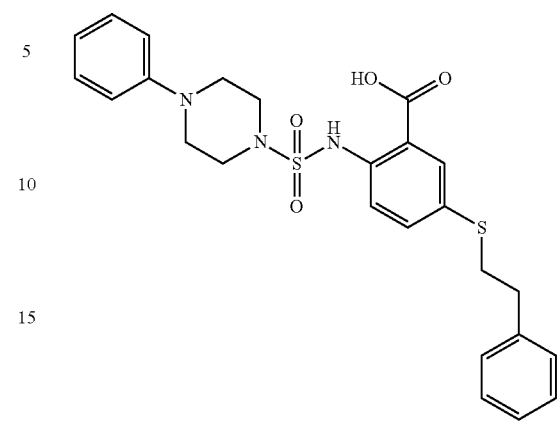
(456)
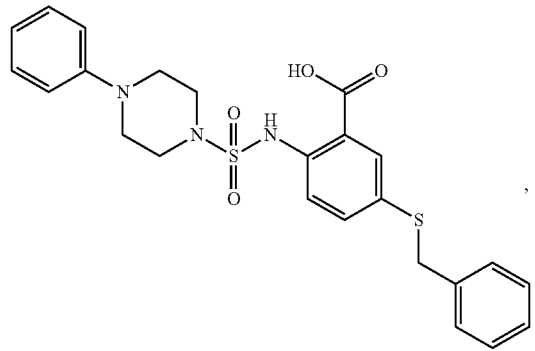
(414)
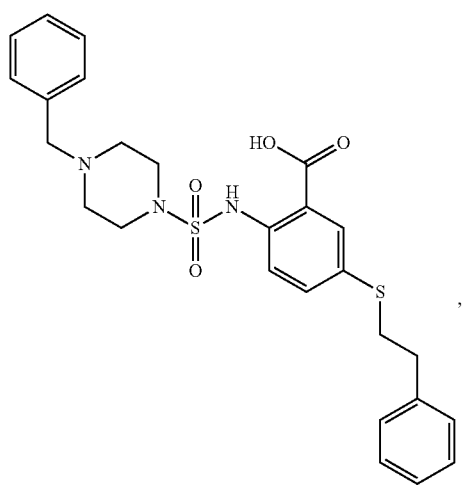

(462)
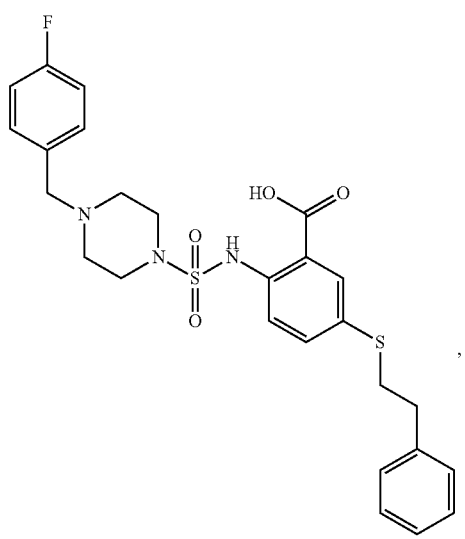
(466)
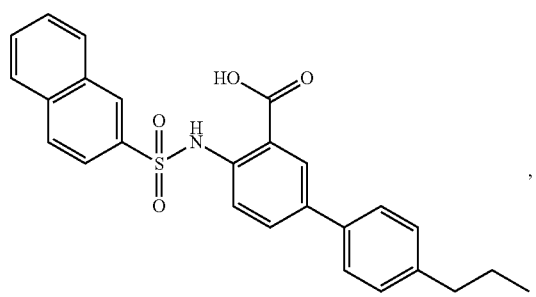
(467)
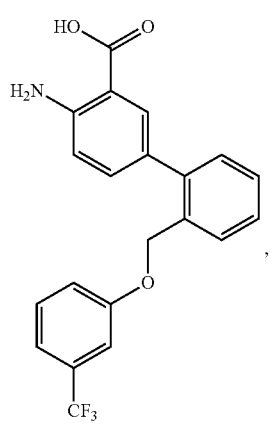
(468)
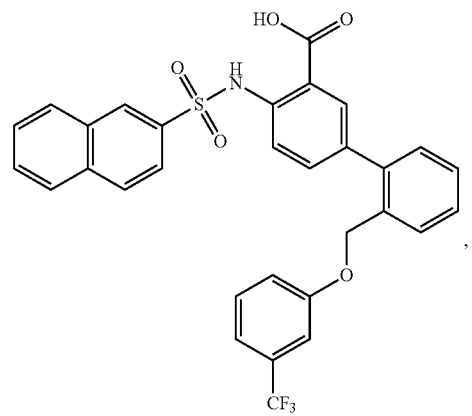
(469)
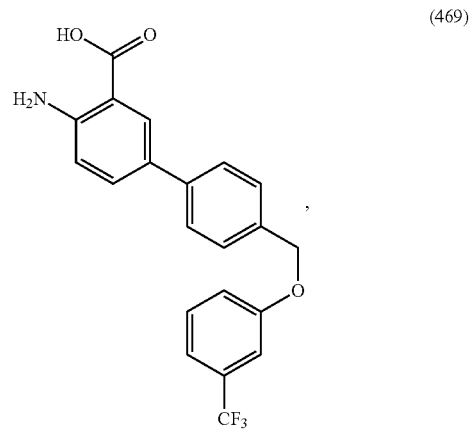
(471)
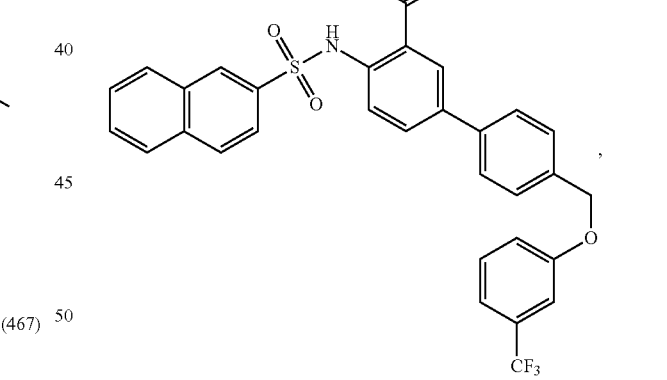
(473)
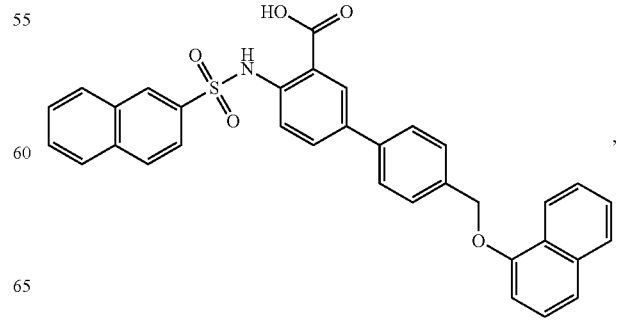

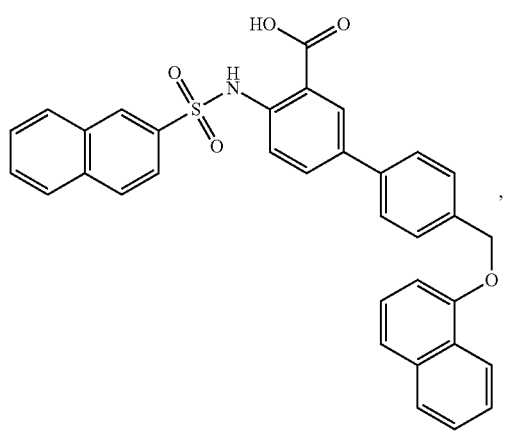
(475)
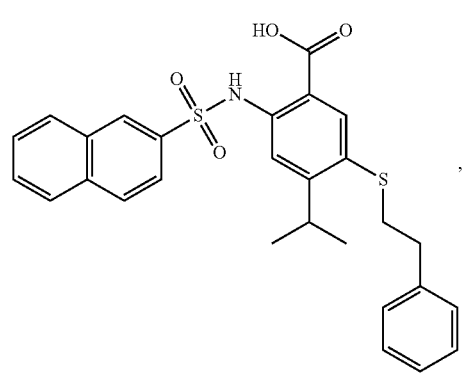
(478)
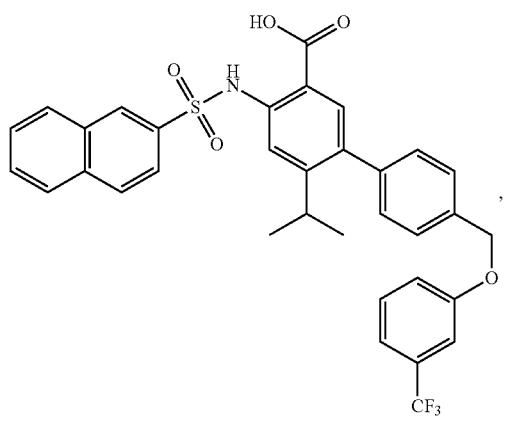
(474)
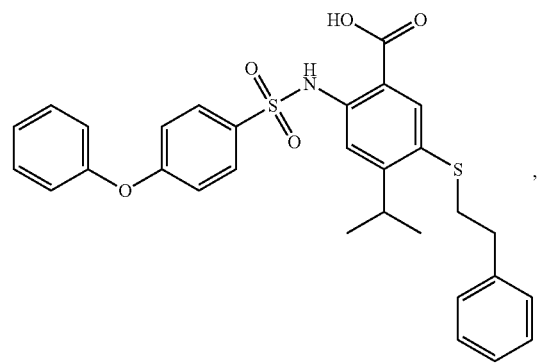
(476)
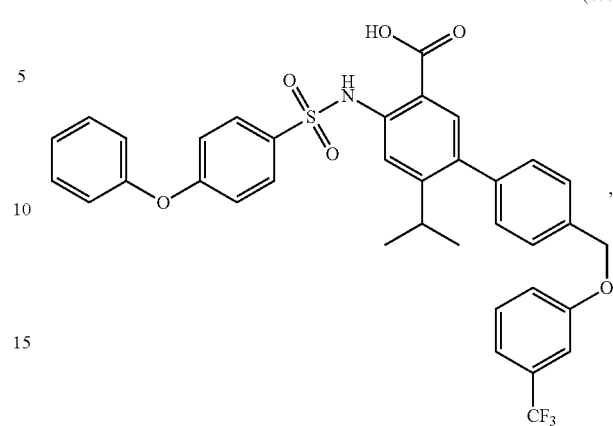
(477)
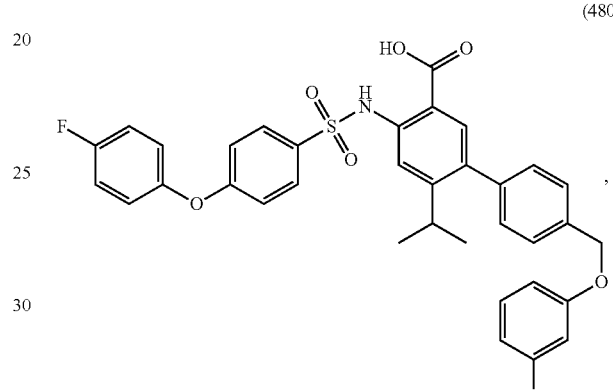
(480)
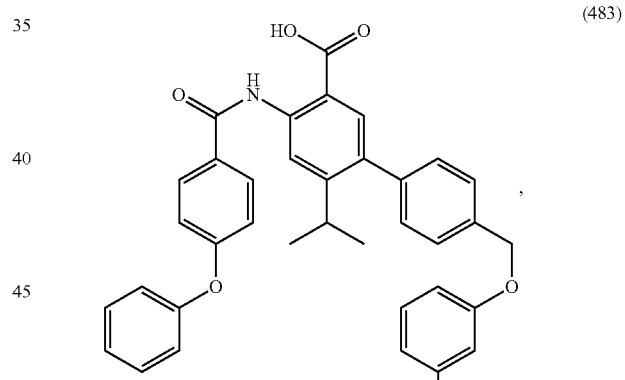
(483)
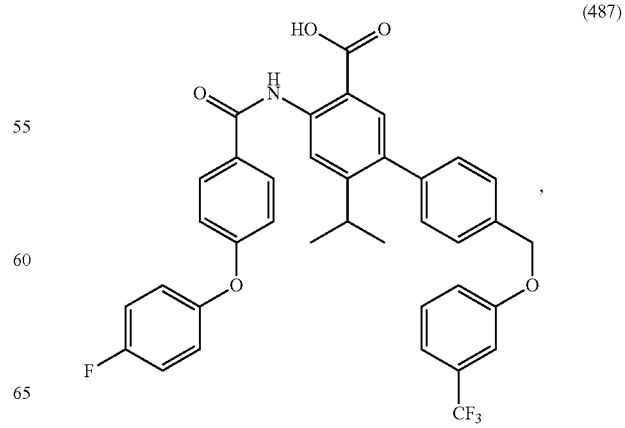
(487)

(481)
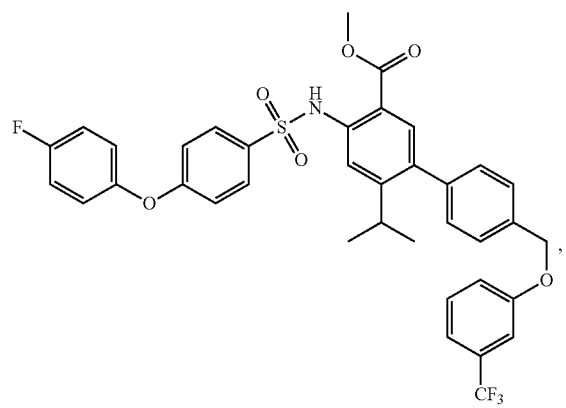
(482)
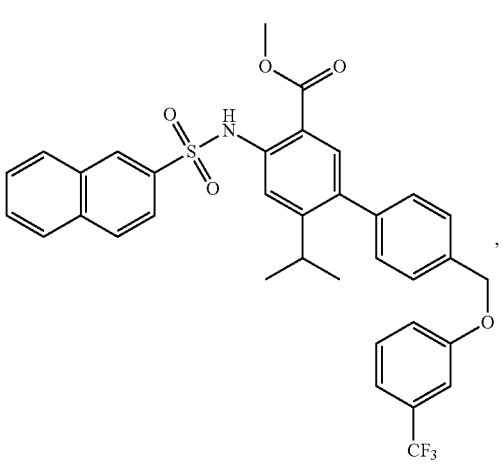
(486)
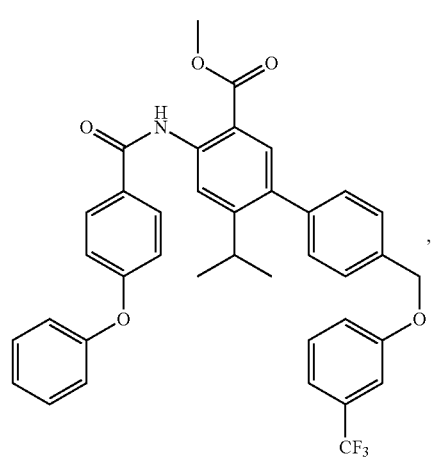
(395)
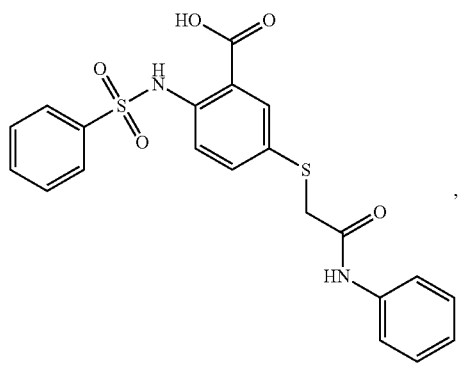
(410)
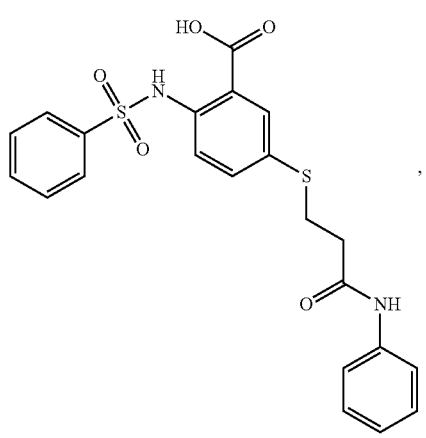
(429)
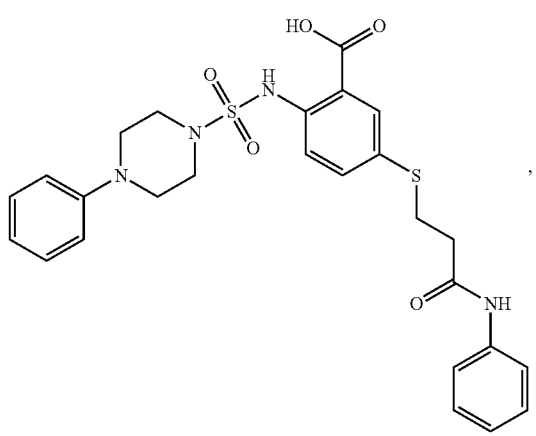
(435)
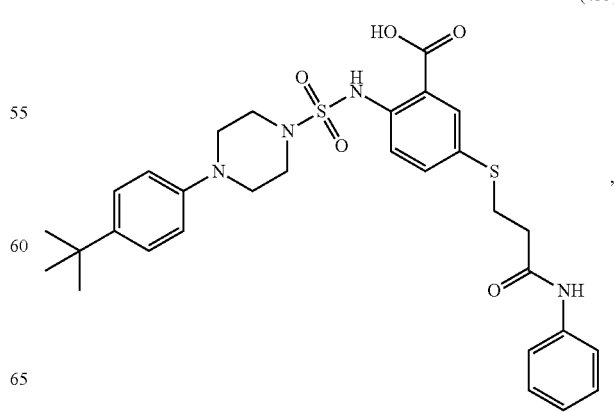

-continued
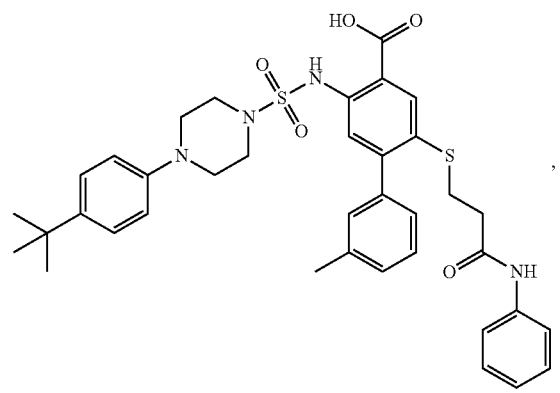
(479)
and
-continued
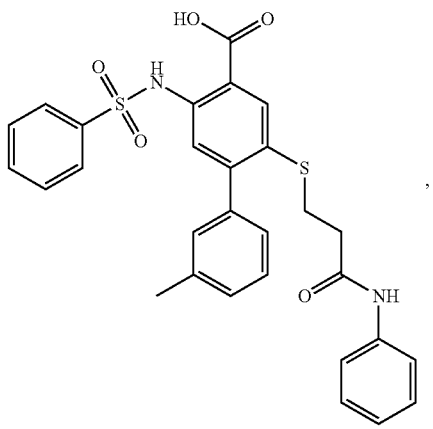
(485)
or a pharmaceutically acceptable salt, solvate, thereof.
2. A composition comprising the compound of claim 1 and a pharmaceutically acceptable carrier.
* * * * *

UNITED STATES PATENT AND TRADEMARK OFFICE
CERTIFICATE OF CORRECTION

PATENT NO. : 9,884,841 B2  Page 1 of 2
APPLICATION NO. : 15/134098
DATED : February 6, 2018
INVENTOR(S) : Zaneta Nikolovska-Coleska et al.

It is certified that error appears in the above-identified patent and that said Letters Patent is hereby corrected as shown below:

In Claim 1, Column 131, the compound on Lines 55-65 is:

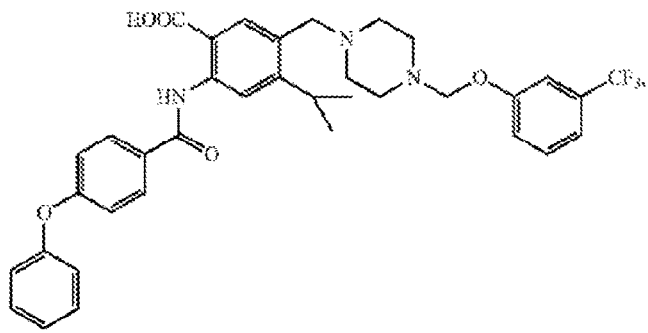

It should be:

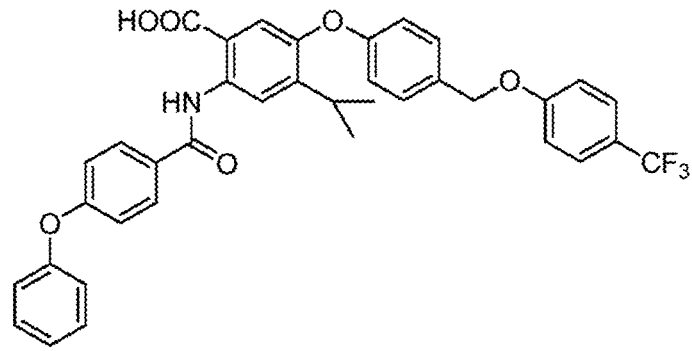

Signed and Sealed this
Eighth Day of May, 2018

Andrei Iancu
*Director of the United States Patent and Trademark Office*

CERTIFICATE OF CORRECTION (continued)
U.S. Pat. No. 9,884,841 B2

In Claim 1, Column 132, the compound on Lines 25-37 is:

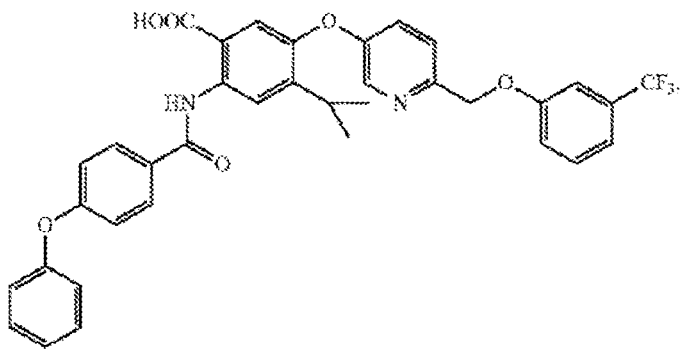

It should be: